(12) United States Patent
Kim

(10) Patent No.: US 12,023,273 B2
(45) Date of Patent: Jul. 2, 2024

(54) MEDICAL COOLING DEVICE AND COOLING METHOD USING THE SAME

(71) Applicant: RECENSMEDICAL, INC., Ulsan (KR)

(72) Inventor: Gun-Ho Kim, Ulsan (KR)

(73) Assignee: RecensMedical, Inc., Ulsan (KR)

( * ) Notice: Subject to any disclaimer, the term of this patent is extended or adjusted under 35 U.S.C. 154(b) by 775 days.

(21) Appl. No.: 17/137,237

(22) Filed: Dec. 29, 2020

(65) Prior Publication Data

US 2021/0113365 A1 Apr. 22, 2021

Related U.S. Application Data

(63) Continuation of application No. PCT/KR2019/009411, filed on Jul. 29, 2019.
(Continued)

(30) Foreign Application Priority Data

Aug. 16, 2018 (KR) .................. 10-2018-0095741
Sep. 20, 2018 (KR) .................. 10-2018-0112634
Nov. 15, 2018 (KR) .................. 10-2018-0140508

(51) Int. Cl.
*A61F 7/00* (2006.01)
*A61M 19/00* (2006.01)
*F28D 15/02* (2006.01)

(52) U.S. Cl.
CPC ........... *A61F 7/0085* (2013.01); *A61M 19/00* (2013.01); *F28D 15/0275* (2013.01);
(Continued)

(58) Field of Classification Search
CPC ...... A61F 2007/0054; A61F 2007/0056; A61F 2007/0075; A61F 2007/0078;
(Continued)

(56) References Cited

U.S. PATENT DOCUMENTS 2,004,823 A 6/1935 Meyer
2,044,823 A 6/1936 Whiteside
(Continued)

FOREIGN PATENT DOCUMENTS

CN 103536350 A 1/2014
CN 107530185 A 1/2018
(Continued)

OTHER PUBLICATIONS

PCT/KR2017/012935 International Search Report and Written Opinion dated Jun. 4, 2018.
(Continued)

*Primary Examiner* — Michael F Peffley
(74) *Attorney, Agent, or Firm* — Knobbe, Martens, Olson & Bear, LLP

(57) ABSTRACT

An embodiment of the present invention provides a medical cooling device including a cooling medium configured to cool a target region through thermal contact with the target region, a cooling generator configured to supply cooling energy to the cooling medium, and a cooling medium accommodating unit that has one surface to which the cooling generator is attached and that is configured to thermally connect the cooling medium to the cooling generator, wherein a center-of-cooling-power region is disposed in a region where the cooling medium and the cooling medium accommodating unit overlap and has a center of cooling power which is a center with respect to thermal conductivity of the center-of-cooling-power region, and a distance from a front end of the cooling medium to the center of cooling power is less than or equal to 30 mm.

16 Claims, 64 Drawing Sheets

Related U.S. Application Data

(60) Provisional application No. 62/703,894, filed on Jul. 27, 2018.

(52) U.S. Cl.
CPC .............. *A61F 2007/0056* (2013.01); *A61F 2007/0087* (2013.01); *A61M 2205/3368* (2013.01); *A61M 2205/3606* (2013.01); *A61M 2205/366* (2013.01)

(58) Field of Classification Search
CPC ...... A61F 2007/0087; A61F 2007/0096; A61F 2007/0261; A61F 2007/0285; A61F 2007/0295; A61F 7/007; A61F 7/0085; A61F 9/00; A61F 9/007; A61M 11/007; A61M 2205/073; A61M 2205/3368; A61M 2205/3606; A61M 2205/366; F28D 15/0275
See application file for complete search history.

(56) References Cited

U.S. PATENT DOCUMENTS

| | | | |
|---|---|---|---|
| 3,289,749 A | 12/1966 | Crump | |
| 4,646,735 A | 3/1987 | Seney | |
| 5,976,123 A | 11/1999 | Baumgardner et al. | |
| 6,099,521 A | 8/2000 | Shadduck | |
| 6,141,985 A | 11/2000 | Cluzeau et al. | |
| 6,430,956 B1 * | 8/2002 | Haas | A61B 18/02 62/293 |
| 6,632,219 B1 | 10/2003 | Baranov et al. | |
| 6,669,688 B2 | 12/2003 | Svaasand et al. | |
| 7,037,326 B2 | 5/2006 | Lee | |
| 7,780,656 B2 | 8/2010 | Tankovich | |
| 7,963,959 B2 | 6/2011 | Da Silva et al. | |
| 8,083,734 B2 | 12/2011 | Steinfatt et al. | |
| 8,177,827 B2 | 5/2012 | Shapiro | |
| 8,256,233 B2 | 9/2012 | Boyden et al. | |
| 8,652,131 B2 | 2/2014 | Muller et al. | |
| 8,672,879 B2 | 3/2014 | Grant et al. | |
| 8,788,060 B2 | 7/2014 | Nebrigic et al. | |
| 8,858,583 B2 | 10/2014 | Shtram et al. | |
| 9,017,318 B2 | 4/2015 | Fourkas et al. | |
| 9,039,688 B2 | 5/2015 | Palmer, III et al. | |
| 9,066,712 B2 | 6/2015 | Fourkas et al. | |
| 9,113,855 B2 | 8/2015 | Burger et al. | |
| 9,398,975 B2 | 7/2016 | Muller et al. | |
| 9,522,031 B2 | 12/2016 | Anderson et al. | |
| 9,549,773 B2 | 1/2017 | Anderson et al. | |
| 9,642,741 B2 | 5/2017 | Feng et al. | |
| 9,801,677 B2 | 10/2017 | Anderson et al. | |
| 9,855,166 B2 | 1/2018 | Anderson et al. | |
| 9,956,355 B2 | 5/2018 | Besirli et al. | |
| 9,974,684 B2 | 5/2018 | Anderson et al. | |
| 10,085,881 B2 | 10/2018 | Karnik et al. | |
| 10,154,870 B2 | 12/2018 | Ottanelli | |
| 10,188,444 B2 | 1/2019 | Fourkas et al. | |
| 10,213,244 B2 | 2/2019 | Fourkas et al. | |
| 10,322,248 B2 | 6/2019 | Besirli et al. | |
| 10,363,080 B2 | 7/2019 | Elkins et al. | |
| 10,543,032 B2 | 1/2020 | Babkin | |
| 11,278,341 B2 * | 3/2022 | Kim | A61F 7/007 |
| 11,464,669 B2 * | 10/2022 | Kim | A61F 7/12 |
| 2002/0120315 A1 | 8/2002 | Furuno et al. | |
| 2004/0102768 A1 | 5/2004 | Cluzeau et al. | |
| 2004/0111087 A1 * | 6/2004 | Stern | A61N 1/403 606/41 |
| 2005/0059940 A1 | 3/2005 | Weber et al. | |
| 2006/0200117 A1 | 9/2006 | Hermans | |
| 2006/0213509 A1 | 9/2006 | Marin et al. | |
| 2007/0005048 A1 | 1/2007 | Niedbala et al. | |
| 2007/0239236 A1 | 10/2007 | Manstein | |
| 2008/0164296 A1 | 7/2008 | Shelton et al. | |
| 2008/0221561 A1 | 9/2008 | Geiger et al. | |
| 2009/0036846 A1 | 2/2009 | Dacquay et al. |
| 2009/0062751 A1 | 3/2009 | Newman, Jr. |
| 2009/0163902 A1 | 6/2009 | DeLonzor et al. |
| 2010/0010480 A1 | 1/2010 | Mehta et al. |
| 2010/0087805 A1 | 4/2010 | Citterio et al. |
| 2010/0196343 A1 | 8/2010 | O'Neil et al. |
| 2010/0198207 A1 | 8/2010 | Elkins et al. |
| 2011/0072834 A1 | 3/2011 | Ishikura et al. |
| 2011/0098791 A1 | 4/2011 | Kim |
| 2011/0137268 A1 | 6/2011 | Thomason et al. |
| 2011/0152850 A1 | 6/2011 | Niedbala et al. |
| 2011/0177474 A1 | 7/2011 | Jamnia et al. |
| 2011/0224761 A1 | 9/2011 | Manstein |
| 2012/0130458 A1 | 5/2012 | Ryba et al. |
| 2012/0191166 A1 | 7/2012 | Callister et al. |
| 2012/0232549 A1 | 9/2012 | Willyard et al. |
| 2012/0265278 A1 | 10/2012 | Fourkas et al. |
| 2013/0116719 A1 | 5/2013 | Shtram et al. |
| 2013/0296811 A1 | 11/2013 | Bangera et al. |
| 2013/0315924 A1 | 11/2013 | Hsu et al. |
| 2014/0012226 A1 | 1/2014 | Hochman |
| 2014/0142384 A1 | 5/2014 | Chung et al. |
| 2014/0200511 A1 | 7/2014 | Boyden et al. |
| 2014/0277023 A1 | 9/2014 | Sekino et al. |
| 2015/0051545 A1 | 2/2015 | Henderson et al. |
| 2016/0058488 A1 | 3/2016 | Fourkas et al. |
| 2016/0183996 A1 | 6/2016 | Burger et al. |
| 2016/0242956 A1 | 8/2016 | Pilby Gomez |
| 2016/0262820 A1 | 9/2016 | Allison et al. |
| 2016/0279350 A1 | 9/2016 | Besirli et al. |
| 2017/0014174 A1 | 1/2017 | Levine et al. |
| 2017/0062793 A1 | 3/2017 | Zakharyan et al. |
| 2017/0224935 A1 | 8/2017 | Hoffmann et al. |
| 2017/0231816 A1 | 8/2017 | Ryan |
| 2017/0232243 A1 | 8/2017 | Herweijer |
| 2017/0304558 A1 | 10/2017 | Besirli et al. |
| 2017/0348143 A1 | 12/2017 | Rosen et al. |
| 2017/0354451 A1 | 12/2017 | Marin et al. |
| 2018/0116705 A1 | 5/2018 | Lee et al. |
| 2018/0235805 A1 | 8/2018 | Burger et al. |
| 2018/0310979 A1 | 11/2018 | Peled et al. |
| 2019/0000524 A1 | 1/2019 | Rosen et al. |
| 2019/0015146 A1 | 1/2019 | DuBois |
| 2019/0015602 A1 | 1/2019 | Besirli et al. |
| 2019/0038459 A1 | 2/2019 | Karnik et al. |
| 2019/0175394 A1 | 6/2019 | Kim |
| 2019/0175395 A1 | 6/2019 | Kim |
| 2019/0175396 A1 | 6/2019 | Kim |
| 2019/0254866 A1 | 8/2019 | Whiteley et al. |
| 2019/0290881 A1 | 9/2019 | Kim |
| 2020/0054483 A1 | 2/2020 | Kim |
| 2020/0206025 A1 | 7/2020 | Chalberg, Jr. et al. |
| 2022/0160414 A1 | 5/2022 | Kim et al. |

FOREIGN PATENT DOCUMENTS

| | | |
|---|---|---|
| EP | 1030611 B1 | 9/2004 |
| EP | 1401347 B1 | 8/2011 |
| EP | 2010087 B1 | 11/2014 |
| EP | 2910276 A1 | 8/2015 |
| EP | 2759272 B1 | 11/2018 |
| JP | H0492663 A | 3/1992 |
| JP | H0686818 A | 3/1994 |
| JP | H06321268 A | 11/1994 |
| JP | H10230435 A | 9/1998 |
| JP | 2002505155 A | 2/2002 |
| JP | 2004515270 A | 5/2004 |
| JP | 2005080832 A | 3/2005 |
| JP | 4049358 B2 | 2/2008 |
| JP | 2008212638 A | 9/2008 |
| JP | 2008545462 A | 12/2008 |
| JP | 2009034273 A | 2/2009 |
| JP | 2009056320 A | 3/2009 |
| JP | 2011077314 A | 4/2011 |
| JP | 2012143279 A | 8/2012 |
| JP | 2013142410 A | 7/2013 |
| JP | 2014028130 A | 2/2014 |
| JP | 2014198238 A | 10/2014 |
| JP | 2015510802 A | 4/2015 |

(56) References Cited

FOREIGN PATENT DOCUMENTS

| | | |
|---|---|---|
| JP | 2017113635 A | 6/2017 |
| KR | 980005117 U | 3/1998 |
| KR | 19980058500 U | 10/1998 |
| KR | 100200669 B1 | 6/1999 |
| KR | 20030068633 A | 8/2003 |
| KR | 20040093706 A | 11/2004 |
| KR | 20040094508 A | 11/2004 |
| KR | 100786539 B1 | 12/2007 |
| KR | 100790758 B1 | 1/2008 |
| KR | 20080045022 A | 5/2008 |
| KR | 100851274 B1 | 8/2008 |
| KR | 20100041207 A | 4/2010 |
| KR | 20100060222 A | 6/2010 |
| KR | 20100135863 A | 12/2010 |
| KR | 101053835 B1 | 8/2011 |
| KR | 10-1073839 B1 | 10/2011 |
| KR | 20110119640 A | 11/2011 |
| KR | 20120040760 A | 4/2012 |
| KR | 20120115703 A | 10/2012 |
| KR | 20130087770 A | 8/2013 |
| KR | 101366126 B1 | 2/2014 |
| KR | 101386137 B1 | 4/2014 |
| KR | 20140052667 A | 5/2014 |
| KR | 20140069431 A | 6/2014 |
| KR | 20150030264 A | 3/2015 |
| KR | 20150062492 A | 6/2015 |
| KR | 101577208 B1 | 12/2015 |
| KR | 20160048425 A | 5/2016 |
| KR | 101707659 B1 | 2/2017 |
| KR | 101719459 B1 | 3/2017 |
| KR | 20170041776 A | 4/2017 |
| KR | 20170083399 A | 7/2017 |
| KR | 20170089842 A | 8/2017 |
| KR | 20170130470 A | 11/2017 |
| KR | 101813652 B1 | 12/2017 |
| KR | 101819204 B1 | 1/2018 |
| KR | 101840346 B1 | 5/2018 |
| KR | 101862127 B1 | 5/2018 |
| KR | 20180054247 A | 5/2018 |
| KR | 20180109828 A | 10/2018 |
| KR | 101936890 B1 | 1/2019 |
| KR | 20190063724 A | 6/2019 |
| KR | 20190114710 A | 10/2019 |
| KR | 20190124971 A | 11/2019 |
| KR | 20200070095 A | 6/2020 |
| KR | 20200070139 A | 6/2020 |
| WO | WO-9220289 A1 | 11/1992 |
| WO | WO-2016154399 A1 | 9/2016 |
| WO | WO-2017196548 A1 | 11/2017 |
| WO | WO-2018221963 A2 | 12/2018 |
| WO | WO-2018231868 A1 | 12/2018 |
| WO | WO-2020022858 A1 | 1/2020 |

OTHER PUBLICATIONS

PCT/KR2017/013901 International Search Report and written opinion dated Aug. 8, 2018.
PCT/KR2018/003773 International Search Report and Written Opinion dated Jul. 6, 2018.
PCT/KR2018/006169 International Search Report and Written Opinion dated Nov. 7, 2018.
PCT/KR2018/016491 International Search Report and Written Opinion dated May 30, 2019.
PCT/KR2019/005105 International Search Report and Written Opinion dated Aug. 14, 2019.
PCT/KR2019009411 International Search Report and Written Opinion dated Nov. 15, 2019.
PCT/KR2019/017328 International Search Report and Written Opinion dated Mar. 27, 2020.
Sarifakioglu et al., Evaluating the effects of ice application on the pain felt during botulinum toxin type-a injections: a prospective, randomized, single-blind controlled trial. Ann Plast Surg 53:543-546 (2004).
Smith. Ice anesthesia for injection of dermal fillers. Dermatologic Surgery 36:812-814 (2010).
Fernandez et al. Cooling effects on nitric oxide production by rabbit ear and femoral arteries during cholinergic stimulation. Br J Pharmacol. 113:550-554 (1994).
Ostadhadi et al. Involvement of nitric oxide in serotonin-induced scratching in mice. Clin Exp Dermatol. 40:647-652 (2015).
PCT/KR2021/009072 International Search Report and Written Opinion dated Nov. 22, 2021.
KR10-2020-0130588 Office Action dated Apr. 26, 2022 (w/English Translation).
KR10-2020-0130589 Office Action dated Apr. 26, 2022 (w/English Translation).
KR10-2020-0130590 Office Action dated Apr. 26, 2022 (w/English Translation).
EP19842037.4 Extended European Search Report dated Apr. 8, 2022.
CN201980044614 First Office Action dated Jan. 5, 2023 [with English Translation].
EP19842037.4 Office Action dated Jan. 1, 2023.
Korean Application No. 10-2018-0112633 Office Action dated Jul. 14, 2023.
Korean Office Action dated Sep. 21, 2023, for KR 10-2018-0140509.

* cited by examiner

100

MEDICAL COOLING DEVICE AND COOLING METHOD USING THE SAME

CROSS-REFERENCE

This application is a Continuation of PCT/KR2019009411, filed Jul. 29, 2019, which claims priority to U.S. Application 62/703,894, filed Jul. 27, 2018. This application also claims priority to the following foreign applications: KR10-2018-0095741, filed Aug. 16, 2018, KR10-2018-0112634, filed Sep. 20, 2018, and KR10-2018-0140508, filed Nov. 15, 2018. All of which are incorporated herein by reference in their entireties.

TECHNICAL FIELD

Embodiments of the present invention relate to a medical cooling device and a cooling method using the same.

BACKGROUND ART

In general, medical practices such as surgery or treatment are bound to be accompanied by pain. Such pain can be eliminated or reduced by blocking nerve transmission through pharmacological anesthesia. However, since anesthesia has side effects, it is limitedly applied only when a long operation or treatment is required, or when the pain is relatively severe. In particular, pharmacological anesthesia has a problem in that an anesthetic is injected by a syringe, and additional pain is caused by an injection needle, which increases the patient's pain. In addition, anesthesia by the injection method requires a certain anesthesia time until the anesthesia effect is exerted, resulting in an inefficient problem of increasing surgery or treatment time due to unnecessary waiting time.

DISCLOSURE

Technical Problem

Embodiments of the present invention provide a medical cooling device and a cooling method using the same capable of anesthetizing a treatment site rapidly and safely using cryoanesthesia.

Technical Solution

An embodiment of the present invention provides a medical cooling device including a cooling medium configured to cool a target region through thermal contact with the target region, a cooling generator configured to supply cooling energy to the cooling medium, and a cooling medium accommodating unit that has one surface to which the cooling generator is attached and that is configured to thermally connect the cooling medium to the cooling generator, wherein a center-of-cooling-power region is disposed in a region where the cooling medium and the cooling medium accommodating unit overlap and has a center of cooling power which is a center with respect to thermal conductivity of the center-of-cooling-power region, and a distance from a front end of the cooling medium to the center of cooling power is less than or equal to 30 mm.

According to an embodiment of the present invention, a medicinal fluid may be transferred to the cooled target region in such a way that the medicinal fluid is stored outside the cooling medium accommodating unit and then transferred to the target region.

According to an embodiment of the present invention, the center-of-cooling-power region may be disposed on an extension line that extends in a longitudinal direction of the cooling medium from a center of the region where the cooling medium and the cooling medium accommodating unit overlap, and a position of the center-of-cooling-power region may be determined by a center-of-cooling-power parameter of the cooling medium.

According to an embodiment of the present invention, the center-of-cooling-power parameter of the cooling medium may include at least one of a thermal conductivity of the cooling medium, a distance between the cooling medium and the cooling generator, and a volume of the cooling medium.

According to an embodiment of the present invention, a cooling assembly may include the cooling generator and the cooling medium accommodating unit, and a center-of-cooling-power parameter of the cooling assembly may include at least one of a thermal conductivity of the cooling medium accommodating unit, a distance between the cooling medium accommodating unit and the cooling generator, and a volume of the cooling medium accommodating unit.

According to an embodiment of the present invention, in a case in which the cooling generator is provided as a plurality of cooling generators, the center-of-cooling-power parameter may further include a cooling amount of each cooling generator.

According to an embodiment of the present invention, the center of cooling power of the center-of-cooling-power region may be the center of the region where the cooling medium and the cooling medium accommodating unit overlap, and a length of the cooling medium may be a length within ten times a distance from a lower end of the cooling medium to the center of cooling power.

According to an embodiment of the present invention, the medical cooling device may further include a heat dissipation unit configured to dissipate heat of the cooling generator, and a longitudinal direction of the cooling generator and a longitudinal direction of the heat dissipation unit may not be parallel.

According to an embodiment of the present invention, the heat dissipation unit and the cooling generator may be coupled through a coupling member disposed in a region where the cooling generator and the heat dissipation unit do not overlap.

According to an embodiment of the present invention, the cooling medium accommodating unit may include a contact portion including a contact surface that is thermally coupled to the cooling medium and an extending portion extending from the contact portion and at which the cooling generator is disposed, the extending portion may extend in a direction that intersects the longitudinal direction of the cooling medium, and the longitudinal direction of the cooling generator and the direction in which the extending portion extends may be the same.

An embodiment of the present invention provides a cooling method using a medical cooling device including a cooling medium, a cooling generator, and a cooling medium accommodating unit, the cooling method including supplying cooling energy to the cooling medium by the cooling generator and cooling a target region through thermal contact between the cooling medium and the target region, wherein a center-of-cooling-power region is disposed in a region where the cooling medium and the cooling medium accommodating unit overlap and has a center of cooling power which is a center with respect to thermal conductivity of the center-of-cooling-power region, a distance from a front end of the cooling medium to the center of cooling power is less than or equal to 30 mm, and the cooling medium is thermally connected to the cooling generator through the cooling medium accommodating unit that has one surface to which the cooling generator is attached.

According to an embodiment of the present invention, the cooling method may further include transferring a medicinal fluid, which is stored outside the center-of-cooling-power region, to the cooled target region.

According to an embodiment of the present invention, the center-of-cooling-power region may be disposed on an extension line that extends in a longitudinal direction of the cooling medium from a center of the region where the cooling medium and the cooling medium accommodating unit overlap, and a position of the center-of-cooling-power region may be determined by a center-of-cooling-power parameter of the cooling medium.

According to an embodiment of the present invention, the center of cooling power of the center-of-cooling-power region may be the center of the region where the cooling medium and the cooling medium accommodating unit overlap, and a length of the cooling medium may be a length within ten times a distance from a lower end of the cooling medium to the center of cooling power.

According to an embodiment of the present invention, the medical cooling device may further include a heat dissipation unit configured to dissipate heat of the cooling generator, and a longitudinal direction of the cooling generator and a longitudinal direction of the heat dissipation unit may not be parallel.

According to an embodiment of the present invention, the heat dissipation unit and the cooling generator may be coupled through a coupling member disposed in a region where the cooling generator and the heat dissipation unit do not overlap.

Advantageous Effects

By supplying intensive cooling energy to a cooling medium that comes in contact with a treatment site and performs cooling, a medical cooling device according to embodiments of the present invention can perform rapid cooling action. Also, by setting a cooling temperature range differently for each step, a medical cooling method according to embodiments of the present invention can minimize the extent to which a patient feels a change in temperature during a cooling process.

MODES OF THE INVENTION

Figure 1:
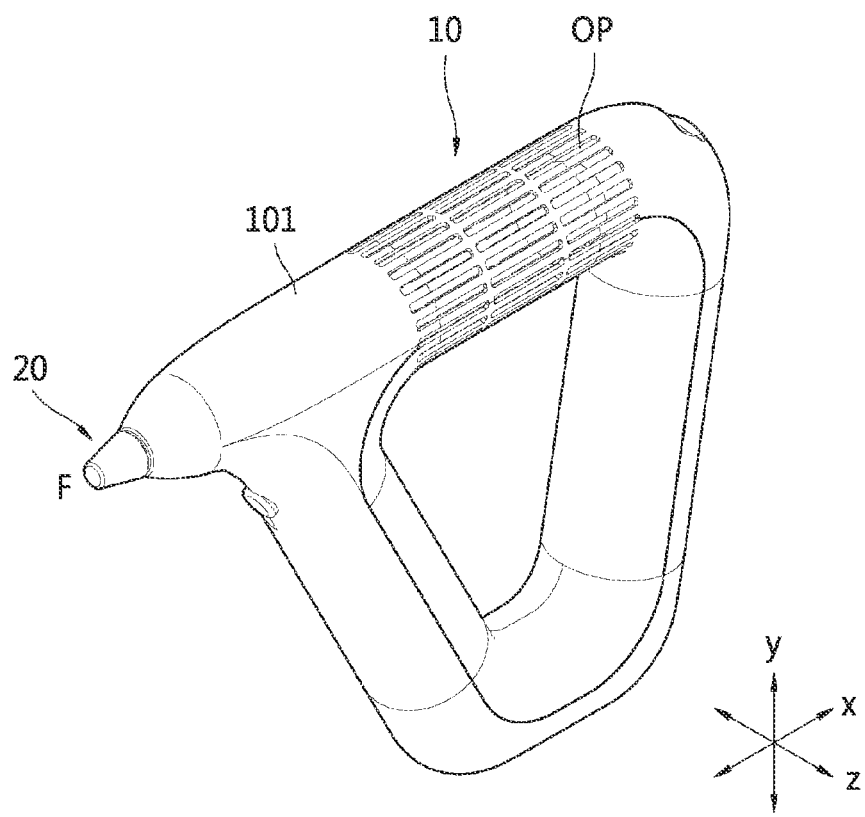
FIGS. 1 to 7 are views for describing a structure of a medical cooling device having a cooling function.

The present invention may be modified in various ways and have various embodiments. Hereinafter, specific embodiments which are illustrated in the drawings will be described in detail. The above-mentioned objectives, features, and advantages of the present invention will become more apparent from the following detailed description related to the accompanying drawings. However, the present invention is not limited to the embodiments disclosed below and may be implemented in various forms.

Hereinafter, embodiments of the present invention will be described in detail with reference to the accompanying drawings, In principle, like reference numerals refer to like elements throughout. Also, elements having the same function within the scope of the same idea shown in the drawings of each embodiment will be described using the same reference numerals, and redundant description thereof will be omitted.

In the following embodiments, ordinals (e.g., first and second) used in the description process of the present specification are merely identification symbols for distinguishing one element from another element.

In the following embodiments, a singular expression includes a plural expression unless the context clearly indicates otherwise.

In the following embodiments, terms such as "include" or "have" designate that features or elements described herein exist and do not preclude the possibility of adding one or more other features or elements in advance.

In the following embodiments, when a part such as a film, a region, or an element is described as being on or above another part, this not only includes a case in which the part is directly on the other part, but also includes a case in which still another film, region, element, or the like is interposed therebetween.

In the drawings, sizes of elements may have been exaggerated or reduced for convenience of description. For example, the size and thickness of each element shown in the drawings are arbitrarily shown for convenience of description, and the present invention is not necessarily limited thereto.

When a certain embodiment may be implemented differently, a specific process may be performed in an order different from a described order. For example, two processes described in succession may be performed substantially concurrently or performed in the reverse order.

In the following embodiments, when films, layers, regions, elements or the like are described as being connected, this not only includes a case in which the films, layers, regions, elements or the like are directly connected but also includes a case in which the films, layers, regions, elements or the like are indirectly connected with other films, layers, regions, elements or the like interposed therebetween. For example, in the present specification, when films, layers, regions, elements or the like are described as being electrically connected, this not only includes a case in which the films, layers, regions, elements or the like are directly electrically connected, but also includes a case in which the films, layers, regions, elements or the like are indirectly electrically connected with other films, layers, regions, elements or the like interposed therebetween.

1. Structures of Medical Cooling System and Medical Cooling Device

FIGS. 1 to 7 are views for describing a structure of a medical cooling device having a cooling function.

Figure 2:
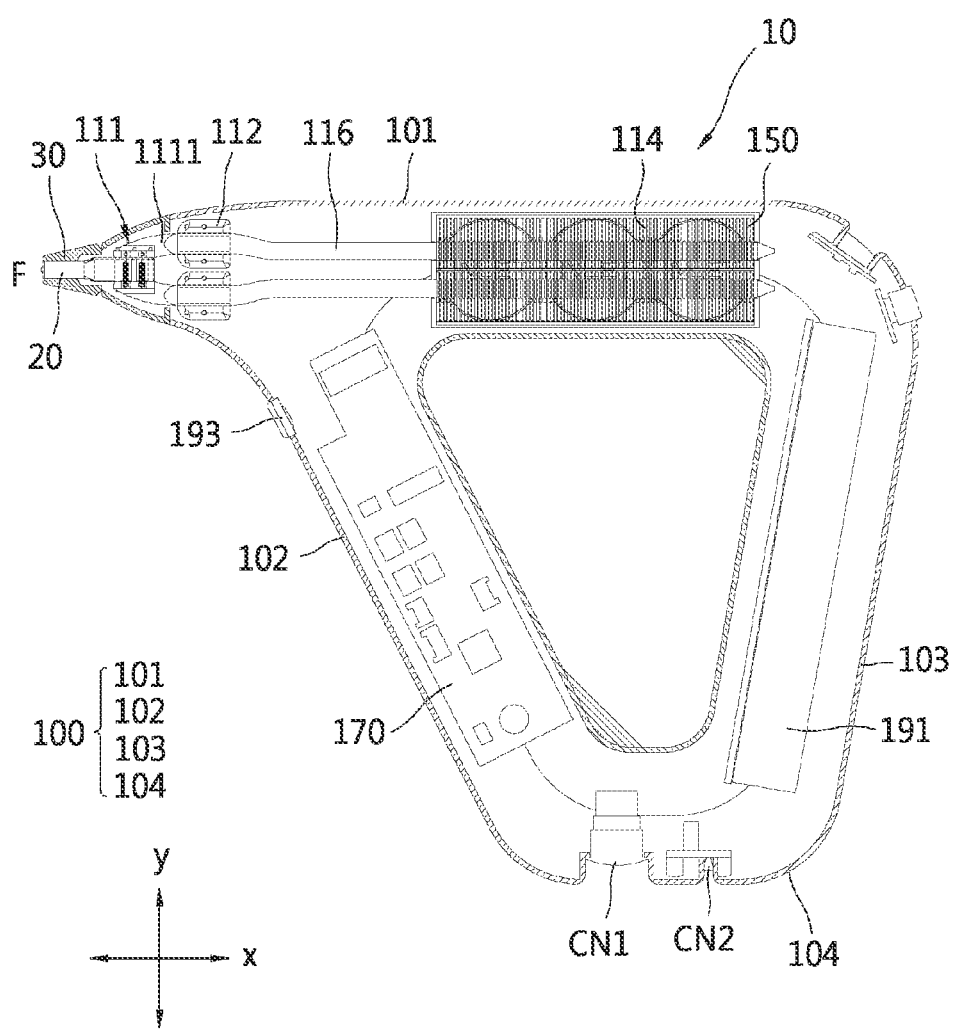

FIG. 1 is a view for describing a medical cooling system and a medical cooling device that have a cooling function, and FIG. 2 is a view illustrating an internal structure of a medical cooling system 1 of FIG. 1.

Referring to FIGS. 1 and 2, a medical cooling system 1 according to an example of the present disclosure may include a medical cooling device 10 and a cooling medium 20 accommodated in the medical cooling device 10.

The medical cooling system 1 according to the examples of the present disclosure may be configured to cool the cooling medium 20 accommodated in the medical cooling device 10 and then to cool an object thermally coupled to the cooling medium 20, by the operation of the medical cooling device 10. Here, thermal coupling with the object by the cooling medium 20 may include being in indirect contact or non-contact with the object, in additional to being in direct and physical contact with the object. The medical cooling system 1 according to the examples of the present disclosure may perform cooling anesthesia, cooling sterilization, cooling treatment, and the like by paralyzing nerves of a portion to be treated, i.e., a target portion by cooling such a target portion. In addition, the medical cooling system 1 may accommodate a medicine or drug in the cooling medium 20, and at the same time, may adjust a temperature of the medicine or drug independently of a temperature of the cooling medium 20, such that the disinfectant is discharged on or the medicine is injected into the target portion, while the target portion is anesthetized.

In the present disclosure, a portion to be anesthetized using the medical cooling system 1 may be any portions of a living body, for example, nerves, skin, eyes, gums, and the like. Hereinafter, the medical cooling system 1 will be described with connection with the eye for the convenience of explanation, but the present disclosure is not limited thereto.

In addition, the medical cooling system 1 may be applied not only to the anesthesia using cooling, but also to cases where hemostasis is required, antibiosis is required, skin portions such as dots, warts, and corns are removed, and local anesthesia is required for a relatively short time period in a small-scale laser treatment for hair removing, peeling, Botox therapy and so forth.

First, the medical cooling device 10 will be described. The medical cooling device 10 according to an embodiment of the present invention may include a main body portion 100, a cooling medium accommodating unit 111, a cooling generator 113, a heat dissipation unit 114, and an air blower 150.

The main body portion 100 forms an exterior of the medical cooling device 10, and other elements are accommodated therein. The main body portion 100 may include an opening op formed at one side so that a portion of the cooling medium 20 accommodated in the medical cooling device 10 may be exposed to the outside. The main body portion 100 may be formed as an elongated body or a non-elongated body. In the present specification, the elongated body, which has a structure in which the main body portion 100 is long in a longitudinal direction (x-direction), refers to a structure including one end portion in which a cooling medium is accommodated and the other end portion disposed opposite the one end portion. On the other hand, the non-elongated body refers to any structure other than the elongated body. Specifically, the non-elongated body refers to a structure that only includes one end portion in which a cooling medium is accommodated or includes two or more end portions. Here, an end portion refers to a portion in which one region of the main body portion 100 is no longer connected to another region.

Any of the elongated body and the non-elongated body may be applied to the main body portion 100 of the medical cooling device 10 according to embodiments of the present invention. However, hereinafter, for convenience of description, a case in which the medical cooling device 10 of the present invention includes the main body portion 100 formed as a non-elongated body will be mainly described.

FIGS. 3 to 7 are views illustrating various embodiments of the main body portion 100 of FIG. 1.

Referring to FIGS. 1 to 7, the medical cooling device 10 according to still another embodiment of the present invention may include the main body portion 100 formed as a non-elongated body. The non-elongated body may include a polygonal structure or a curved structure, and the polygonal structure or curved structure may be configured as an open type or configured as a closed type.

Figure 3:
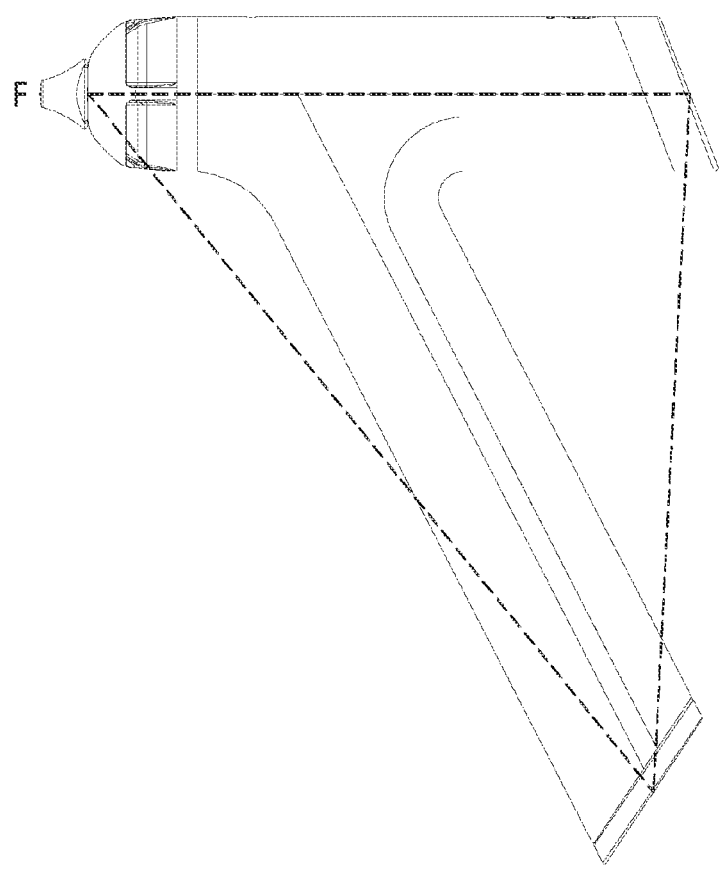
Figure 4:
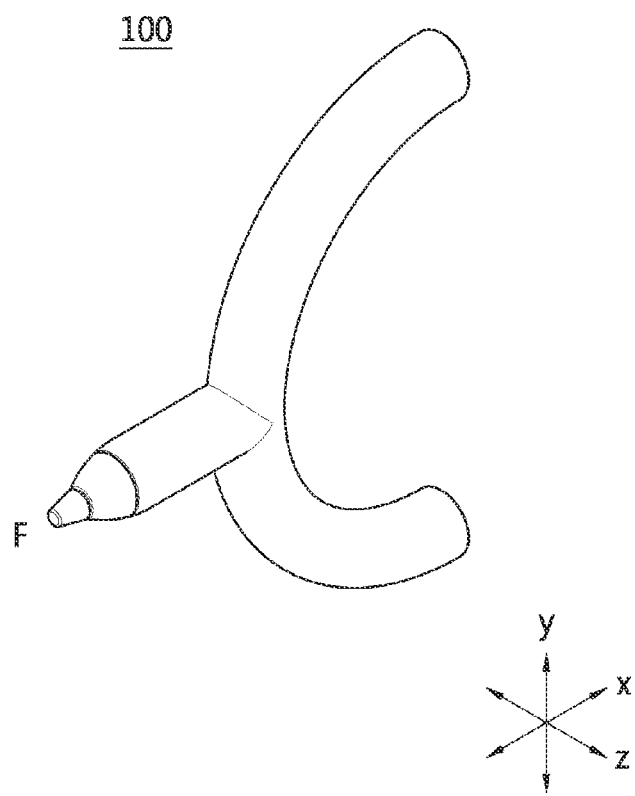
Figure 5:
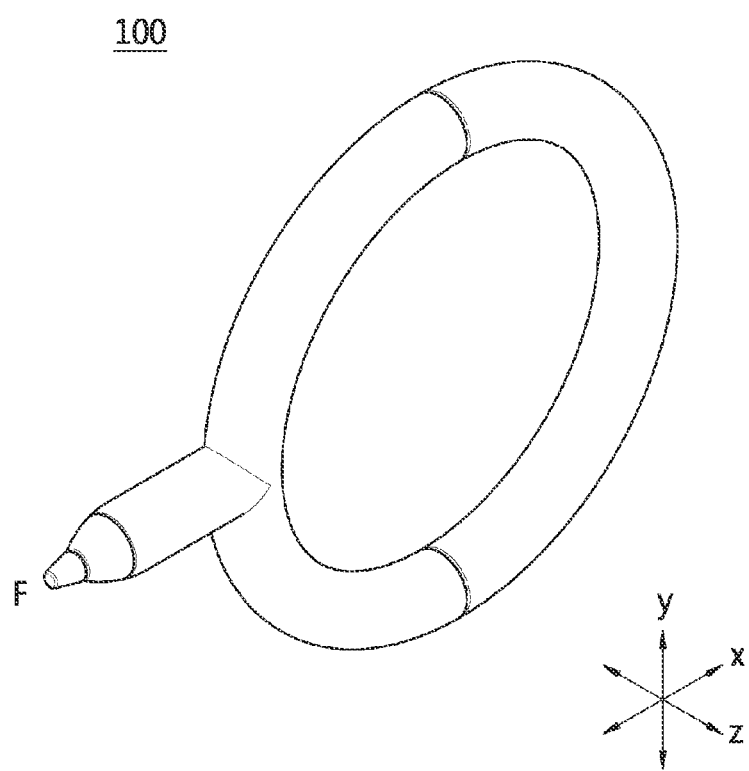

In the present specification, as in the embodiment illustrated in FIG. 3, the main body portion 100 having an open-type structure includes a front end portion F in which the cooling medium 20 is accommodated to face a target region and one or more end portions disposed at positions different from a position of the front end portion F. As illustrated in FIG. 3, the open-type structure may be formed as a polygonal structure, more specifically, an open-type triangular structure, or may be formed as an open-type curved structure as illustrated in FIG. 4.

Meanwhile, as in the embodiment illustrated in FIG. 1, the main body portion 100 having a closed-type structure includes the front end portion F in which the cooling medium 20 is accommodated to face a target region but, since portions other than the front end portion F are connected, does not further include another end portion. As in the embodiment illustrated in FIG. 5, the main body portion 100 may also be formed as a closed-type circular structure in which a front end portion F, at which a tip of the cooling medium 20 is disposed to protrude, is disposed at one point of the curved structure and one or more curved body portions are connected.

In one embodiment, referring to FIGS. 1 and 2, the main body portion 100 having a closed-type structure may be formed as a quadrilateral structure, and the front end portion F at which the tip of the cooling medium 20 is disposed to protrude may be disposed at one corner among the corners of the quadrilateral structure. The main body portion 100 having a closed-type structure may be formed as a closed-type structure in which a plurality of body portions 101, 102, 103, and 104 are connected. As compared to the main body portion 100 having an open-type structure, the main body portion 100 having a closed-type structure may secure a wider internal space and accommodate a high-capacity battery and may be designed so that a sufficient space is also secured for a control unit 170. Thus, the main body portion 100 having a closed-type structure may have an advantage in terms of heat. Here, the medical cooling device 10 may further include an input unit 193 configured to generate an input signal according to an external input.

For example, as illustrated in FIG. 2, the main body portion 100 may include a first body portion 101, a second body portion 102, a third body portion 103, and a fourth body portion 104 connected to each other. Here, in the first body portion 101, major elements for performing the cooling function, such as the cooling medium accommodating unit 111, the cooling generator 113, the heat dissipation unit 114, and the air blower 150, may be disposed. Also, in the first body portion 101, a plurality of openings OP configured to supply an external fluid to the heat dissipation unit 114 and discharge a fluid that passed through the heat dissipation unit 114 may be formed.

The control unit 170 may be disposed in the second body portion 102, and a power supply unit 191 including a battery that may be charged by wire or wirelessly or replaced may be disposed in the third body portion 103. In the fourth body portion 104, connection terminals CN1 and CN2 that are configured to connect the second body portion 102 and the third body portion 103 and are necessary for charging or communication may be disposed. However, the technical idea of the present invention is not limited thereto, and of course, the power supply unit 191 may be disposed in the second body portion 102, and the control unit 170 may be disposed in the third body portion 103. Also, the connection terminals CN1 and CN2 may be disposed at a rear surface or the like of the third body portion 103. Such an arrangement structure may be implemented in various embodiments according to the shape of the main body portion 100.

Meanwhile, in the case of the closed-type curved structure, the first body portion 101, the second body portion 102, the third body portion 103, and the fourth body portion 104 that correspond to the closed-type quadrilateral structure may be gently curved and constitute a single body portion. In this way, the main body portion 100 may secure a wide internal space that accommodates the control unit, the power supply unit, and the elements for performing the cooling function such as the cooling medium accommodating unit 111, the cooling generator 113, the heat dissipation unit 114, and the air blower 150.

Figure 6:
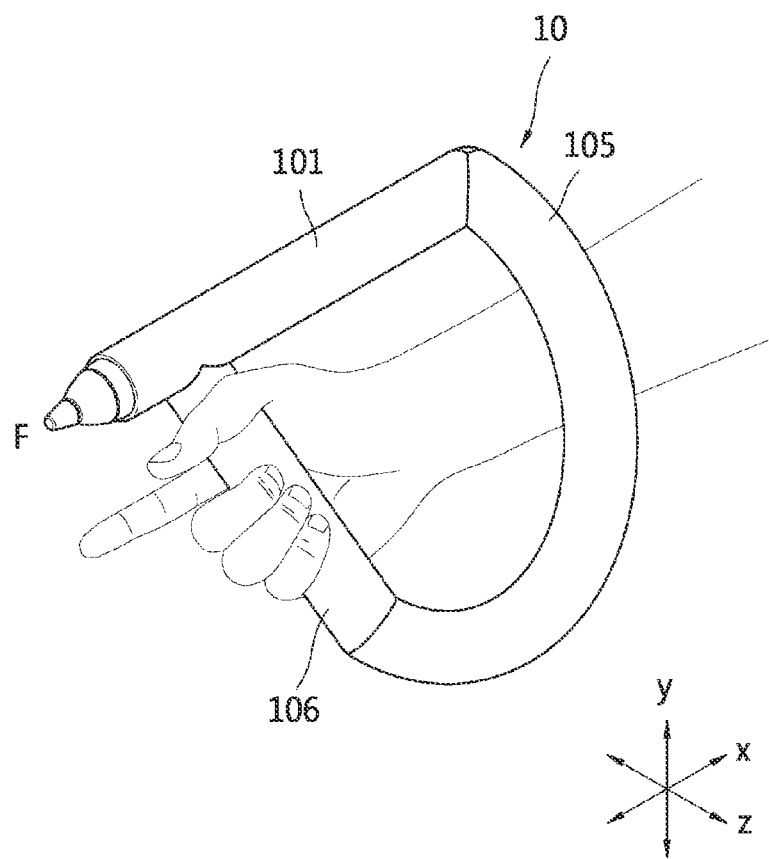
Figure 7:
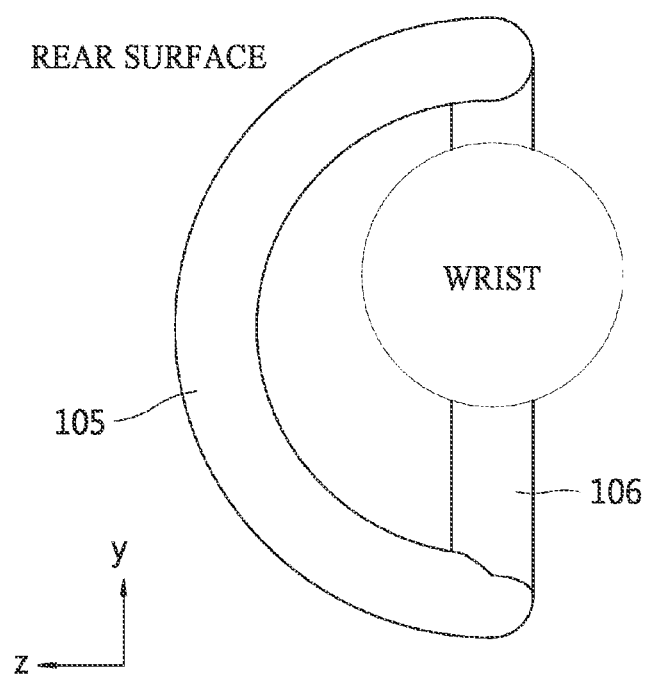

Referring to FIGS. 6 and 7, the medical cooling device 10 according to yet another embodiment may have a closed-type structure, but unlike the main body portion 100 of FIG. 1 that has the structure in which the plurality of body portions 101, 102, 103, and 104 are disposed to be coplanar (in the x-y plane), one body portion 105 may protrude in another direction (z-direction) that intersects the x-y plane. As illustrated in FIG. 6, the front end portion F at which the tip of the cooling medium 20 is disposed to protrude may be disposed in the first body portion 101, and a sixth body portion 106 connected to the first body portion 101 may serve as a handle that may be gripped by a user. Here, the main body portion 100 having a closed-type structure may include a fifth body portion 105 configured to connect the first body portion 101 and the sixth body portion 106. The fifth body portion 105 may be formed to be bent in another direction (z-direction) that intersects the x-y plane when viewed from the rear. In this way, the medical cooling device 10 according to yet another embodiment may be designed in an ergonomic structure that minimizes interference between the main body portion 100 and a user's wrist, and thus the convenience of use may be improved.

Meanwhile, in the medical cooling system according to an embodiment of the present invention, cooling may be performed through thermal coupling with a target region. The thermal coupling may include first thermal coupling with the target region through a contact method using the cooling medium 20 in the form of a cooling bar, which will be described below, or second thermal coupling with the target region through a non-contact method using a cryogen. Here, the second thermal coupling uses a non-contact method, and opening and closing of a valve connected to a cryogen spraying unit configured to spray the cryogen is controlled to control a cooling temperature. For example, the opening and closing may be controlled at least one time or more every 30 seconds to control the cooling temperature. Meanwhile, a cryogen storage unit may have a cryogen capacity of 10 grams or more. The medical cooling system according to an embodiment of the present invention may perform cooling using any of the first thermal coupling and the second thermal coupling, but hereinafter, a method using the first thermal coupling will be mainly described.

2. Lateral Cooling Structure and Method Thereof

Figure 8:
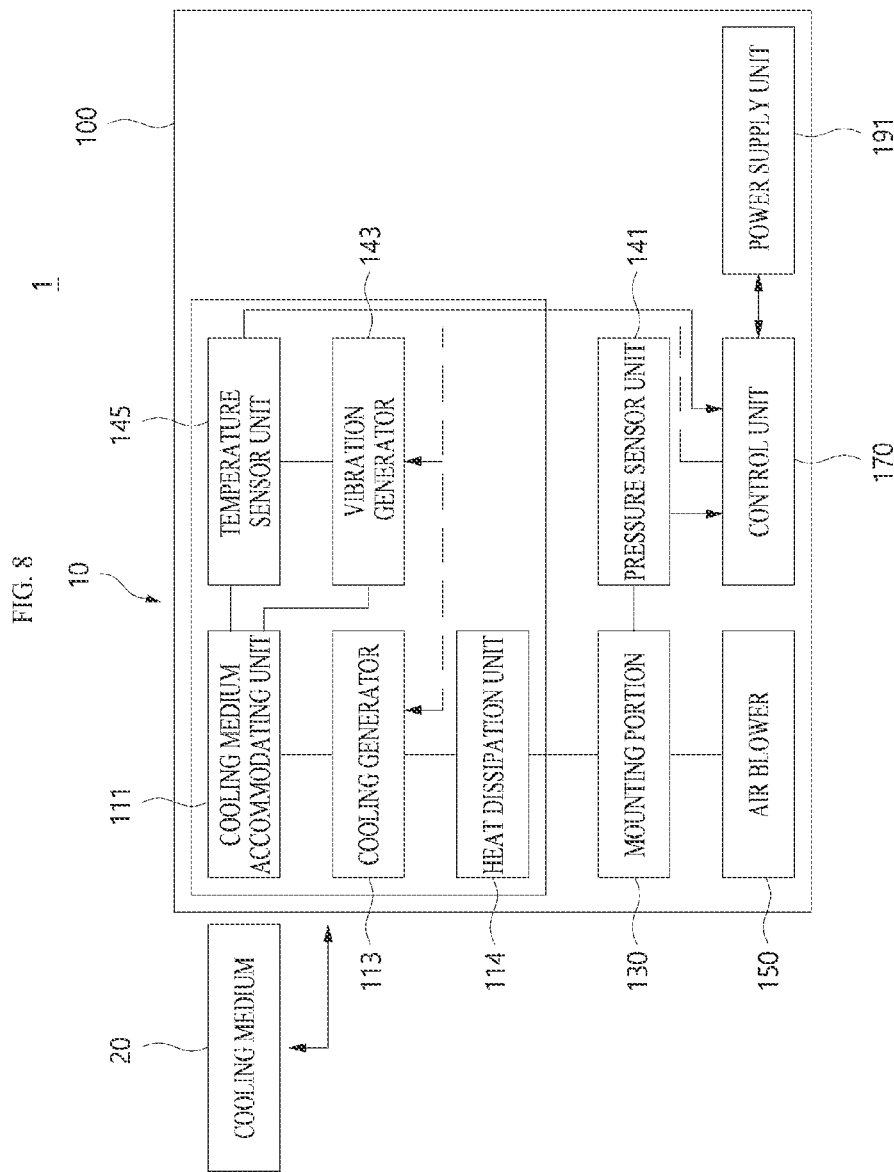
FIGS. 8 to 10 are views for describing a lateral cooling structure and a method thereof of the medical cooling device.
Figure 9:
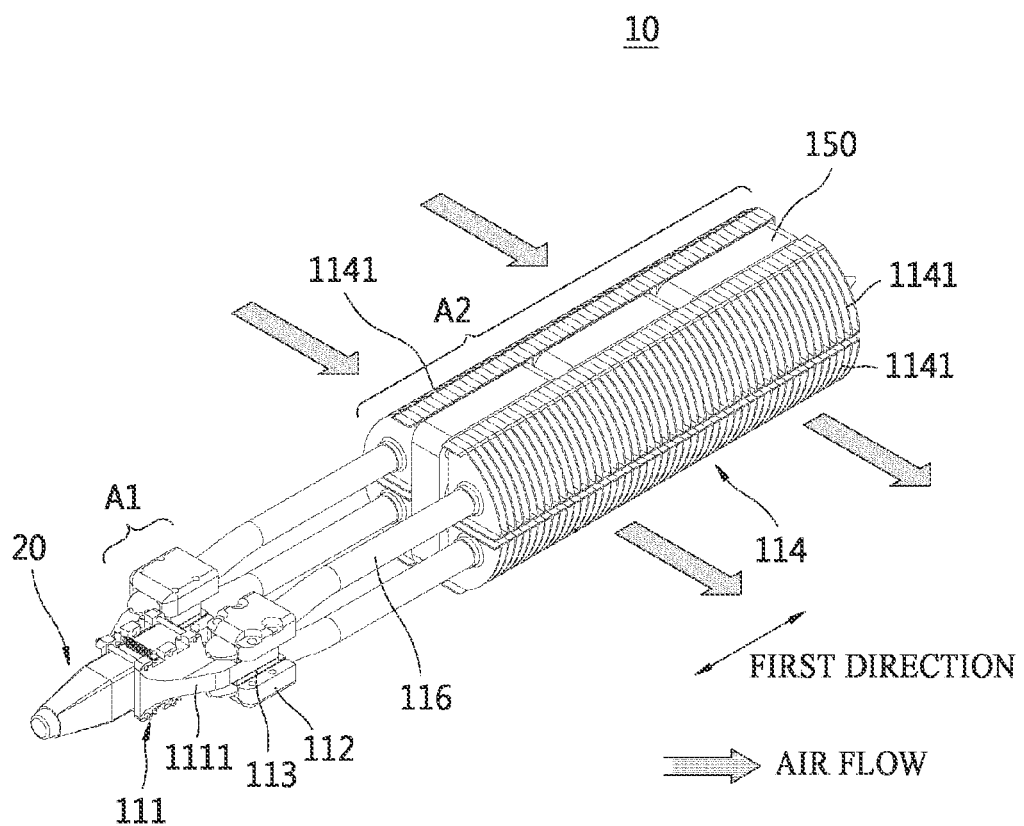
Figure 10:
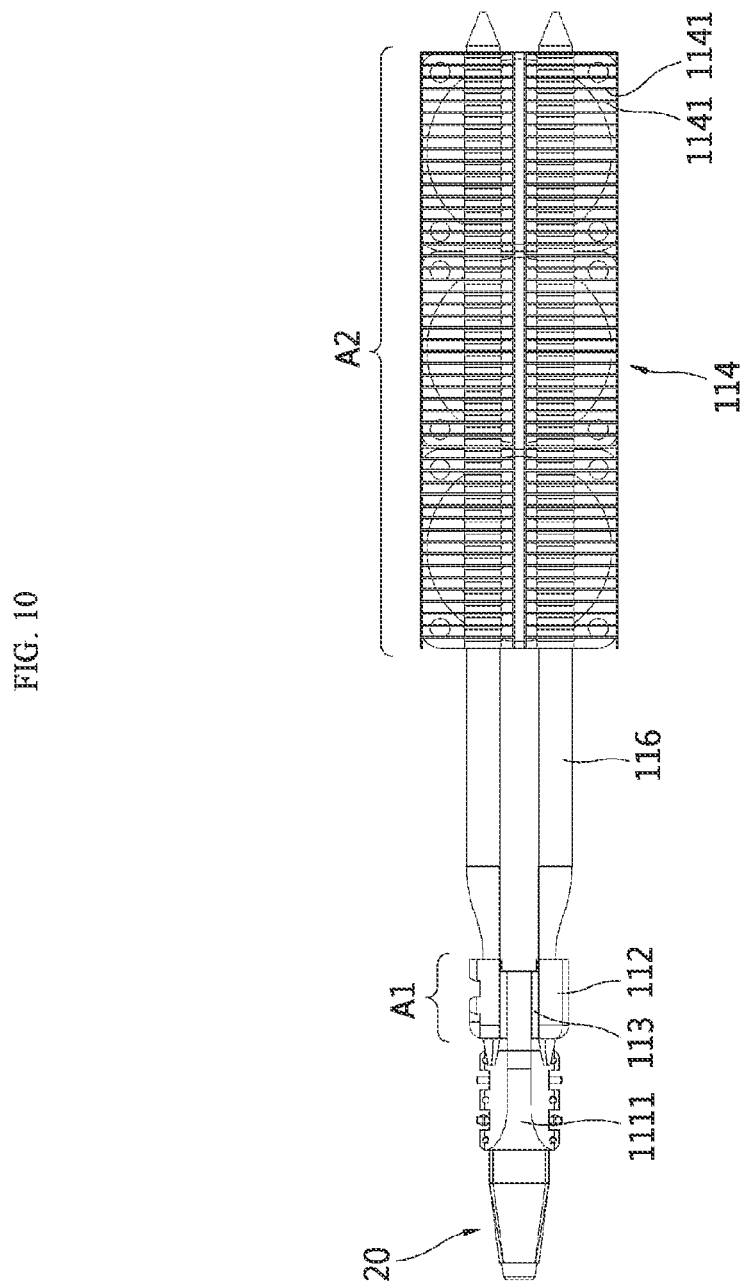

FIGS. 8 to 10 are views for describing a lateral cooling structure and a method thereof of a medical cooling device.

FIG. 8 is a block diagram of the medical cooling system 1 of FIG. 1, FIG. 9 is a view illustrating some of the elements disposed inside the main body portion 100 of the medical cooling device 10 of FIG. 1, and FIG. 10 is a lateral view of FIG. 9.

Referring to FIGS. 8 to 10, the cooling medium accommodating unit 111 may accommodate the cooling medium 20 and may be thermally coupled with the cooling medium 20 to transfer the cooling energy from the cooling generator 113 to the cooling medium 20. The cooling medium accommodating unit 111 may be made of metallic material having a high thermal conductivity to efficiently transfer the cooling energy. The cooling medium accommodating unit 111 may function as a cooling distributor for dispersing or distributing over a large surface or area of the cooling medium 20, the cooling energy collected from a relatively small surface or area of the cooling generator 113. With such a cooling distributing function, the cooling energy generated by the cooling generator 113 may be efficiently transferred to the cooling medium 20. The cooling medium accommodating unit 111 may include a plurality of split units 1111 that have a contact surface thermally coupled to the cooling medium 20.

Although not illustrated, the cooling medium accommodating unit 111 may include a lubricating member to easily accommodate the cooling medium 20 that is detachable. The lubricating member is formed on at least a portion of a contact surface of the cooling medium accommodating unit 111 and performs a lubricating function between the cooling medium accommodating unit 111 and the detachable cooling medium 20. The lubricating member performs a function of improving wear resistance in response to repeated replacement of the detachable cooling medium 20.

Meanwhile, the cooling generator 113 may be disposed on a surface, which is opposite to the contact surface of a plurality of split units 1111, and may supply the cooling energy to the cooling medium accommodating unit 111. In the present disclosure, the cooling energy is the concept opposite to the heat energy. In practice, cooling means lowering a temperature of an object through an endothermic reaction. However, for convenience of explanation, the cooling is defined as transferring the cooling energy to the object to lower the temperature thereof.

The cooling generator 113 may comprise any mechanism capable of supplying the cooling energy to the cooling medium accommodating unit 111 and may include one or more cooling elements capable of generating cooling energy. At least one cooling element may be disposed on the other surface of the plurality of split units 1111. The cooling element may adopt a thermodynamic cycle such as a stirling cooler or a vapor compression refrigeration cycle, a liquid evaporation, or a Joule-Thomson method using inflation gas to generate the cooling energy. Further, the cooling element may generate the cooling energy using liquid nitrogen or carbon dioxide, or may supply the cooling energy using a thermoelectric element such as a Peltier element. In the present disclosure, there is no limitation on the cooling element, but for convenience of explanation, the cooling generator 113 using the thermoelectric element will be described below.

When the current is applied to the thermoelectric element of the cooling generator 113, the surface of the thermoelectric element in contact with the cooling medium accommodating unit 111 may absorb the heat and the surface thereof in contact with the heat dissipation unit 114 may radiate the heat by the Peltier effect. The heat in a region where the cooling medium 20 and the object come into contact with each other may be transferred to the cooling generator 113 via the cooling medium 20 and the cooling medium accommodating unit 111 and then may be further transferred to the heat dissipation unit 114 to be radiated outside the device 10.

The heat dissipation unit 114 may be configured to discharge the heat emitted from the cooling generator 113 to the outside. The heat dissipation unit 114 may be also referred to as a heat sink, a heat emitting unit, a heat radiating unit, and so on. The heat dissipation unit 114 may be made of thermally conductive material to efficiently discharge the heat generated while the cooling generator 113 produces the cooling energy. The heat dissipation unit 114 may be formed of two or more heat dissipating members coupled to each other and may be divided into the number corresponding to the number of the plurality of split units 1111.

The heat dissipation unit 114 may be disposed to be spaced apart from the cooling generator 113 but may be thermally coupled to the cooling generator 113 and dissipate heat of the cooling generator 113 to the outside. The heat dissipation unit 114 may be disposed behind the cooling medium accommodating unit 111 and thermally coupled to the cooling generator 113 through a heat transfer medium 116. Meanwhile, the cooling medium accommodating unit 111 may partially overlap with the cooling medium 20. The cooling generator 113 is non-overlapping with the cooling medium 20 of the cooling medium accommodating unit 111 and may be disposed on a portion extending along the longitudinal direction (the first direction). The first region A1 of the heat transfer medium 116 may be coupled with the cooling medium accommodating unit 111 by interposing the cooling generator 113 through a coupling unit 112.

The heat dissipating unit 114 may include a plurality of heat dissipating sections, and the number of the heat dissipating sections may correspond to the number of the heat transfer medium 116. The plurality of heat dissipation fins 1141 of the heat dissipating unit 114 may extend in the longitudinal direction (the first direction) of the first body 101 to form two rows, and air blower 150 including at least one fan may be disposed in a space formed between the two rows.

The heat dissipation unit 114 may include a plurality of heat dissipation fins 1141, and the heat dissipation fins 1141 may be disposed to be spaced apart from each other in a longitudinal direction of the first body portion 101. Here, a predetermined number of heat dissipation fins 1141 may be disposed per unit length. For example, the number of heat dissipation fins 1141 per unit length may be in a numerical range of 0.5/mm to 1.5/mm. In a case in which the number of heat dissipation fins 1141 per unit length is less than 0.5/mm, a heat transfer area with a fluid is reduced and the heat dissipation efficiency is decreased. Also, in a case in which the number of heat dissipation fins 1141 per unit length exceeds 1.5/mm, a gap through which a fluid may flow is too narrow, and the heat dissipation efficiency is inevitably decreased. Therefore, by arranging the heat dissipation fins 1141 such that the number of heat dissipation fins 1141 per unit length is in the numerical range of 0.5/mm to 1.5/mm, the heat dissipation effect may be maximized.

The air blower 150 may be disposed inside the main body portion 100 and form a one-way air flow. The air blower 150 serves to suction in outside air, cool the heat dissipation unit 114 using the outside air, and then discharge the air. The air blower 150 may include a fan, but the present invention is not limited thereto, and of course, any device capable of generating a one-way air flow, such as a compression air tank and a blower, may be applied to the air blower 150.

Specifically, in a state in which the air blower 150 that consists of at least one or more fans is disposed between two heat dissipation fin columns in the medical cooling device 10, an air flow may be formed in a direction that is not parallel to the longitudinal direction of the first body portion 101. That is, the air blower 150 may form the air flow in a direction not parallel to the axial direction of the heat dissipating unit 114. More specifically, in the medical cooling device 10 may also form the air flow perpendicular to the longitudinal direction of the first body 101. By disposing the air blower 150 in the divided heat dissipating unit 114, a path through which the air flows may be formed over a significantly large area of the heat dissipation unit 114 with a relatively short distance, and thus greatly enhance the heat transfer between the heat dissipation fins 1141 and the air. Further, when the air blower 150 has the plurality of fans, an arranging direction of the plurality of fans and the axial direction of the heat dissipation unit 114 may be parallel with each other, and the arranging direction of fans may intersect the blowing direction of the fans.

The heat transfer medium 116 may connect the cooling generator 113 and the heat dissipation unit 114 to transfer the heat of the cooling generator 113 to the heat dissipation unit 114. The heat transfer medium 116 may comprise a heat pipe or a vapor chamber and may include a pipe body and phase change material (PCM) provided inside the pipe body. The pipe body may be made of material having the high thermal conductivity so as to effectively transfer the heat from the cooling generator 113 that is in contact with the heat transfer medium 116 to the PCM therein. The PCM is the material that is able to store a great amount of thermal energy or release the stored thermal energy through the phase change. Further, the PCM has a unique heat storage capacity.

Alternatively, the heat transfer medium 116 may comprise a pipe including a fluid that forcibly flows or circulates therein by using a pump or the like. In other words, the heat transfer medium 116 may have the first region A1 which is thermally coupled with the second surface 113B of the cooling generator 113 to absorb the heat energy from the cooling generator 113. Further, the heat transfer medium 116 may have a second region A2 which extends in the longitudinal direction (the first direction) of the cooling medium accommodating unit 111 from the first region A1 and is thermally coupled to the heat dissipation unit 114. Thus, the heat transfer medium 116 may emit the heat energy absorbed at the first region A1 via the second region A2. Here, the second region A2 of the heat transfer medium 116 may not overlap with the accommodating unit 111.

The medical cooling device 10 according to the present disclosure may use the heat transfer medium 116 containing the phase change material to effectively transfer the heat generated from the cooling generator 113 to the heat dissipation unit 114, in order to be radiated the outside of the device 10. That is, the amount of cooling energy per unit area generated at the cooling generator 113 (i.e., the thermoelectric element) may be greatly increased when the heat transfer medium 116 is used, because of superior heat transfer performance per unit area of the heat transfer medium 116 compared to simple copper. Accordingly, the cooling medium accommodating unit 111 may effectively transfer the significant amount of the cooling energy to the cooling medium 20 even via a relatively small contact area with the cooling medium 20, and thus a degree of freedom with respect to the length of the cooling medium 20 may be increased.

Meanwhile, the medical cooling device 10 may further include a pressure sensor unit 141 configured to detect a pressure applied when the cooling medium 20 comes in contact with a treatment site of a subject and generate a pressure signal. The pressure sensor unit 141 may be disposed on another element capable of detecting a pressure due to contact with the cooling medium accommodating unit 111 or the cooling medium 20 and may detect a pressure applied from the cooling medium 20.

The medical cooling device 10 may further include a vibration generator 143 configured to generate vibration through the cooling medium 20. The vibration generator 143 serves to generate vibration while cooling is performed using the cooling medium 20 or a drug is injected and reduce pain of a subject receiving treatment. By generating vibration in the cooling medium accommodating unit 111 accommodating the cooling medium 20, the vibration generator 143 may transmit vibration through the cooling medium 20.

Meanwhile, the medical cooling device 10 may further include a temperature sensor unit 145 configured to detect a temperature of the cooling medium 20 or the cooling medium accommodating unit 111. The temperature sensor unit 145 may be connected to the cooling medium accommodating unit 111 and detect a temperature thereof or may be disposed at a position that comes in direct contact with the cooling medium 20 and detect a temperature of the cooling medium 20. Also, in a case in which the cooling medium 20 is configured to be replaceable, the temperature sensor unit 145 configured to measure the temperature of the cooling medium 20 may be configured as a non-contact-type temperature sensor, e.g., an infrared sensor.

3. Cooling and Heat-Dissipating Structure

Figure 11:
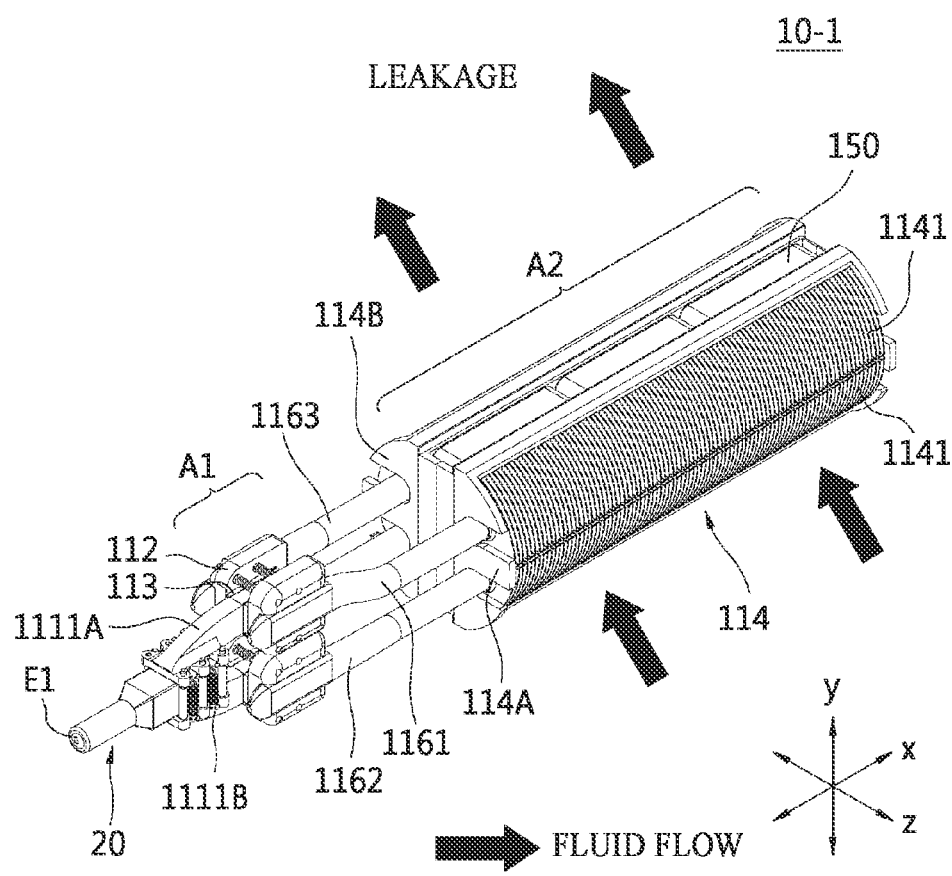
FIGS. 11 to 13 are views for describing a balanced cooling and heat-dissipating structure of the medical cooling device.
Figure 12:
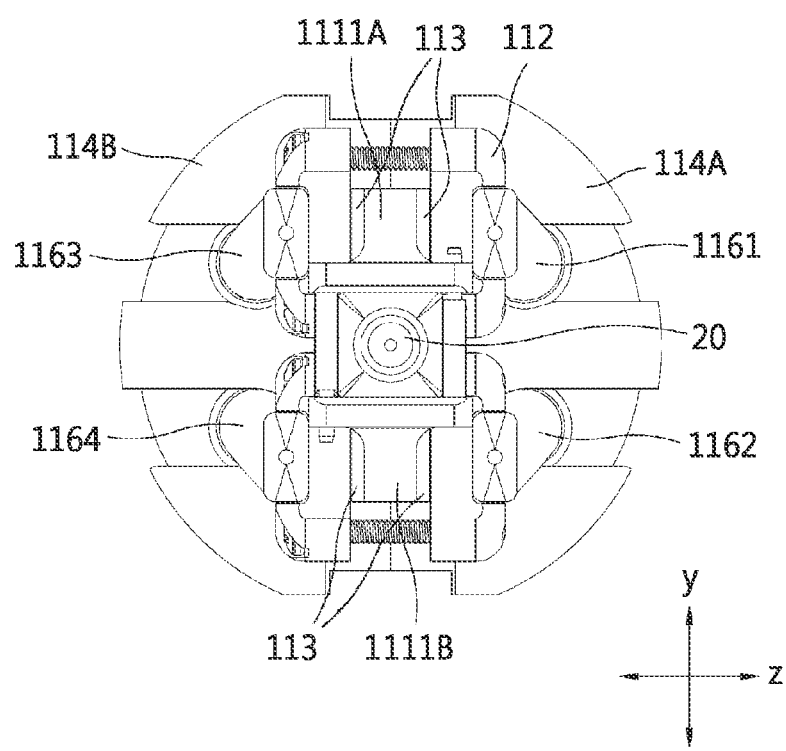
Figure 13:
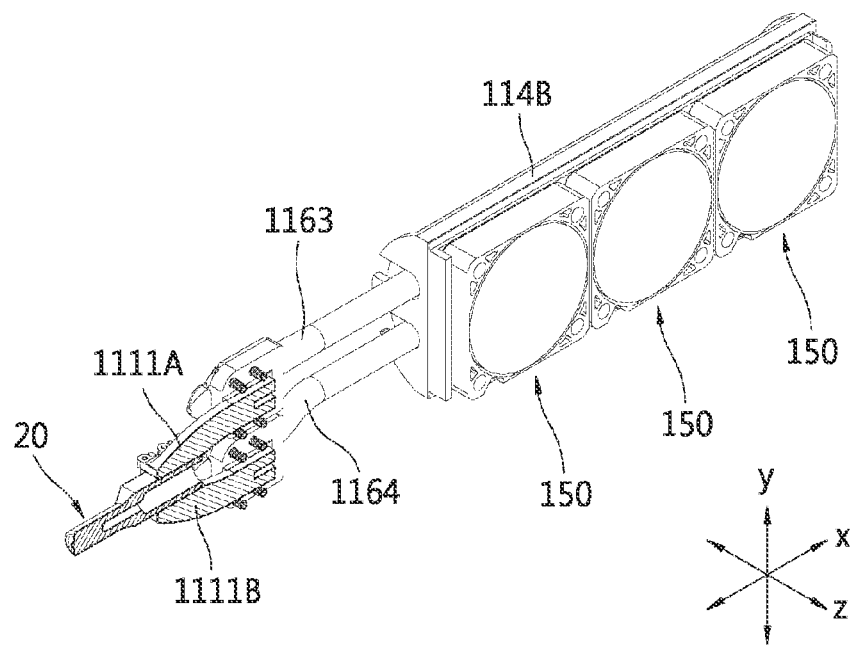

FIGS. 11 to 13 are views for describing a balanced cooling and heat-dissipating structure of the medical cooling device.

According to the present invention, for a balanced cooling and heat dissipating structure, it is preferable to have an overall symmetrical structure. The cooling medium accommodating unit 111 is provided symmetrically with the plurality of split units 1111 having a contact surface in thermal contact with the cooling medium 20. In addition, a plurality of cooling generators 113 such as thermoelectric elements are provided corresponding to the split units 1111 having symmetrical structure. In addition, the heat transfer medium 116 such as a heat pipe corresponding to the cooling generator 113 may be configured to be symmetrical.

The heat transfer medium 116 is coupled to the heat dissipation unit 114, and the heat dissipation unit 114 may include a plurality of heat dissipating sections. More specifically, the heat dissipation unit 114 may include a heat dissipating section disposed at the inlet side of an air blower and a heat dissipating section disposed at the outlet side of the air blower.

In corresponding to a plurality of symmetrically configured heat transfer medium unit and a plurality of symmetrically configured heat dissipating sections, it is preferable that the plurality of heat transfer medium units corresponding to the split unit are configured to be symmetrically coupled to the inlet side heat dissipating section and the outlet side heat dissipating section.

For the heat dissipation unit, even if the physical structure is symmetrical, a heat dissipating effect may be asymmetric. That is, for the heat dissipating effect of the heat dissipation unit 114, the heat dissipating effect of the inlet side heat dissipation section through which air is introduced and the dissipating effect of the outlet side heat dissipation section through which air is discharged are different. According to the present invention, the heat transfer medium unit corresponding to one split unit is configured to be coupled to the air-inlet side heat dissipating section and the air-outlet side heat dissipating section, respectively, so that the cooling generator can be dissipated in a balanced and efficient manner by using a heat dissipating section with asymmetrical heat dissipating effect.

Specifically, referring to FIGS. 11 to 13, a medical cooling device 10-1 may include a cooling medium accommodating unit 111 thermally coupled to a cooling medium 20. The cooling medium accommodating unit 111 may include a plurality of split units 1111A and 1111B that have a contact surface that thermally comes in contact with the cooling medium 20. In one embodiment, the cooling medium accommodating unit 111 may include a first split unit 1111A and a second split unit 1111B that have the cooling medium 20 interposed therebetween and are disposed to be symmetrical in one direction (y-direction in FIG. 13).

As illustrated in FIG. 13, the first split unit 1111A and the second split unit 1111B may partially overlap with the cooling medium 20. Here, the cooling generator 113 may be disposed at portions of the first split unit 1111A and the second split unit 1111B that do not overlap with the cooling medium 20 and extend in the longitudinal direction (x-direction). The first split unit 1111A and the second split unit 1111B are disposed to be symmetrical and are formed to have the same structure. Thus, hereinafter, description will be given on the basis of the first split unit 1111A.

In one embodiment, two cooling generators 113 may be disposed to correspond to a single first split unit 1111A. For example, as illustrated in FIG. 12, the cooling generators 113 may be disposed to be symmetrical in the z-direction with respect to the first split unit 1111A, and each cooling generator 113 may be connected to the heat dissipation unit 114 through the heat transfer medium 116 and thus heat transfer may occur. The heat transfer medium 116 performs a function of transmitting heat of the cooling generator 113 to the heat dissipation unit 114 and dissipating heat from the cooling generator 113.

Meanwhile, the medical cooling device 10-1 may include an air blower 150 that consists of a plurality of fans. The air blower 150 may generate a fluid flow in a first direction (z-direction). Here, the first direction (z-direction) may intersect a longitudinal direction of the heat dissipation unit 114 (x-direction). Since the heat dissipation unit 114 has a structure extending in the longitudinal direction (x-direction), a width thereof in the first direction (z-direction) may be smaller than a length thereof in the longitudinal direction (x-direction). Therefore, since a fluid is introduced through a wide area of the heat dissipation unit 114 and then leaks through a distance shorter than a distance of the wide area, the heat dissipation efficiency of the heat dissipation unit 114 may be maximized. Here, the fans constituting the air blower 150 may each have a thickness of 25 mm or less to minimize a fluid passage distance in the heat dissipation unit 114 in the first direction (z-direction). In this way, the heat dissipation efficiency of the heat dissipation unit 114 may be maximized.

Meanwhile, in the case in which the air blower 150 includes a plurality of fans, the plurality of fans may generate a fluid flow in the same direction, but in another embodiment, the plurality of fans may generate fluid flows in opposite directions. For example, in a case in which the air blower 150 includes four fans, when two fans generate a fluid flow in the z-direction, the other two fans may generate a fluid flow in −z-direction. Through this air blowing method, the medical cooling device 10-1 may dissipate heat from the cooling generator 113 in a balanced and efficient manner. However, hereinafter, for convenience of description, a case in which the plurality of fans generate a fluid flow in the same direction will be described.

The heat dissipation unit 114 may consist of a plurality of heat dissipating units. In one embodiment, the heat dissipation unit 114 may include a plurality of heat dissipating units that correspond to the number of heat transfer media 116. In another embodiment, the heat dissipation unit 114 may include a first heat dissipating unit 114A and a second heat dissipating unit 114B that are disposed to be symmetrical in the first direction (z-direction) with respect to the air blower 150. In a case in which the air blower 150 generates a fluid flow in the first direction (z-direction), the first heat dissipating unit 114A may correspond to an introduction-side heat dissipating unit, and the second heat dissipating unit 114B may correspond to a leakage-side heat dissipating unit. However, since positions of the introduction-side heat dissipating unit and the leakage-side heat dissipating unit may vary according to a direction of a fluid flow generated by the air blower 150, the present invention is not limited by directions of fluid flows illustrated in the drawings.

As described above, even when the heat dissipation unit 114 has a physically symmetrical structure, the heat dissipation effect may be different in the first heat dissipating unit 114A, which is the introduction-side heat dissipating unit, and the second heat dissipating unit 114B, which is the leakage-side heat dissipating unit. Specifically, while a cold fluid from the outside continuously flows into the introduction-side heat dissipating unit, a fluid that is relatively hotter than the fluid from the outside passes through the leakage-side heat dissipating unit due to the heat transfer of the heat dissipation unit 114. Therefore, the heat dissipation effect of the introduction-side heat dissipating unit may be relatively greater than the heat dissipation effect of the leakage-side heat dissipating unit.

Here, the first split unit 1111A may be symmetrically connected to the first heat dissipating unit 114A and the second heat dissipating unit 114B by a plurality of heat transfer media 116. For example, in a state in which the first split unit 1111A is interposed between the cooling generators 113, the first split unit 1111A may be connected to the first heat dissipating unit 114A through a first heat transfer medium 1161 and connected to the second heat dissipating unit 114B through a third heat transfer medium 1163. Therefore, a single first split unit 1111A may be connected to both the first heat dissipating unit 114A and the second heat dissipating unit 114B which have asymmetrical heat dissipation effects, and in this way, balanced thermal coupling with the cooling medium 20 may be possible.

Likewise, the second split unit 1111B may also be connected to both the first heat dissipating unit 114A and the second heat dissipating unit 114B using a second heat transfer medium 1162 and a fourth heat transfer medium 1164. The cooling medium accommodating unit 111 may symmetrically transfer cooling energy to the cooling medium 20 using the first split unit 1111A and the second split unit 1111B which are disposed to be symmetrical. In this way, the cooling medium 20 may cool a target region in a balanced and efficient manner without deviations in the extent of cooling.

4. Cooling Medium and Cooling Tip Structure and Function Thereof

Figure 14:
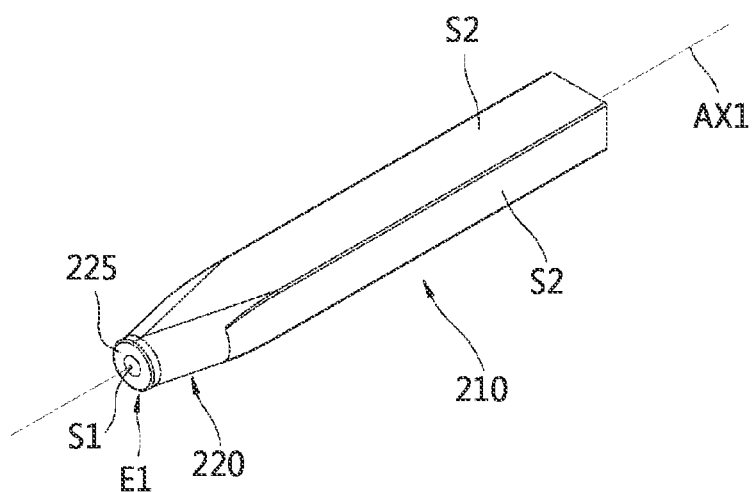
FIGS. 14 and 15 are views for describing an intensive cooling structure using a cooling medium.
Figure 15:
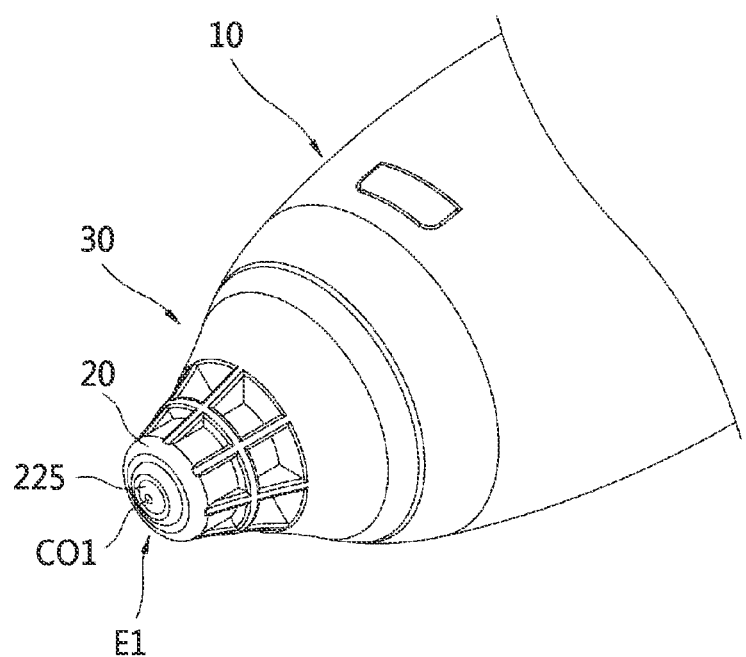

FIGS. 14 and 15 are views for describing an intensive cooling structure using a cooling medium. Hereinafter, the cooling medium 20 of the medical cooling system 1 will be described.

FIG. 14 is a perspective view illustrating the detachable cooling medium 20 according to an embodiment of the present invention, and FIG. 15 is a view illustrating a portion of the medical cooling device to describe an intensive cooling structure using the detachable cooling medium 20.

Basically, the detachable cooling medium 20 and the medical cooling system 1 including the same according to an embodiment of the present invention may collect the cooling energy in a large area via the cooling medium accommodating unit 111 comprising the single split unit 1111 or the plurality of split units 1111. Thus, a front end portion 225 of the detachable cooling medium 20, specifically a narrow area or region of the front end portion 225 may be further configured to concentrate the collected cooling energy thereon. This allows the medical cooling system 1 to perform the anesthesia by effectively cooling the target area. The detachable cooling medium 20 may be further configured to be easily separated from the medical cooling device 10 to minimize the risk of infection.

The function of the detachable cooling medium 20 is primarily to perform the cooling for the target area such as the eye. In the present disclosure, the cooling medium 20 may be the detachable cooling medium that is detachably installed to the medical cooling device 10 and is formed disposable. However, the scope of the present disclosure is not limited thereto, and the cooling medium 20 is a component that is accommodated in the medical cooling device 10 and may not necessarily be provided in a detachable manner. However, hereinafter, for convenience of description, the terms "cooling medium," "detachable cooling medium," and "disposable cooling medium" may be used interchangeably, and description will be given assuming that these terms all refer to the same element.

Referring to FIG. 14, the detachable cooling medium 20 may include an insertion region 210 and a non-insertion region 220. The detachable cooling medium 20 may be inserted into the cooling medium accommodating unit 111 of the medical cooling device 10 through the insertion region 210. In addition, the detachable cooling medium 20 may perform a cooling function by contacting the target area through the front end portion 225 provided in the non-insertion region 220.

The insertion region 210 may be inserted into the medical cooling device 10 more particularly the cooling medium accommodating unit 111 and may transfer the cooling energy delivered from the cooling medium accommodating unit 111 to the non-insertion region 220. The insertion region 210 may receive the cooling energy through an outer surface S2 that is in thermal contact with the cooling medium accommodating unit 111.

The non-insertion region 220 may not be inserted into the medical cooling device 10 and may have front end portion 225 provided at an end E1 and thermally contacting the target area. The non-insertion region 220 may extend along the axial direction AX1 from the insertion region 210 and may have a diameter gradually decreased into the end E1. That is, the non-insertion region 220 may be tapered when viewed in a section taken along the axial direction AX1.

The front end portion 225 provided at the end E1 of the non-insertion region 220 may come into contact with the target area such as the eyeball and may cool the target area by receiving the cooling energy generated by the cooling generator 113 from the insertion region 210. In an alternative aspect, the front end portion 225 may come into contact and cool the target area by delivering the heat of the target area to the medical cooling device 10.

Although a shape, specifically a sectional shape of the front end portion 225 is shown as being circular, the scope of the present disclosure is not limited thereto, and the front end portion 225 may be formed in various shapes with which the cooling may be efficiently performed while contacting the target are. In addition, an area S1 of the front end portion 225 may be equal to or smaller than an area of the target area. With such an area S1, the detachable cooling medium 20 may intensively cool the target area.

Meanwhile, the detachable cooling medium 20 may be made of material having the high thermal conductivity to effectively transfer the cooling energy from the medical cooling device 10 to the target area M. For example, the detachable cooling medium 20 may be made of gold (Au), silver (Ag), copper (Cu), aluminum (Al), and the like. Although the insertion region 210 and the non-insertion region 220 are shown as being formed integrally with each other, the insertion region 210 and the non-insertion region 220 may be manufactured as separate members and then be coupled with each other. In addition, the insertion region 210 and the non-insertion region 220 may be made of the same material, but may be made of different materials. Further, the front end portion 225 may be coated with material comprising a hydrophobic material to reduce formation of ice during cooling. Here, the insertion region 210 and the non-insertion region 220 of the detachable cooling medium 20 may serve as a kind of heat flux distributor.

Meanwhile, the length or structure of the cooling medium may be changed according to the target region, that is, a treatment or a treatment site. When the length of the cooling medium is lengthened for smooth contact with the target area, the detachable cooling medium may be implemented as a heat transfer medium such as a heat pipe. Through above structure, it is possible to minimize the temperature difference at the tip of the shape.

According to an embodiment, when the cooling medium is implemented as a disposable tip having a heat pipe structure, for example a heat pipe having thermal conductivity of 5000 W/m-K, a performance degradation can be minimized despite of the long shape.

In addition, since the heat pipe operates in a cooling or refrigeration environment, it is preferable to implement a heat pipe using a refrigerant operating at a temperature below the freezing point. For example, when ethylene glycol is used as the refrigerant, the freezing point of the refrigerant can be optimized corresponding to the cooling treatment site by adjusting the concentration of ethylene glycol. Of course, it is possible to optimize the freezing point by using various refrigerants other than ethylene glycol, such as ammonia or methanol which are heat pipe refrigerants suitable for the freezing point or lower. For example, the operating temperature range of the heat pipe may be a second temperature range, and as described below, may have a range of −90° C. to 0° C. or −50° C. to 0° C. depending on the purpose of the treatment.

Meanwhile, referring to FIG. 15, the detachable cooling medium 20 according to an embodiment of the present invention collects cooling energy through a wide area of the cooling medium accommodating unit 111, which includes a single split unit 1111 or a plurality of split units 1111, and concentrates the cooling energy to a narrow area of the front end portion 225 of the detachable cooling medium 20. Here, the detachable cooling medium 20 may include a cooling-concentrated portion CO1 that protrudes to the outside from a surface of the front end portion 225 in one region of the front end portion 225.

As described above, the detachable cooling medium 20 concentrates the cooling energy collected through the wide area to the narrow area of the front end portion 225, and particularly, since the detachable cooling medium 20 further includes the cooling-concentrated portion CO1 that has a structure protruding to the outside from the front end portion 225, the cooling energy may be further focused through the narrow area of the cooling-concentrated portion CO1. Also, since the cooling-concentrated portion CO1 has a structure protruding outward more than the front end portion 225, when an operator brings the front end portion 225 of the detachable cooling medium 20 into contact with a treatment site, the maximum pressure may be applied to a corresponding site in a target region through the protruding portion. Therefore, in this way, as compared to other regions of the front end portion 225, the cooling-concentrated portion CO1 may transfer the cooling energy at maximum to the corresponding site.

Here, a site in the target region that corresponds to the cooling-concentrated portion CO1 may coincide with an injection site. That is, by transferring the maximum cooling energy to a site in the target region in which injection occurs, the cooling-concentrated portion CO1 may more effectively anesthetize a site where pain actually occurs due to an injection needle.

To this end, in one embodiment, the cooling-concentrated portion CO1 may be formed as a protrusion disposed at the center of the front end portion 225. In FIG. 15, the cooling-concentrated portion CO1 is illustrated as being formed in the shape of a protrusion without a hole being formed in the front end portion 225 to allow an injection needle to pass therethrough. However, the present invention is not limited thereto, and in another embodiment, in a case in which the detachable cooling medium 20 is in the form of a cartridge that stores a medicinal fluid and then injects the medicinal fluid using an injection needle disposed inside the cooling medium 20, a through-hole through which the injection needle passes may be formed in the front end portion 225, and here, the center of the cooling-concentrated portion CO1 and the center of the injection needle may coincide. In other words, the cooling-concentrated portion CO1 may be formed due to a portion that is adjacent to and surrounds the through-hole through which the injection needle passes having a structure protruding outward more than other regions of the front end portion 225

Also, the cooling-concentrated portion CO1 may be formed in the shape of a protrusion of which a cross-sectional area decreases outward from the front end portion 225. However, the present invention is not limited thereto, and the cooling-concentrated portion CO1 may have a predetermined cross-sectional area in a protruding direction in which the cooling-concentrated portion CO1 protrudes outward. Also, a cross-section of the cooling-concentrated portion CO1 in the protruding direction may have various shapes, e.g., any one of a quadrangular shape, a triangular shape, and a circular shape.

As described above, since the detachable cooling medium 20 according to an embodiment of the present invention has the cooling-concentrated portion CO1 having the protrusion structure formed at the front end portion 225, the maximum cooling energy may be concentrated and delivered to the injection site, and thus a cryoanesthetic effect may be maximized.

5. Center-of-Cooling-Power Structure

FIGS. 16 to 20 are views for describing another embodiment of a medical cooling system having a cooling function.

Figure 16:
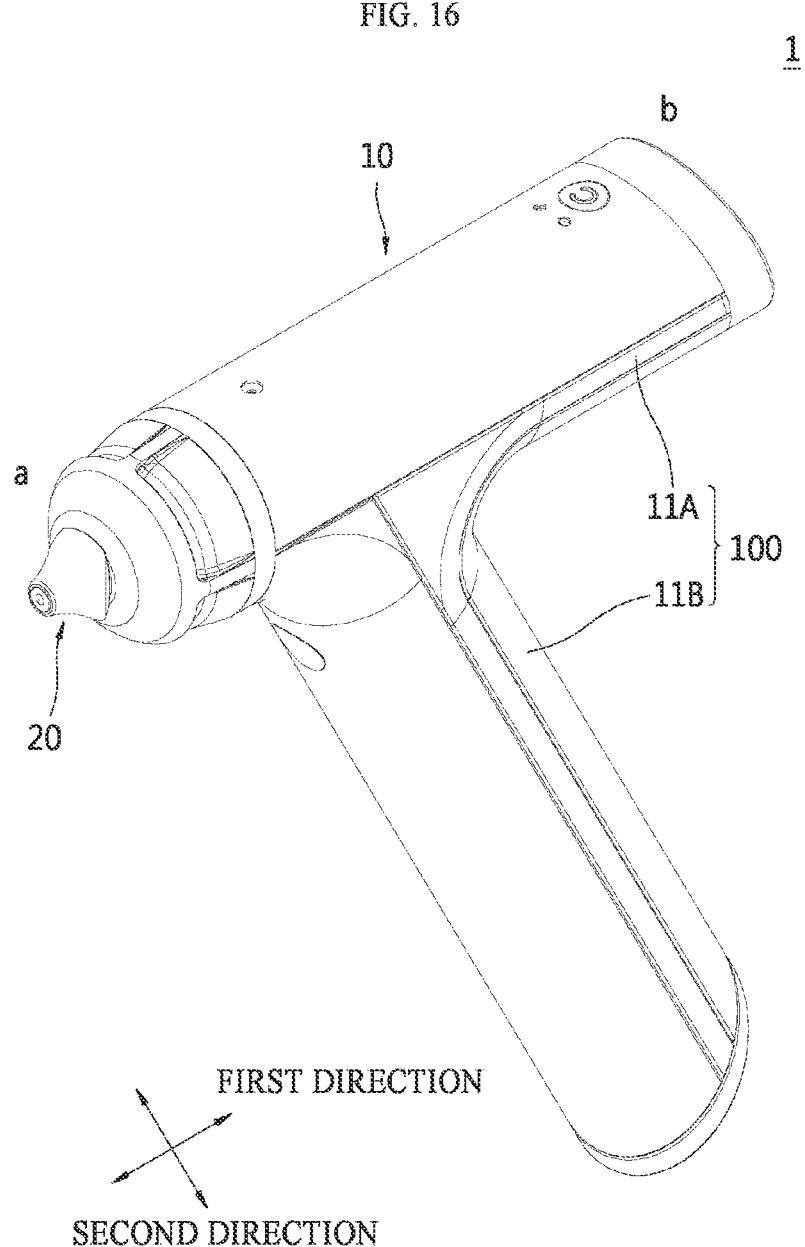
FIGS. 16 to 18 are views for describing an embodiment of a medical cooling system having a cooling function.
Figure 17:
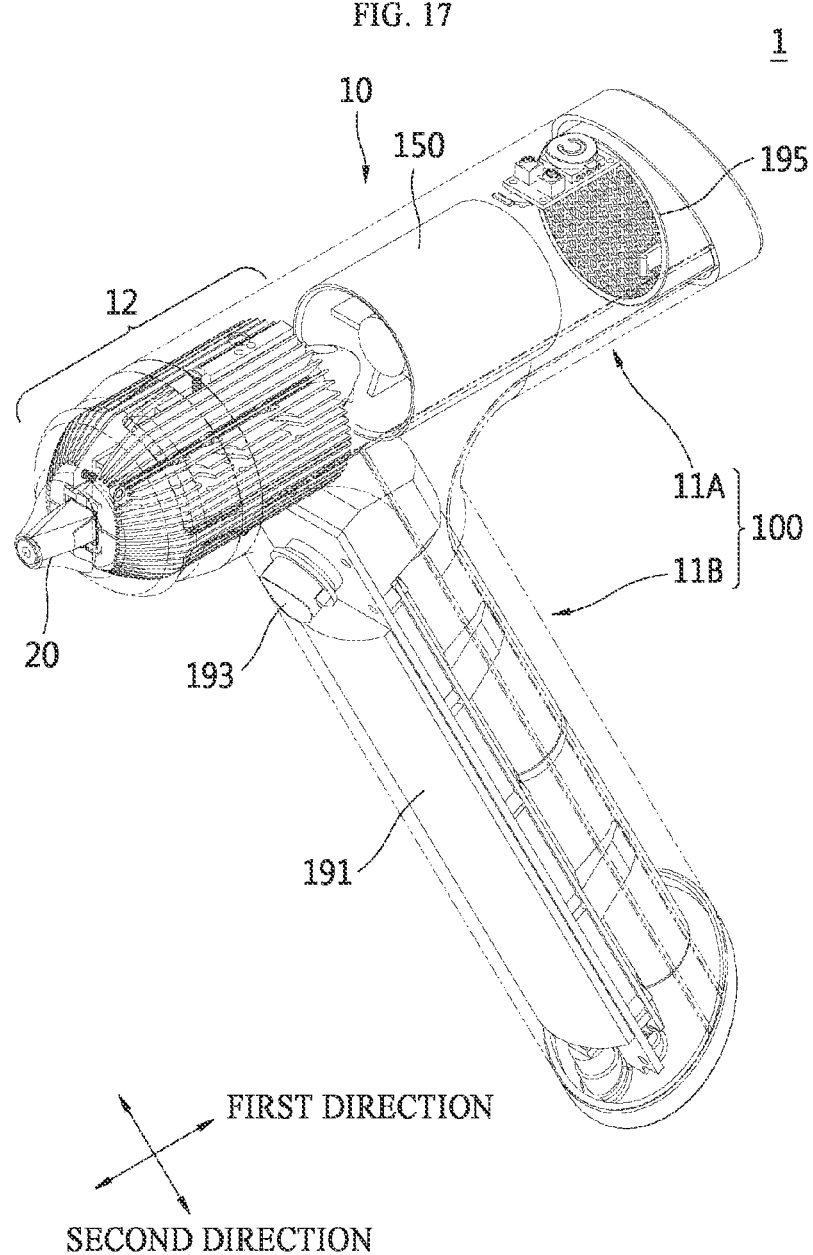
Figure 18:
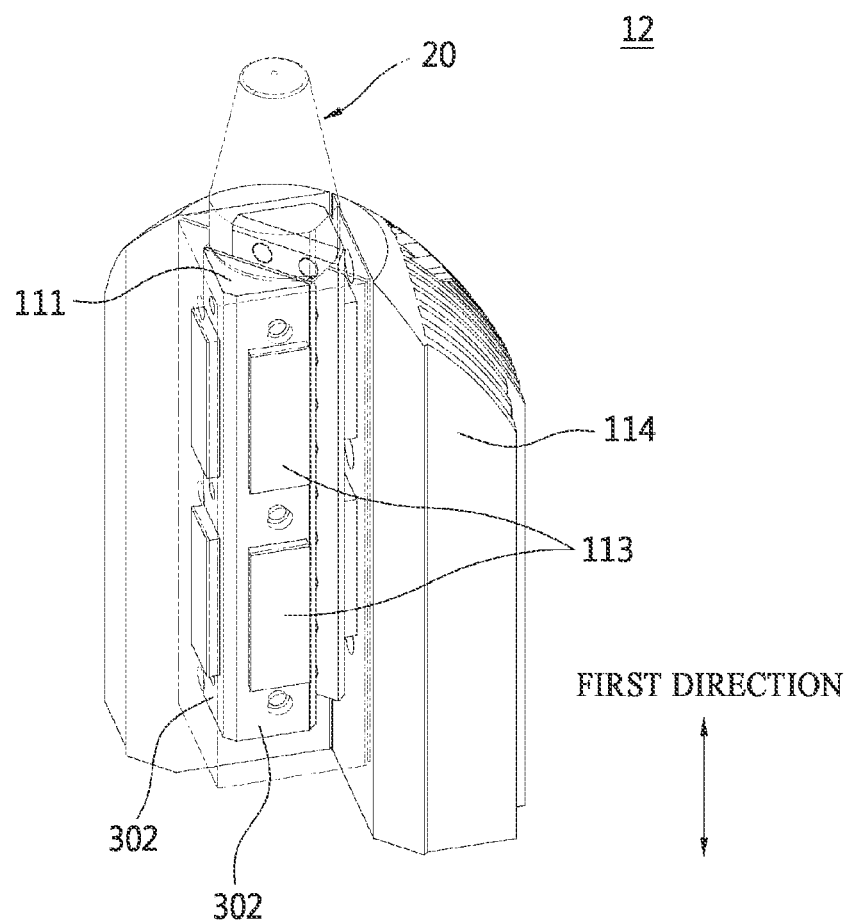

FIG. 16 is a perspective view illustrating a medical cooling system 1 according to an embodiment of the present invention, and FIG. 17 is a perspective view for showing an internal configuration of the medical cooling system 1 illustrated in FIG. 16. FIG. 18 is a view for describing a cooling assembly 12 illustrated in FIG. 17.

Referring to FIG. 17, a medical cooling device 10 according to another embodiment of the present invention may include a main body portion 100, the cooling assembly 12, an air blower 150, and a control unit 170. Also, as necessary, the medical cooling device 10 may further include an input unit 193, a power supply unit 191, and a mesh unit 195.

The main body portion 100 may include a body portion A (11A) and a body portion B (11B). The main body portion 100 may form an exterior of the medical cooling device 10 and accommodate other elements therein. In one embodiment, the main body portion 100 may be formed as a triangular structure as illustrated. Here, the body portion A (11A) may be configured to perform the cooling function, the body portion B (11B) may be configured to perform a power supply function, and to improve user convenience, a separate gripping portion may be configured or may not be formed.

The main body portion 100 may include the input unit 193 configured to generate an input signal according to an external input and the power supply unit 191 including a battery that may be charged by wire or wirelessly or replaced. Also, the mesh unit 195 may be formed at the other end b of the main body portion 100 and perform a function of discharging an air flow formed by the air blower 150 to the outside.

Meanwhile, the cooling assembly 12 according to an embodiment may include a cooling medium accommodating unit 111, a cooling generator 113, and a heat dissipation unit 114 and may further include a temperature sensor unit 145.

Meanwhile, the air blower 150 may be disposed inside the main body portion 100 and form a one-way air flow. For example, the air blower 150 may generate an air flow in a first direction parallel to a longitudinal direction of the main body portion 100 to perform heat dissipation or may generate an air flow in a second direction that is not parallel to the longitudinal direction of the body portion to perform heat dissipation. In a case in which air is blown in the second direction, the air blower may be configured to include a plurality of fans so that heat dissipation is performed more efficiently.

Using a characteristic in that one surface of a thermo-electric element may serve as a cooling surface or a heat-generating surface according to a direction of current, the cooling assembly 12 may heat the cooling medium accommodating unit 111 after use to remove moisture, impurities, or the like from a contact surface as necessary.

Due to such a configuration of the present invention, the medical cooling system 1 may obtain an effect of rapidly and safely cooling a treatment site of a subject that is in contact with a cooling medium 20. Also, due to the configuration, the medical cooling system 1 may obtain an effect of improving the service life and various characteristics of the device. Also, since the medical cooling system 1 controls heat using an electronic element, an effect of enabling precise temperature control may be obtained. Also, the medical cooling system 1 may obtain effects of enabling rapid cooling after power supply and enabling local cooling. Also, the medical cooling system 1 may obtain an effect of being operable in any position or direction regardless of the direction of gravity. Also, the medical cooling system 1 may obtain effects of enabling reduction of size and weight of a cooling unit and implementing low-noise and low-vibration cooling.

Figure 19:
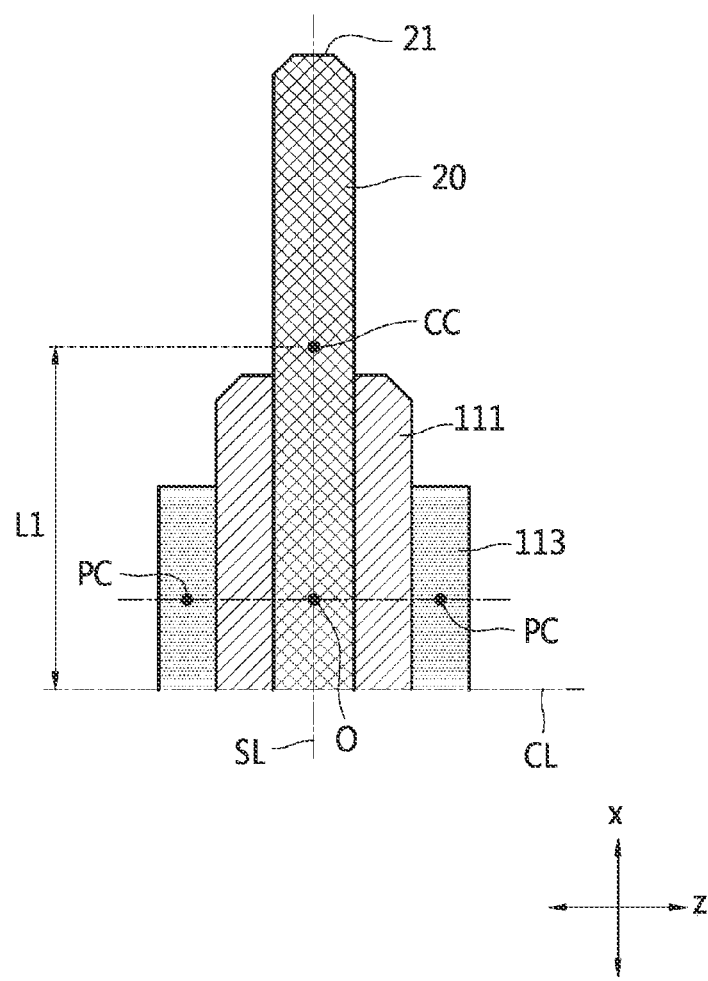
FIGS. 19 and 20 are views for describing a center of cooling power of the medical cooling device.
Figure 20:
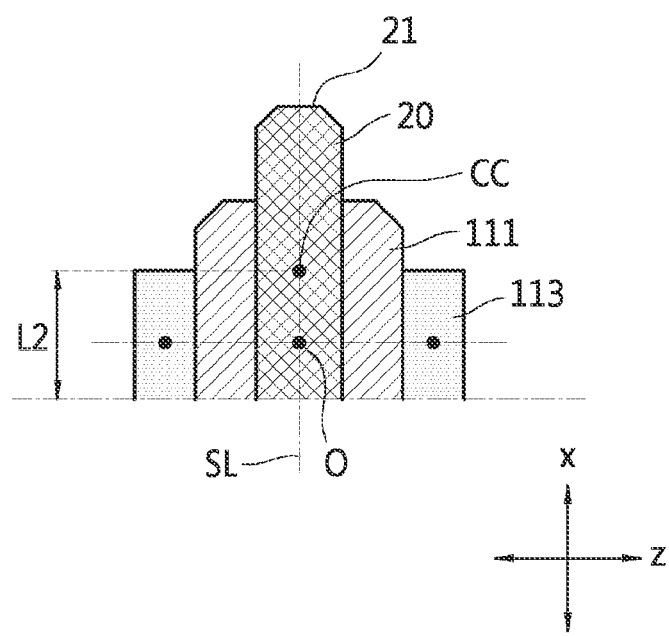

FIGS. 19 and 20 are views for describing a structure according to a center of cooling power of the medical cooling device 10 according to an embodiment of the present invention.

In the present specification, a center-of-cooling-power (CC) region refers to a region corresponding to the center of cooling energy and may define a CC of the entire cooling assembly (thermal assembly) or may define a CC of only the cooling medium 20. Here, as described above, the cooling assembly 12 may be the overall configuration including the cooling medium accommodating unit 111, the cooling generator 113, and the heat dissipation unit 114, but may also be a configuration that takes into consideration only the cooling medium 20 and the cooling medium accommodating unit 111, excluding the cooling generator 113 and the heat dissipation unit 114.

Here, the CC region may be a center region to which cooling energy is transferred in physical coupling between the cooling generator 113 and the cooling medium 20. In other words, the cooling medium 20 or the cooling assembly 12 receives cooling energy generated from the cooling generator 113, and due to physical characteristics of the cooling medium 20 or the cooling assembly 12, the cooling energy is concentrated to regions close to the cooling generator 113, and a cooling energy transfer rate inevitably decreases as the distance from the cooling generator 113 increases. Due to a difference in the cooling energy transfer rate, a cooling temperature may be somewhat different according to sites in the cooling medium 20 or the cooling assembly 12.

The CC region is a concept reflecting the distribution of cooling energy and may be determined according to CC parameters, which will be described below, in a longitudinal direction of the entire cooling medium 20 or cooling assembly 12 from a physical center of a region where the cooling generator 113 and the cooling medium 20 overlap or the cooling generator 113 and the cooling assembly 12 overlap.

Here, in a case in which only the cooling medium 20 is taken into consideration, the CC parameters may include a volume of the cooling medium 20, a distance between a tip 21 of the cooling medium 20 and a center PC of the cooling generator 113, a thermal conductivity of the cooling medium 20, and a distance between the cooling medium 20 and the cooling generator 113. Alternatively, in a case in which the cooling assembly 12 is also taken into consideration, the CC parameters may further include a thermal conductivity of each element of the cooling assembly 12, a volume of each element of the cooling assembly 12, the distance between the tip 21 of the cooling medium 20 and the center PC of the cooling generator 113, and a distance between the cooling medium accommodating unit 111 and the cooling generator 113. Also, in a case in which the cooling generator 113 is provided as a plurality of cooling generators 113, the CC parameters may include the cooling power, cooing amount, and the like of each cooling generator 113.

More specifically, referring to FIG. 19, in the case in which the cooling generator 113 is provided as the plurality of cooling generators 113, the center PC of each cooling generator 113 and a physical center O of the cooling medium 20 may be derived. In a case in which lengths at which the cooling generators 113 overlap the cooling medium 20 or cooling assembly 12 are the same, the physical center O may be the same as the CC. However, since the cooling medium 20 actually extends in the longitudinal direction thereof (x-direction), the CC region may be disposed on an extension line SL that passes through the physical center O and extends in the longitudinal direction of the cooling medium 20 (x-direction).

The term "CC" may refer to a center with respect to thermal conductivity in the CC region. Here, a position of the CC, which is equal to $(\bar{x}_{center}, \bar{y}_{center}, \bar{z}_{center})$, may be defined as follows, and a region in which the CC is formed on the extension line in the longitudinal direction (x-direction) may be defined as the CC region, which is equal to ($\bar{y}_{center}, \bar{z}_{center}$).

$$K = \iiint_{body} \kappa dV$$

$$\bar{x}_{center} = \frac{1}{K} \iiint_{body} x\kappa dV$$

$$\bar{y}_{center} = \frac{1}{K} \iiint_{body} y\kappa dV$$

$$\bar{z}_{center} = \frac{1}{K} \iiint_{body} z\kappa dV$$

In the above equations, the term "body" refers to the entire space including the cooling medium and the cooling medium accommodating unit and may be expressed as dV=dxdydz. Therefore, the positions of the CC region and the CC may be derived by integrating the entire region of the corresponding space.

In one embodiment, referring to FIG. 20, the CC region may be disposed to include a region where the cooling medium and the cooling generator 113 overlap. In other words, by forming the cooling medium 20 to have a short length, efficiency of transferring cooling energy from the cooling generator 113 to the tip 21 of the cooling medium 20 may be improved. However, the technical idea of the present invention is not limited thereto. In another embodiment, the CC region may be disposed to have a length less than or equal to a length L1 or L2 that is preset on the basis of a line CL connecting one ends of the cooling generators 113.

In one embodiment, a length of the cooling medium 20 may be less than or equal to ten times a distance from a lower end of the cooling medium 20 to the CC. There is an effect of shortening the time taken for cooling the cooling medium 20 to cool the target region as the length of the cooling medium 20 is shorter. Therefore, when the length of the cooling medium 20 is adjusted to be less than or equal to ten times the distance from the lower end of the cooling medium 20 to the CC, precise cooling temperature control is possible, and there is an effect of improving a cooling speed.

In another embodiment, a distance from the CC to a front end of the cooling medium 20, that is, the front end thereof cooling the target site, may be less than or equal to 30 mm. In a specific embodiment, the distance from the CC to the front end of the cooling medium 20 may be less than or equal to 25 mm. In a more specific embodiment, the distance from the CC to the front end of the cooling medium 20 may be less than or equal to 20 mm. There is the effect of shortening the time taken for cooling the cooling medium 20 to cool the target region as the length of the cooling medium 20 becomes shorter. Therefore, when the distance from the CC to the front end of the cooling medium 20 is adjusted to be less than or equal to 30 mm, precise cooling temperature control is possible, and there is an effect of improving a cooling speed.

In one embodiment, the CC may be disposed to be collinear with a cooling-concentrated portion CO1 in the longitudinal direction of the cooling medium 20.

As described above, since the medical cooling device 10 according to an embodiment of the present invention includes the cooling medium 20 or cooling assembly 12 so that the CC region is disposed at a preset position, cooling energy generated from the cooling generator 113 may be efficiently transferred to the target region.

6. Cooling Assembly

FIGS. 21 to 25 are views for describing a cooling assembly of the medical cooling device according to another embodiment.

Figure 21:
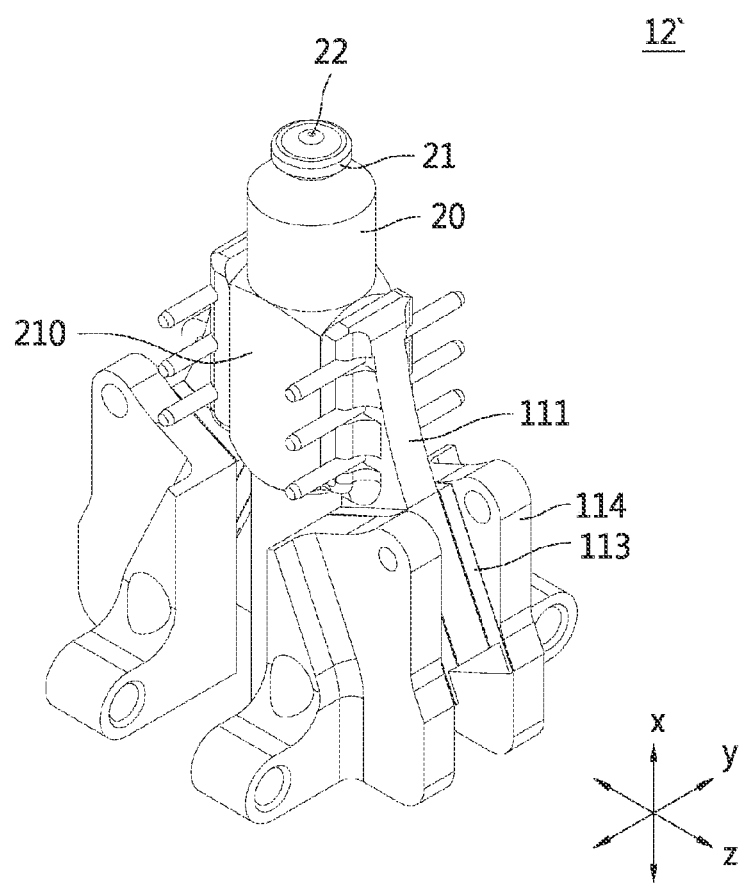
FIGS. 21 to 25 are views for describing a cooling assembly of the medical cooling device according to another embodiment.
Figure 22:
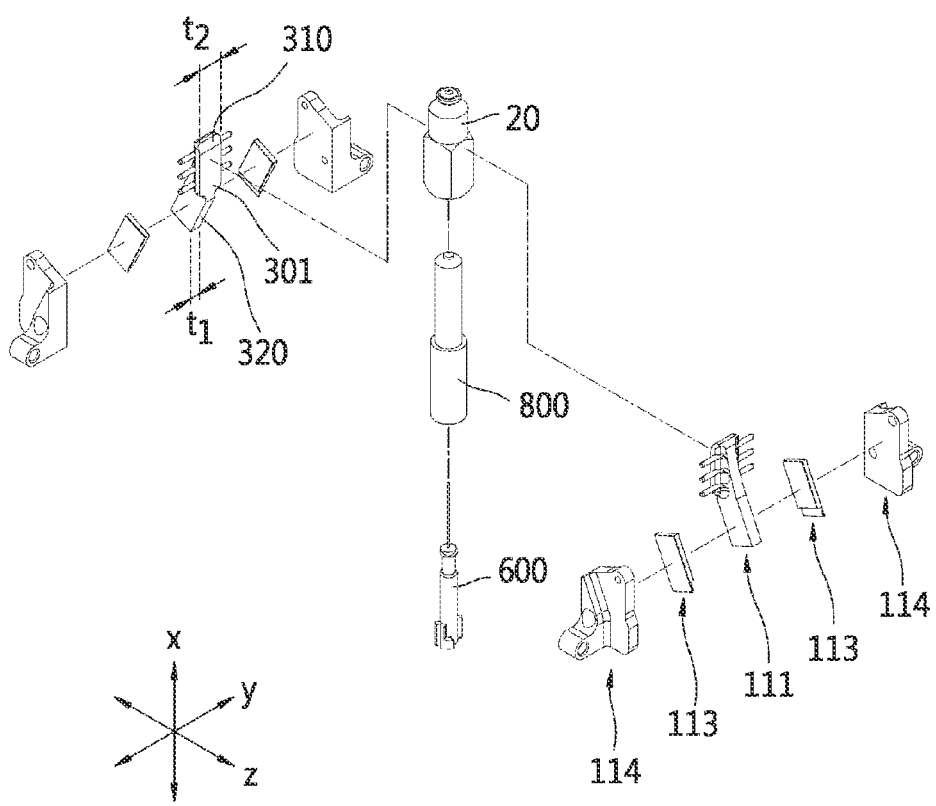
Figure 23:
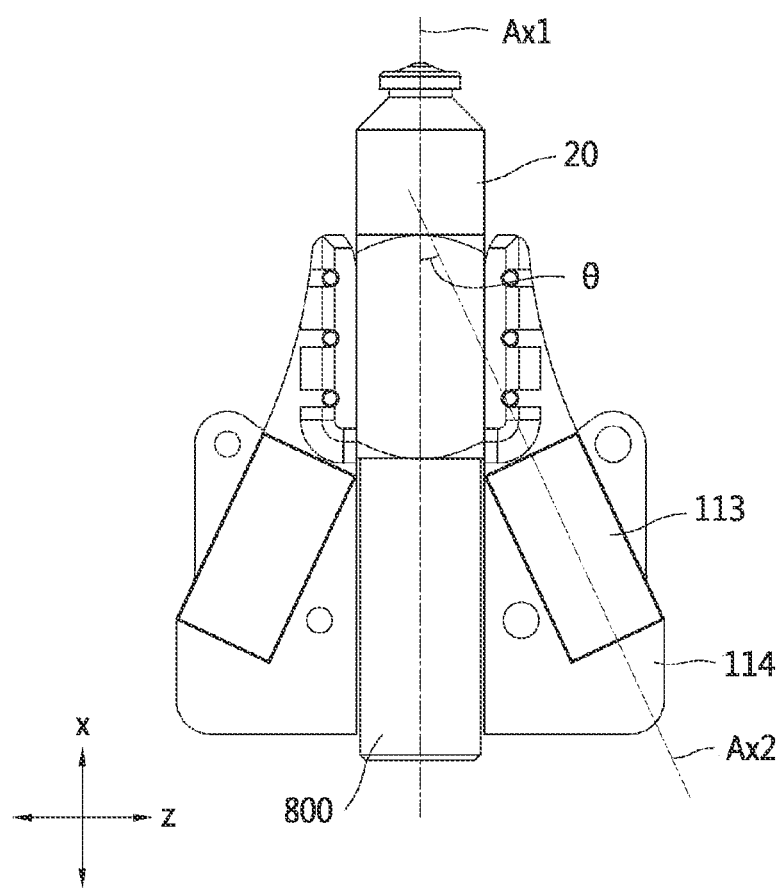
Figure 24:
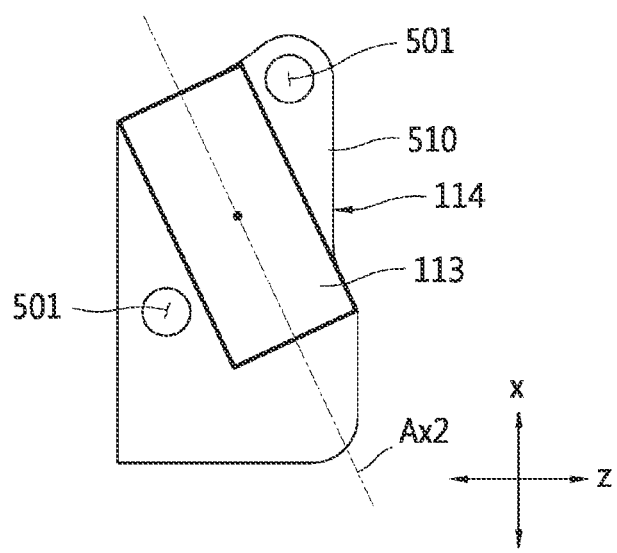
Figure 25:
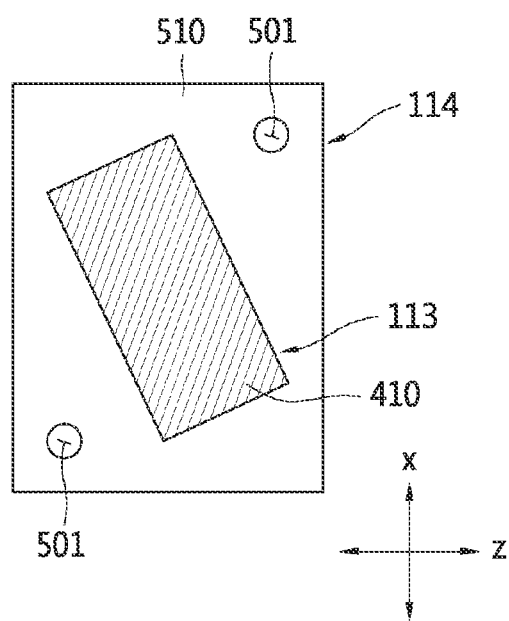

FIG. 21 is a perspective view for describing a cooling assembly 12' according to another embodiment, and FIG. 22 is an exploded perspective view of the cooling assembly 12' of FIG. 21. FIG. 23 is a view excluding some elements to describe an arrangement structure of a cooling generator 113, and FIGS. 24 and 25 are views for describing an arrangement relationship between the cooling generator 113 and a heat dissipation unit 114.

Referring to FIGS. 21 to 25, the cooling assembly 12' according to another embodiment may include a cooling medium accommodating unit 111 configured to accommodate a cooling medium 20, the cooling generator 113, and the heat dissipation unit 114. The cooling assembly 12' according to another embodiment may further include an insulator 800 and an injector 600 that are coupled to the cooling medium 20, and the injector 600 and the cooling medium 20 may be separated to be spaced apart to prevent freezing of a drug accommodated in the injector 600. This will be described in detail below.

The cooling medium accommodating unit 111 thermally and physically connects the cooling medium 20 to the cooling generator 113 to perform a function of transferring cooling energy generated from the cooling generator 113 to the cooling medium 20. According to a preferred embodiment, unlike in one embodiment in which the cooling medium accommodating unit 111 performs a function of accommodating a cooling medium and the entire cooling medium accommodating unit 111 overlaps with and accommodates the cooling medium 20, the cooling medium accommodating unit 111 according to another embodiment only partially overlaps with the cooling medium 20, and the cooling generator 113 is disposed in a portion of the cooling medium accommodating unit 111 that does not overlap with the cooling medium 20 so that the cooling energy is efficiently transferred to the cooling medium 20.

Specifically, the cooling medium accommodating unit 111 may include a contact portion 310 including a contact surface 301 that is thermally coupled to the cooling medium 20 and extending portions 320 extending from the contact portion 310 and at which the cooling generator 113 is disposed. Here, the extending portion 320 may extend in a direction that intersects a longitudinal direction of the cooling assembly 12' (x-direction). For example, referring to FIG. 23, an angle θ between a second axis Ax2 in a direction in which the extending portion 320 extends and a first axis Ax1 in the longitudinal direction of the cooling assembly 12' (x-direction) may be an acute angle.

The cooling medium accommodating unit 111 may include a plurality of split units and accommodate the cooling medium 20 in an accommodation space formed of the split units. In one embodiment, the cooling medium accommodating unit 111 may include two split units, and the two split units may form the accommodation space accommodating the cooling medium 20 in a state in which the two split units are disposed opposite each other. Here, the contact portion 310 of the split unit may overlap with the cooling medium 20, and the extending portions 320 may extend in opposite directions and not overlap with the cooling medium 20.

The cooling generator 113 may be provided as one or more cooling generators 113 disposed on the other surfaces of the extending portions 320 that do not overlap. As illustrated, in a case in which the cooling generator 113 is provided as two cooling generators 113, the cooling generators 113 may be disposed on the other surfaces of the extending portions 320 facing each other. In the cooling medium accommodating unit 111, a width t2 of the contact surface 301 of the cooling generator 113 may be larger than or equal to a width of the cooling medium 20. Here, a thickness t1 of the extending portion 320 of the cooling medium accommodating unit 111 may be formed to be smaller than the width t2 of the contact surface 301 to minimize heat capacity of the cooling medium accommodating unit 111 and maximize a speed at which cooling energy generated from the cooling generator 113 is transferred. According to an embodiment of the present invention, the cooling generator 113 may be coupled to both surfaces of a single cooling medium accommodating unit 111 to improve cooling efficiency.

Meanwhile, the heat dissipation unit 114 may come in contact with a heat-generating surface of the cooling generator 113 and perform a function of dissipating heat generated from the cooling generator 113 to the outside. The heat dissipation unit 114 of the cooling assembly 12' according to another embodiment may not only perform the above-described heat dissipating function but also perform a function of coupling the cooling generator 113 to the cooling medium accommodating unit 111.

Specifically, the heat dissipation unit 114 may be disposed to correspond to the cooling generator 113, and the number of heat dissipation units 114 may correspond to the number of cooling generators 113. Since the cooling generators 113 of the cooling assembly 12' have the extending portions 320 interposed therebetween and are disposed opposite to each other, the heat dissipation units 114 may also be coupled to each other in a state in which the heat dissipation units 114 are disposed to face each other. In other words, since the heat dissipation units 114 are coupled to each other in a state in which the cooling generators 113 are disposed between the heat dissipation units 114, the heat dissipation units 114 and the cooling generators 113 may be coupled without direct mechanical coupling. In this way, since the heat dissipation units 114 and the cooling generators 113 may be thermally separated, cooling loss due to a coupling member such as threads may be minimized.

According to an embodiment of the present invention, the cooling generator 113 may be disposed on the other surface of the extending portion 320, and the direction in which the extending portion 320 extends may coincide with the longitudinal direction of the cooling generator 113. In other words, the cooling generator 113 may be disposed to be inclined with respect to the longitudinal direction of the cooling assembly 12' (x-direction) as illustrated in FIG. 24, instead of being disposed to be vertical or horizontal to the longitudinal direction of the cooling assembly 12' (x-direction). Through such a configuration, the heat dissipation unit 114 may come in contact with the entire heat-generating surface of the cooling generator 113 and secure a space 501, in which a coupling member (not illustrated) is disposed, in a region that does not overlap with the cooling generator 113.

Since the cooling assembly (thermal assembly) according to the present invention reduces a length from the cooling generator 113 to a surface at which the cooling medium comes in contact with a treatment site, the cooling efficiency and cooling speed may be improved. That is, a length of the cooling medium may be formed to be less than a predetermined length to minimize the time taken for cooling the cooling medium 20, and by reducing the length, the overall volume of the cooling assembly may be reduced and thus cooling energy of a thermoelectric element may be transferred rapidly and efficiently to the target region. For example, the length of the tip of the cooling medium may be configured to be 30 mm or less, and the overall length of the cooling medium may be configured to be 50 mm or less.

FIG. 25 is a schematic diagram for describing an area relationship between the heat dissipation unit 114 and the cooling generator 113. In order to mechanically couple the heat dissipation unit 114 to the cooling generator 113 without the heat dissipation unit 114 passing through the cooling generator 113, the heat dissipation unit 114 should come in contact with the entire cooling generator 113 and secure a space in which a coupling member (not illustrated) is disposed. Therefore, one surface 510 of the heat dissipation unit 114 that comes in contact with the cooling generator 113 may have an area that is larger than an area of one surface 410 of the cooling generator 113.

According to an embodiment of the present invention, in order to reduce the size while securing a coupling region, coupling may be performed so that a central axis of the heat dissipation unit 114 and a central axis of the thermoelectric element are not parallel, or the central axis of the heat dissipation unit 114 is inclined with respect to the central axis of the thermoelectric element. In this way, the coupling region may be secured in the heat dissipation unit 114.

According to another embodiment of the present invention, the heat dissipation unit 114 may secure a coupling region using the entire area of the one surface 510 that comes in contact with the cooling generator 113, a contact area that comes in contact with the cooling generator 113, and a non-contact area that does not come in contact with the cooling generator 113. For example, by configuring the non-contact area to be an area less than or equal to a predetermined area, the heat dissipation unit 114 may come in contact with the entire cooling generator 113 and secure the coupling space 501.

7. Drug Injection Structure

FIGS. 26 to 29 are views for describing a medical cooling system having a drug injection function.

A medical cooling system 1 according to another embodiment firstly performs a cooling function in a target region and secondly performs a function of injecting a drug to be injected. Hereinafter, for convenience of description, the same elements will be denoted by the same reference numerals, and repeated description will be omitted.

Figure 26:
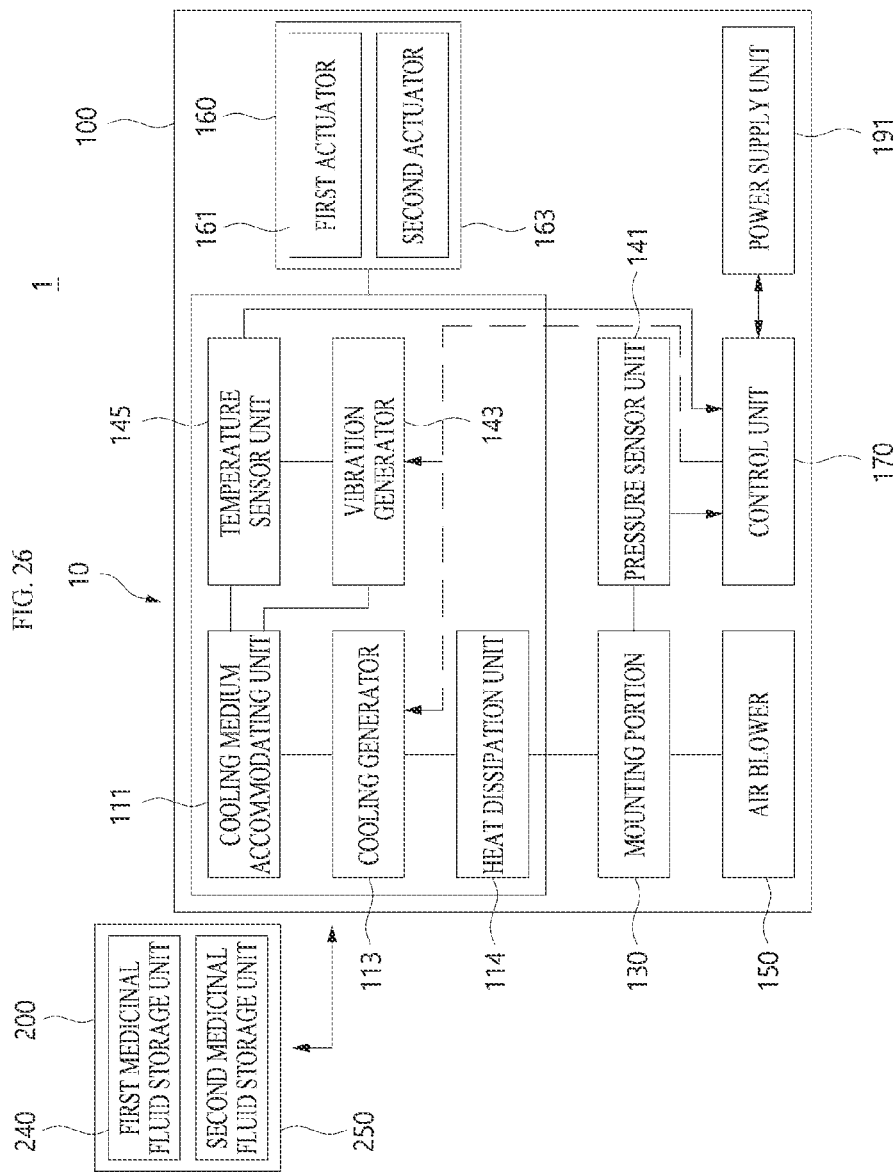
FIGS. 26 to 29 are views for describing a medical cooling system having a drug injection function.
Figure 27:
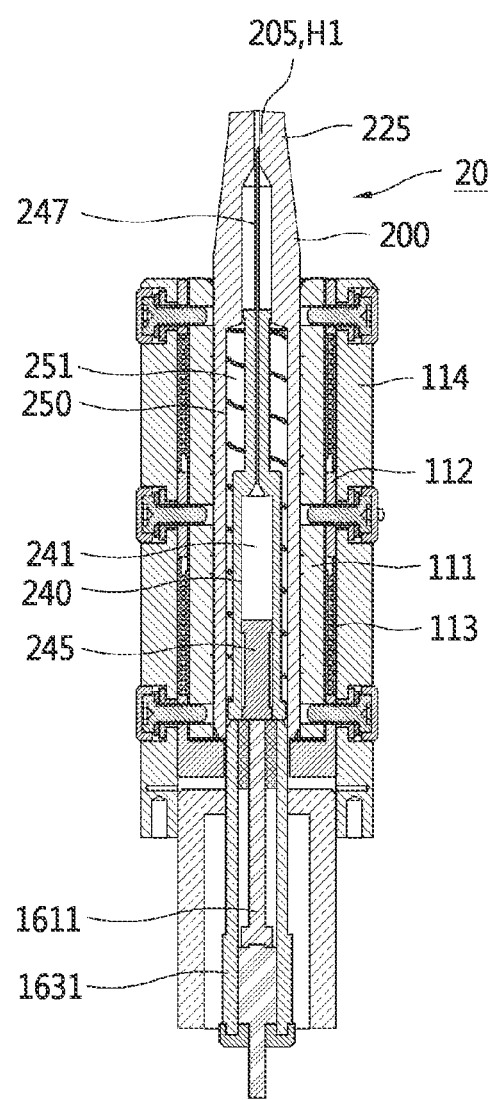
Figure 28:
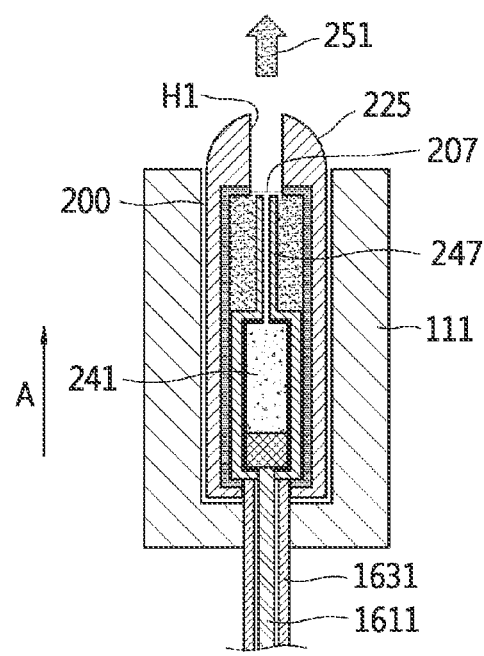
Figure 29:
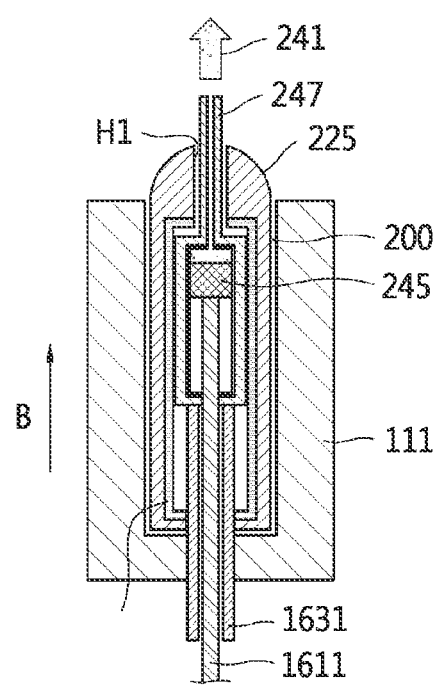

FIG. 26 is a block diagram of the medical cooling system 1 according to another embodiment of the present invention, FIG. 27 is a cross-sectional view illustrating one embodiment of a detachable cooling medium 20 of the medical cooling system 1 according to another embodiment, and FIGS. 28 and 29 are views for describing technology related to an actuator of a medical cooling device.

Referring to FIGS. 26 and 27, the medical cooling system 1 according to another embodiment of the present invention includes a medical cooling device 10 and the detachable cooling medium 20 accommodated in the medical cooling device 10.

The medical cooling device 10 may further include an injection unit 160.

The injection unit 160 performs a function of applying pressure to the detachable cooling medium 20 to discharge a medicinal fluid of a medicinal fluid storage unit disposed in the detachable cooling medium 20 to the outside. The injection unit 160 may include an actuator. In one embodiment, the injection unit 160 may include a first actuator 161 and a second actuator 163. Also, the injection unit 160 may include a first injecting part 1611 configured to move linearly in a direction of a driving shaft according to driving of the first actuator 161 and a second injecting part 1631 configured to move linearly in a direction of a driving shaft according to driving of the second actuator 163. Alternatively, at least any one of the driving shaft of the first actuator 161 and the driving shaft of the second actuator 163 may be coupled to a movement shaft, along which the first injecting part 1611 or the second injecting part 1631 moves, through a link. The link performs a function of converting rotary motion of the first actuator 161 or the second actuator 163 to linear motion and may be provided as one or more links. Due to the link, the driving shaft of the first actuator 161 or the driving shaft of the second actuator 163 may not be parallel to the movement shaft along which the first injecting part 1611 or the second injecting part 1631 moves. Alternatively, the driving shaft of the first actuator 161 or the driving shaft of the second actuator 163 may also be configured as the above-described link.

Meanwhile, the detachable cooling medium 20 may include a main body portion 200 and a first medicinal fluid storage unit 240.

The main body portion 200 may be detachably mounted to the medical cooling device 10. The main body portion 200 may refer to a body of the detachable cooling medium 20 that includes the insertion region 210 and the non-insertion region 220 of the detachable cooling medium 20. The main body portion 200 may come in contact with a target region and perform the cooling function of the detachable cooling medium 20 and, simultaneously, perform a function of discharging or injecting the medicinal fluid stored therein to the target region. Therefore, in the present embodiment, since the detachable cooling medium 20 includes all of the above-described elements provided for the cooling function of the detachable cooling medium 20 according to the previous embodiment, repeated description will be omitted.

The main body portion 200 may include a front end portion 225 of FIG. 27 disposed at a distal end. Here, a discharge part 205 may be disposed at the front end portion 225. A needle hole (not illustrated) passing through the main body portion 200 may be formed in the front end portion 225 to allow an injection needle 247 to pass therethrough, and the discharge part 205 formed in the shape of a tube having a predetermined diameter may be disposed at a position that corresponds to the needle hole (not illustrated). The discharge part 205 serves as a fixed injection needle.

The first medicinal fluid storage unit 240 may store a first medicinal fluid 241 to be injected to a target region and may be movably disposed inside the main body portion 200. Although not illustrated, a hollow part (not illustrated) may be formed inside the main body portion 200 to allow the first medicinal fluid storage unit 240 to be movable, and the first medicinal fluid storage unit 240 may move along the hollow part (not illustrated).

Specifically, the first medicinal fluid storage unit 240 may include the injection needle 247 disposed at one end to inject the first medicinal fluid 241. The injection needle 247 may be disposed to have an axis parallel to the discharge part 205 and may move together with the first medicinal fluid storage unit 240 when the first medicinal fluid storage unit 240 moves in an axial direction of the main body portion 200. The injection needle 247 serves as a movable injection needle.

Meanwhile, the first medicinal fluid storage unit 240 may include an injector 245 disposed on an extension line of the central axis. The injector 245 may move due to an actuator that interlocks with the injector 245 when the detachable cooling medium 20 is mounted to the medical cooling device 10. Due to the injector 245, which is disposed inside the first medicinal fluid storage unit 240, moving due to the actuator of the medical cooling device 10, the first medicinal fluid storage unit 240 may push the first medicinal fluid to the outside.

In another embodiment, the detachable cooling medium 20 may further include a second medicinal fluid storage unit 250 configured to store a second medicinal fluid 251. The second medicinal fluid storage unit 250 may be arranged in line with the first medicinal fluid storage unit 240 in the axial direction of the main body portion 200. The second medicinal fluid storage unit 250 may be disposed to be more adjacent to the front end portion 225 than to the first medicinal fluid storage unit 240. Here, the detachable cooling medium 20 performs a function of injecting a plurality of medicinal fluids into a target region. The second medicinal fluid storage unit 250 may push the second medicinal fluid 251 accommodated therein to the outside due to movement of the first medicinal fluid storage unit 240. Here, the first medicinal fluid 241 and the second medicinal fluid 251 may be different drugs. For example, the first medicinal fluid 241 may include a therapeutic agent, and the second medicinal fluid 251 may include a disinfectant.

Hereinafter, a drug injection process of the detachable cooling medium 20 according to operation of an actuator will be described with reference to FIGS. 28 and 29.

First, the detachable cooling medium 20 is inserted into the cooling medium accommodating unit 111 of the medical cooling device 10 and reaches a state illustrated in FIG. 28. In the state illustrated in FIG. 28, when the second injecting part 1631 moves linearly in a direction indicated by an arrow A, the second injecting part 1631 and the first injecting part 1611 move together and push the first medicinal fluid storage unit 240. Here, the injection needle 247 disposed at one end of the first medicinal fluid storage unit 240 also moves together, and during the movement, the injection needle 247 is inserted into a needle hole H1 and pierces a sealing film 207. Therefore, the second medicinal fluid 251 accommodated in the second medicinal fluid storage unit 250 may be injected into the target region through the needle hole H1.

In a state illustrated in FIG. 29, at this time, when the first actuator 161 is driven and the first injecting part 1611 moves linearly in a direction indicated by an arrow B, as illustrated, the first injecting part 1611 presses the injector 245 disposed inside the first medicinal fluid storage unit 240. Therefore, the first medicinal fluid 241 accommodated in the first medicinal fluid storage unit 240 may be injected into the target region through the injection needle 247.

As described above, since the medical cooling system 1 according to embodiments of the present invention supplies intensive cooling energy to a cooling medium that comes in contact with a treatment site and performs cooling, rapid cooling action may be performed. Also, since the medical cooling system 1 according to embodiments of the present invention may perform local anesthesia on a treatment site through cooling and inject a medicinal fluid therein, the pain of a patient may be reduced.

The medical cooling system 1 having the above-described configuration may control a temperature through the control unit 170 to cool a target region according to a purpose.

8. Actuator Structure

FIGS. 30 to 42 are views for describing an actuator structure for drug injection of the medical cooling device.

Figure 30:
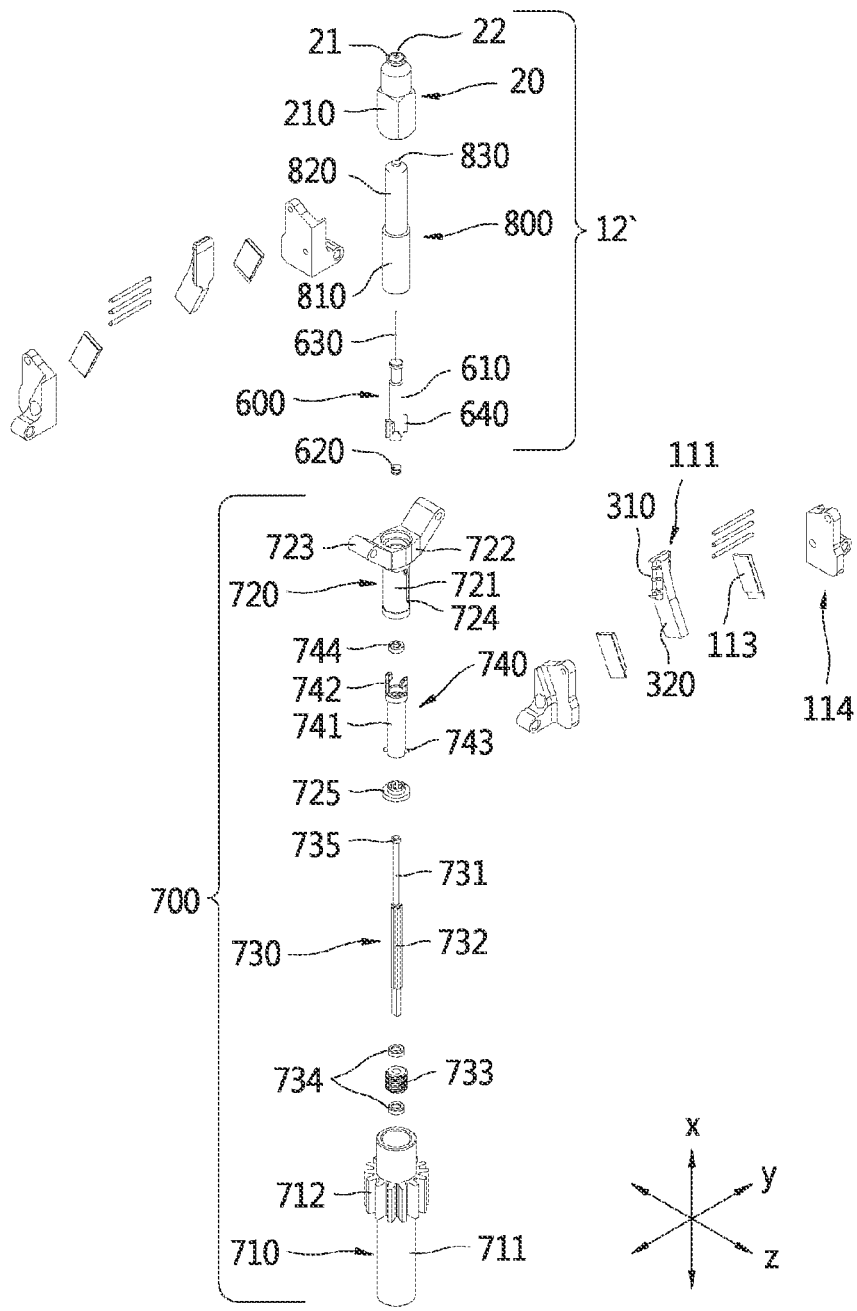
FIGS. 30 to 42 are views for describing an actuator structure for drug injection of the medical cooling device.
Figure 31:
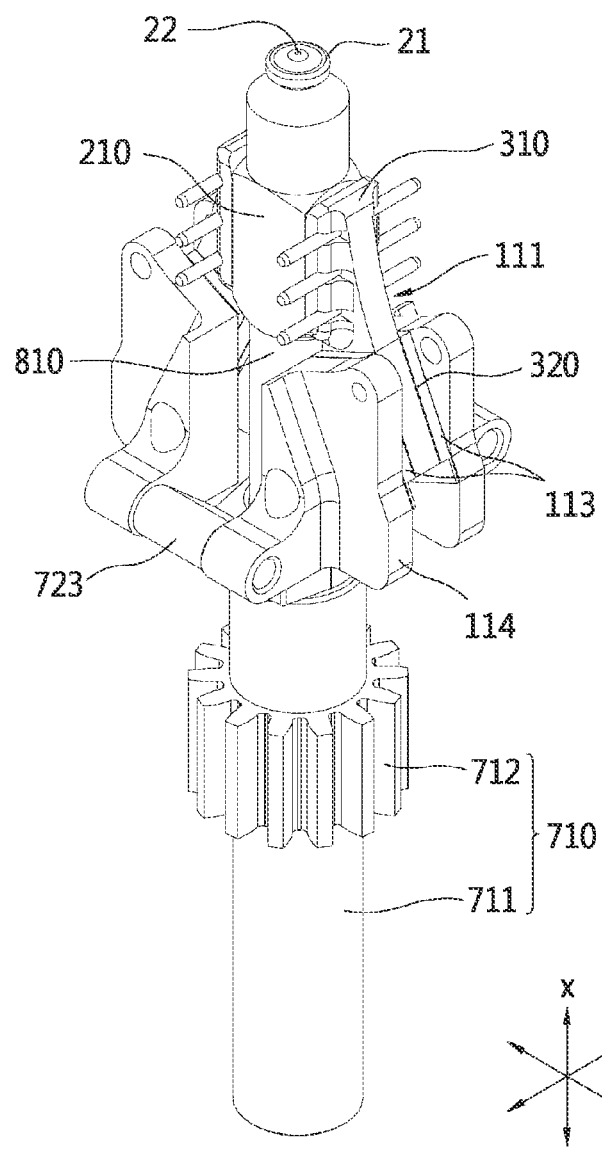
Figure 41:
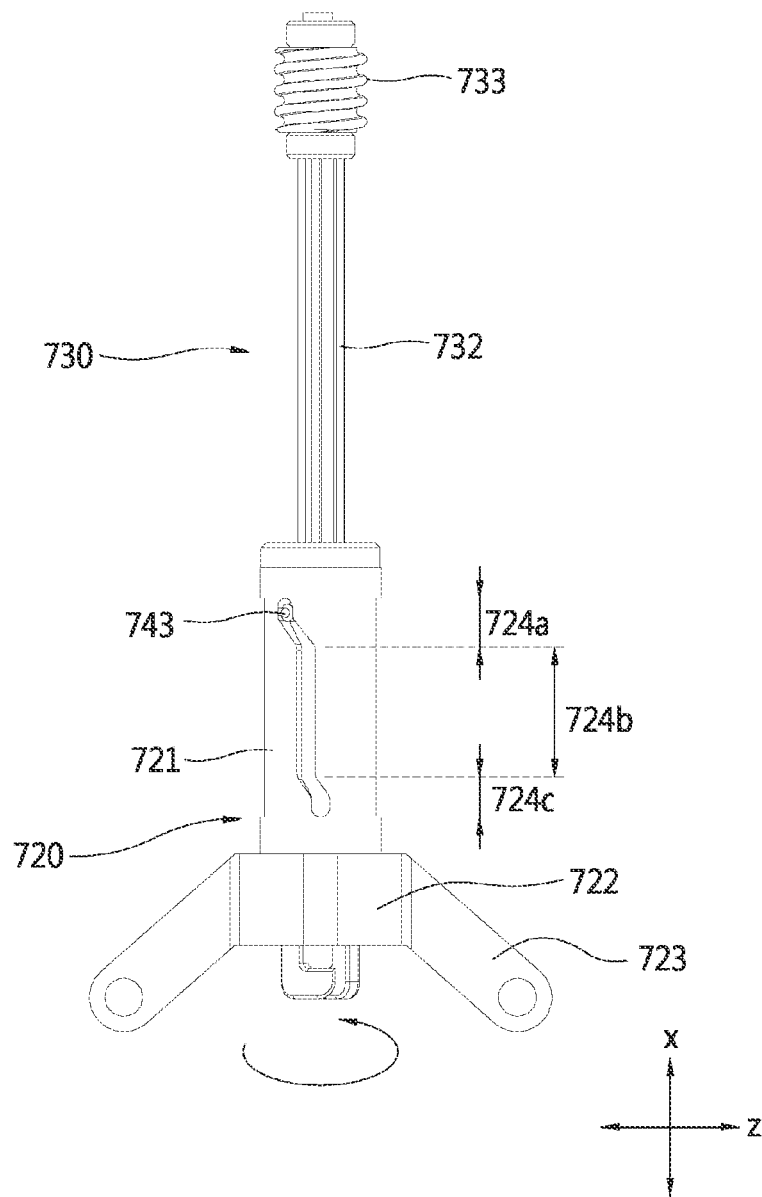
Figure 42:
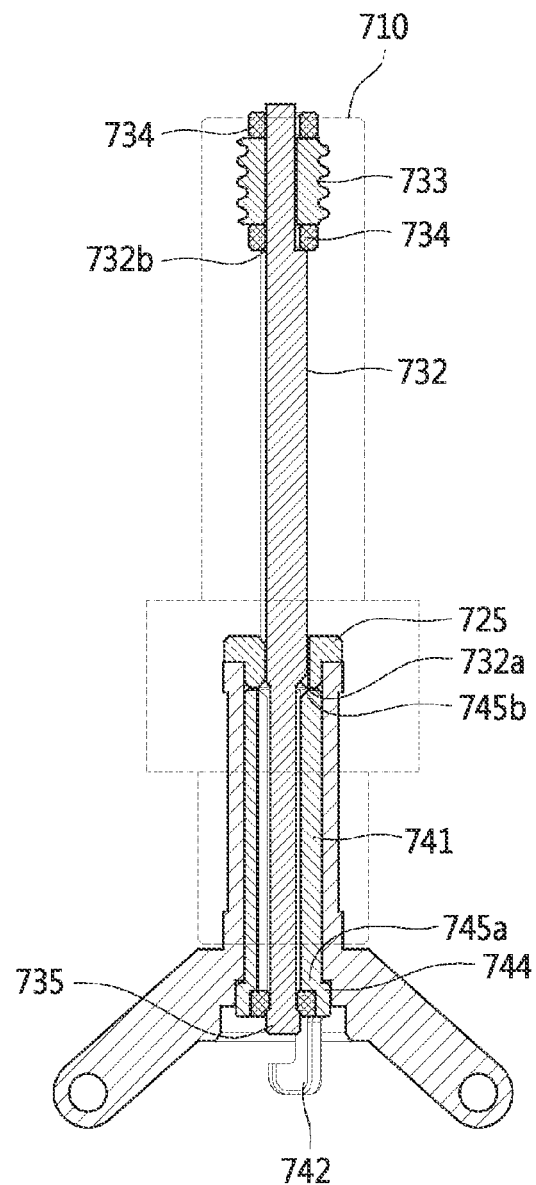

FIG. 30 is an exploded perspective view of a cooling assembly 12' and an actuator 700 according to an embodiment of the present invention, and FIG. 31 is a perspective view of the cooling assembly 12' and the actuator 700 of FIG. 30. FIGS. 32 to 40 are views for describing components of the cooling assembly 12' and the actuator 700, and FIGS. 41 and 42 are views for describing assembly states of major components of the cooling assembly 12' and the actuator 700.

Referring to FIGS. 30 and 31, a medical cooling device 10 may include the cooling assembly 12' configured to accommodate a cooling medium 20 and the actuator 700 for drug injection. Hereinafter, basically, description will be given with reference to FIGS. 30 and 31, and specific components will be described with reference to the corresponding drawings.

The cooling assembly 12' may include a cooling medium accommodating unit 111, an insulator 800, a cooling generator 113, a heat dissipation unit 114, and an injector 600. The cooling medium 20 may be detachably disposed in the medical cooling device 10 and is not a configuration included in the cooling assembly 12', but for convenience of description, description of the cooling medium 20 will also be given here. Also, since the cooling medium accommodating unit 111, the cooling generator 113, and the heat dissipation unit 114 have been described above, repeated description will be omitted.

Figure 32:
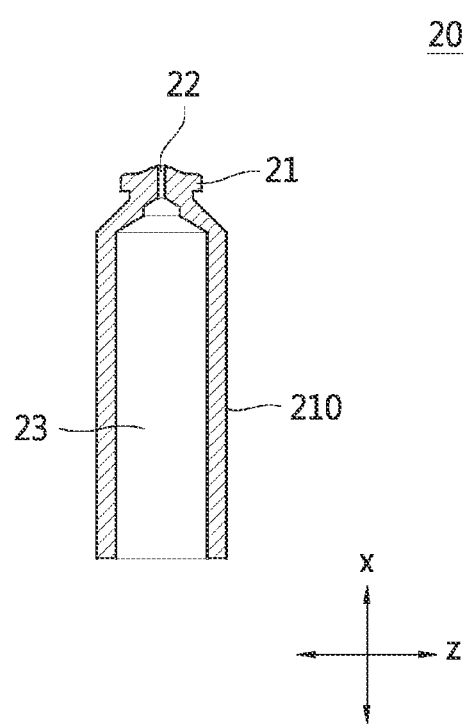

Referring to FIG. 32, the cooling medium 20 comes in contact with a patient's body tissue such as an eyeball, that is, a target region, and performs a function of cooling the target region to perform local anesthesia thereon. The cooling medium 20 may have a body extending to a predetermined length, and as illustrated, the body may include an accommodation space 23 disposed therein to accommodate the insulator 800 which will be described below.

The cooling medium 20 may be formed at a front end portion and may include a tip 21 that comes in contact with a target region to cool the target region. Here, a first path 22 that allows the accommodation space 23 of the cooling medium 20 and the outside of the cooling medium 20 to communicate may be formed in the tip 21. An injecting part 630 of the injector 600 which will be described below may pass through the first path 22 and be exposed to the outside.

The injecting part 630 according to the present invention may serve to inject a liquid into an external target region. To this end, the injecting part 630 may include a discharge part configured to discharge the liquid and may further include an injection part configured to inject the liquid into the target region, a spray part configured to spray the liquid widely to the target region, and the like.

The cooling medium 20 may include an insertion region 210 inserted into the cooling assembly 12', and the insertion region 210 may have an outer side surface that comes in contact with the cooling medium accommodating unit 111. Although the insertion region 210 of the cooling medium 20 is illustrated in the drawing as having a flat outer side surface, the technical idea of the present invention is not limited thereto, and of course, the insertion region 210 may have a curved surface having a curvature. In this case, a contact surface of the cooling medium accommodating unit 111 may also be formed in the shape that corresponds thereto. In order to effectively transfer cooling energy from the medical cooling device 10, the cooling medium 20 may be made of a material having a high thermal conductivity, e.g., gold (Au), silver (Ag), copper (Cu), aluminum (Al), or the like.

Figure 33:
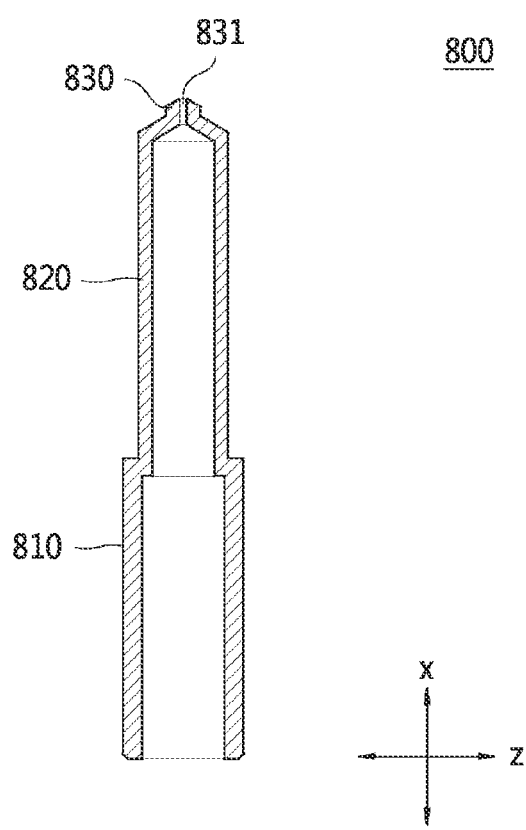

Referring to FIG. 33, the insulator 800 may include a first body 810 having a predetermined size and a second body 820 connected to a front end of the first body 810 and having a diameter or width smaller than that of the first body 810. Also, a tip 830 of the insulator 800 may be disposed at a front end portion of the second body 820. The first body 810 may be disposed outside the cooling medium 20, and the second body 820 and the tip 830 may be disposed in the accommodation space 23 of the cooling medium 20. Specifically, the second body 820 may be disposed in the accommodation space 23 of the cooling medium 20, and the tip 830 may be fitted to the tip 21 of the cooling medium 20.

In order to accommodate the injector 600, which will be described below, therein, the insulator 800 may have an internal space that allows the inside of the first body 810 and the inside of the second body 820 to communicate. A second path 831 that allows the internal space of the insulator 800 to communicate with an external space may be formed in the tip 830 of the insulator 800. Therefore, when the insulator 800 is inserted into the cooling medium 20, the first path 22 of the cooling medium 20 and the second path 831 of the insulator 800 may be connected to each other, and through the first path 22 and the second path 831, the internal space of the insulator 800 disposed in the cooling medium 20 may communicate with the outside. In this way, the injecting part 630 of the injector 600 may protrude to the outside.

Figure 34:
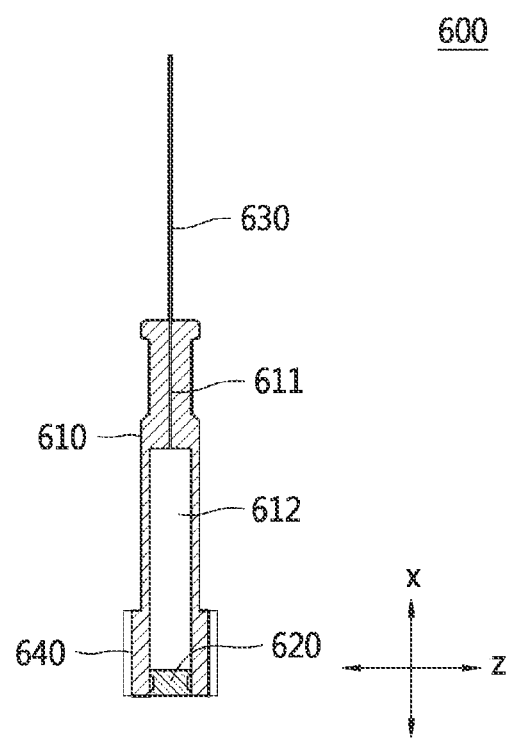

Referring to FIG. 34, the injector 600 may include a body 610 having a predetermined size and a reservoir 612 formed inside the body 610. The reservoir 612 may accommodate a predetermined drug, and generally, the drug may be a liquid. A plug 620 disposed at one side of the reservoir 612 to seal the reservoir 612 may be provided inside the reservoir 612. When the plug 620 moves forward within the reservoir 612 due to an external member, the drug stored in the reservoir 612 may be pressed to be discharged to the outside. Also, a third path 611 that communicates with the reservoir 612 may be formed in the body 610. The injecting part 630 that communicates with the third path 611 may be installed at a front end portion of the body 610. When the injecting part 630 protrudes to the outside through the paths 831 and 22 of the insulator 800 and the cooling medium 20 as described above, the drug in the reservoir 612 may be injected into a target region through the third path 611 and the injecting part 630. Also, the injector 600 may include a latch or flap 640 provided at a rear portion of the body 610 to be selectively coupled to the actuator 700 which will be described below.

The cooling medium 20 may be cooled to a considerably low temperature within a short time to anesthetize a target region. Due to the cooling medium 20, a drug stored in the injector 600 adjacent to the cooling medium 20 may freeze and thus may be difficult to be released from the injector 600. Due to such a reason, the injector 600 may be spaced apart from the cooling medium 20 and be disposed outside or behind the medical cooling device 10. The actuator 700 is connected to the injector 600 and performs a function of loading the injector 600, which is disposed behind, into the second body 820 of the insulator 800 to inject the drug. Through such a configuration, since an influence of the cooling medium 20, which is cooled to a low temperature, on the injector 600 is minimized, it is possible to effectively prevent the drug in the injector 600 from freezing.

Meanwhile, the actuator 700 may simultaneously perform the function of loading the injector 600 and the function of injecting the drug in the injector 600 into the target region. Also, after the drug is injected, the actuator 700 may extract or unload the injector 600 from the cooling medium 20, that is, the second body 820 of the insulator 800.

Figure 35:
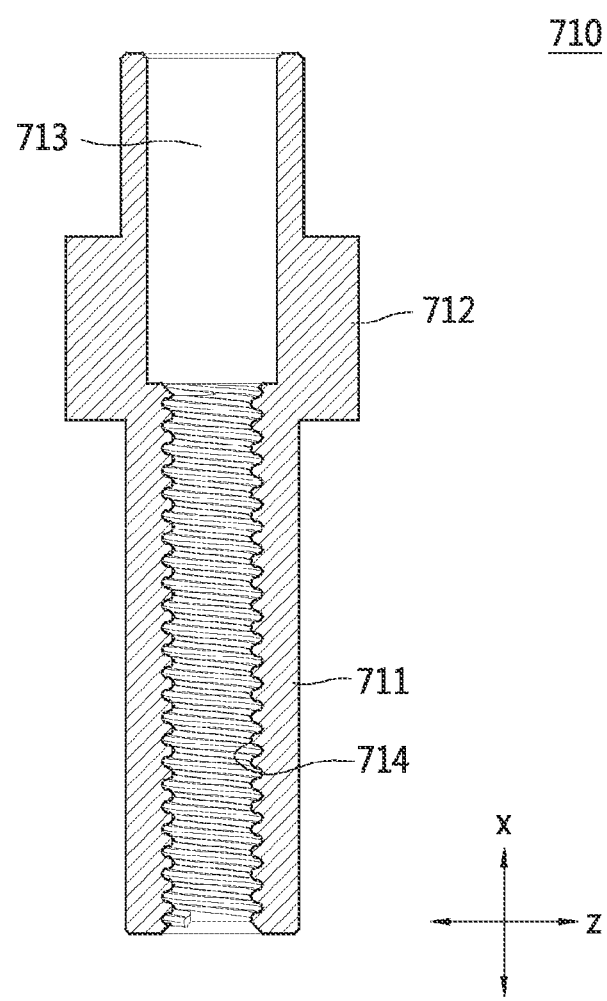

Referring to FIG. 35, the actuator 700 may include a rear housing 710. The rear housing 710 may have a cylindrical body 711. The rear housing 710 may be disposed to rotate in the medical cooling device 10. Various mechanisms may be applied to rotate the rear housing 710. For example, the rear housing 710 may include a gear 712 formed at an outer circumferential surface of a body 711. The gear 712 may be engaged with another gear connected to a driving member and rotate the rear housing 710 by driving of the driving member. As illustrated in FIG. 35, a socket 713 configured to accommodate a front housing 720, which will be described below, may be formed at a front portion of the rear housing 710. The socket 713 may extend to a predetermined length from a front end of the rear housing 710. Also, threads 714 that are formed continuously from a rear end of the socket 713 to a rear end of the rear housing 710 may be disposed at an inner surface of the rear housing 710.

Figure 36:
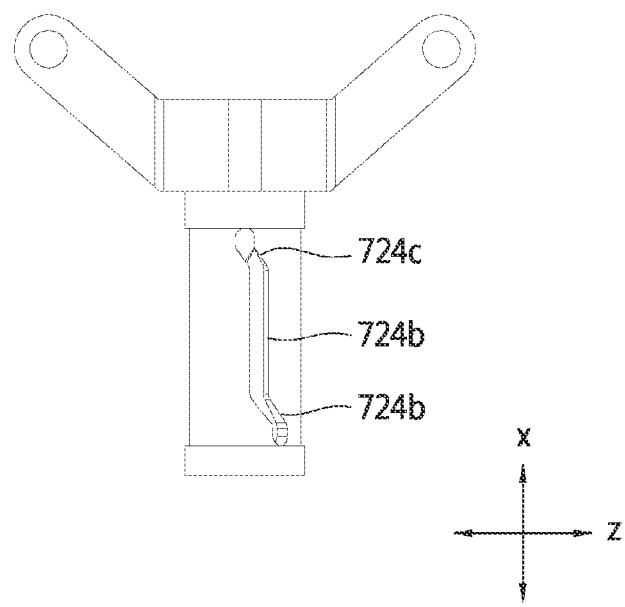

Referring to FIGS. 36, 41, and 42, the front housing 720 may be coupled to the front portion of the rear housing 710 and, specifically, may be rotatably fitted into the socket 713 of the rear housing 710. The front housing 720 may include a cylindrical body 721 and a head 722 provided at a front portion of the body 721. The body 721 of the front housing 720 may be rotatably inserted into the socket 713 of the rear housing 710, and the head 722 may be exposed to the outside of the rear housing 710. The head 722 may have a plurality of arms 723 extending therefrom.

While the rear housing 710 rotates, the front housing 720 may maintain a relatively stationary state in order to guide movement of components accommodated therein. To this end, the front housing 720 may be fixed to other members adjacent thereto through the arms 723. For example, as illustrated in FIG. 31, the arms 723 may be fixed to the heat dissipation unit 114 adjacent thereto, and accordingly, while the rear housing 710 rotates, the front housing 720 may allow relative rotation of the rear housing 710 but maintain a stationary state. Specifically, the front housing 720 may include a track 724 configured to guide movement of a second plunger 740 which will be described below.

The track 724 may be formed of a groove that passes through a wall surface of the body 721. As illustrated in FIGS. 40 to 54, a pin 743 of the second plunger 740 may be inserted into the track 724, and the track 724 may guide the pin 743 and control movement of the entire second plunger 740 connected thereto. Therefore, due to a coupling relationship between the track 724 and the pin 743, the second plunger 740 may perform both translational motion and rotary motion.

Specifically, as illustrated in FIGS. 36 and 41, in terms of function and structure, the track 724 may be divided into first to third sections 724a, 724b, and 724c that are connected to each other. The first section 724a may be formed in a spiral shape and may simultaneously rotate the second plunger 740 by a predetermined angle in any one direction and move the second plunger 740 linearly. The second section 724b may be formed in the shape of a straight line to be parallel to the central axis of the front housing 720 and may allow the second plunger 740 to move linearly in the axial direction. The third section 724c may be formed in a spiral shape like the first section 724a and may simultaneously further rotate the second plunger 740 by a predetermined angle in the same direction as the first section 724a and move the second plunger 740 linearly.

Due to the track 724 having the above-described configuration, the second plunger 740 may continuously perform the combined movements described above. In a case in which the pin 743 moves along the track 724 in a reverse order, that is, from the third section 724c to the first section 724a, the second plunger 740 may also perform the above-described movements in the reverse order.

Figure 37:
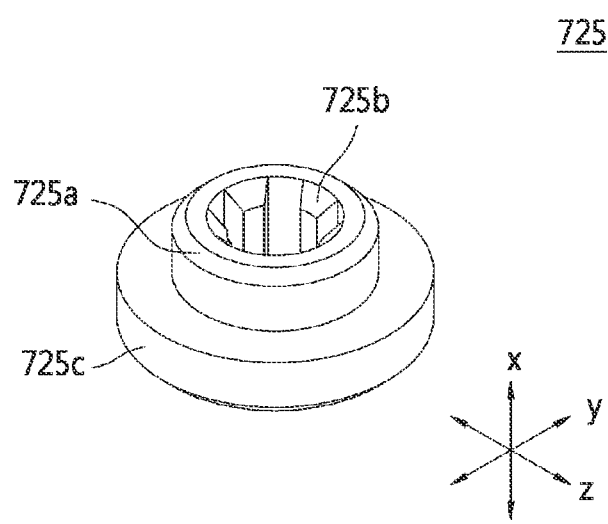

Referring to FIG. 37, the front housing 720 may include a guide 725 configured to guide movement of a first plunger 730 which will be described below. As illustrated in FIG. 30, the guide 725 may be coupled to the rear end of the rear housing 710. The guide 725 may include a body 725a inserted into the front housing 720 and serrations 725b formed on an inner circumferential surface of the body 725a. The serrations 725b of the guide 725 may be engaged with serrations 732 of the first plunger 730, and accordingly, the guide 725 may stably guide linear reciprocating motion of the first plunger 730. Also, the guide 725 may include a flange 725c that extends in a radial direction from an outer circumferential surface of the body 725a. The flange 725c may be caught at an end portion of the front housing 720 and thus allow the guide 725 to be stably installed.

Figure 38:
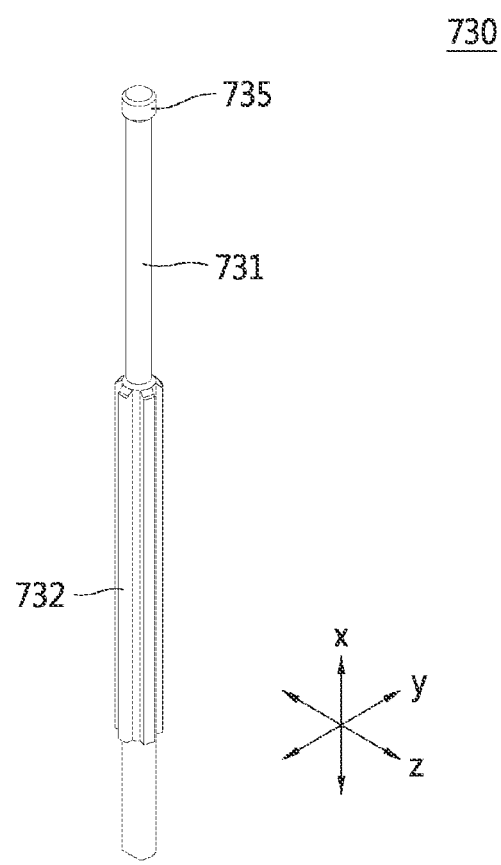

Referring back to FIG. 30, the actuator 700 may include the first plunger 730 disposed in the rear housing 710 and the front housing 720 which are coupled. As illustrated in FIG. 38, the first plunger 730 may include a body 731 formed as a rod and the serrations 732 formed on an outer circumferential surface of the body 731. The first plunger 730 may be disposed along the central axis of the actuator 700, that is, along the central axis of the rear housing 710 and the front housing 720 (in the x-direction) and may linearly reciprocate along the central axis.

Figure 39:
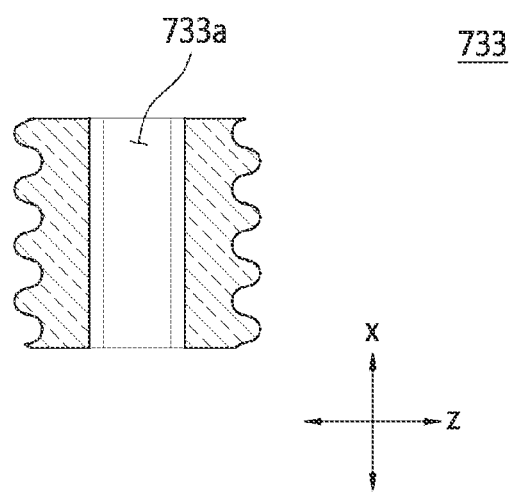

For the reciprocating motion of the first plunger 730, a propeller 733 may be disposed in the body 731 at the rear of the first plunger 730. Referring to FIG. 39, the propeller 733 may include a body having a predetermined size and threads formed on an outer surface of the body. The propeller 733 may have a through-hole 733a formed in the shape of a key and may be firmly key-coupled to a rear end portion of the body 731 using the through-hole 733a. Also, a washer 734 may be coupled to the front and rear of the propeller 733 to prevent the propeller 733 from being separated from the body 731.

The propeller 733 may be screw-coupled to the threads 714 formed inside the rear housing 710. Therefore, when the rear housing 710 rotates, the screw-coupled propeller 733 may move linearly in any one direction along the threads 714, and the entire first plunger 730 coupled thereto may also move linearly in any one direction. That is, the propeller 733 and the body 731 of the first plunger 730 coupled thereto may move forward or backward according to a direction in which the body 711 of the rear housing 710 rotates.

Also, the serrations 732 of the first plunger 730 may longitudinally extend along the body 731 and thus include a front end 732a and a rear end 732b. The second plunger 740 may include second serrations 745 disposed therein to be engaged with the serrations 732 (hereinafter referred to as first serrations 732) of the first plunger 730. However, according to the position, posture, or arrangement of the second plunger 740, e.g., the degree of rotation of the second plunger 740, that is controlled by the track 724, the second serrations 745 may be aligned to be selectively engaged with the first serrations 732 of the first plunger 730 that moves forward.

In other words, tops and bottoms of the second serrations 745 may be selectively aligned with bottoms and tops of the first serrations 732 that are disposed opposite the tops and bottoms of the second serrations 745. Therefore, when the second serrations 745 are not aligned to be engaged with the first serrations 732 due to rotation of the second plunger 740, the front end 732a of the first serrations 732 is caught at a rear end 745b of the second serrations 745 instead of being inserted into the second serrations 745, and the first plunger 730 that moves forward in the state in which the front end 732a is caught may cause the second plunger 740 to move forward together.

Also, when the second serrations 745 are aligned to be engaged with the first serrations 732 due to rotation of the second plunger 740 during the forward motion, the first serrations 732 may be engaged with the second serrations 745 and inserted into the second plunger 740. Here, since the first plunger 730 continues to move forward relative to the second plunger 740, the first plunger 730 may protrude to the outside of the second plunger 740. Meanwhile, the first plunger 730 may include a head 735 disposed at a front end to extend in a radial direction. The head 735 may be disposed outside the second plunger 740 at all times. Therefore, when the first plunger 730 retreats, the head 735 is caught at the second plunger 740, and accordingly, the second plunger 740 may also retreat with the first plunger 730.

Figure 40:
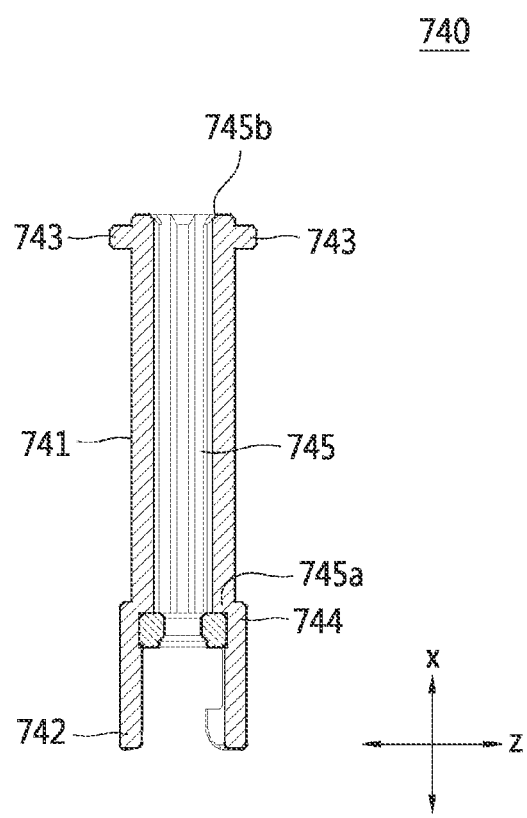

Meanwhile, referring to FIG. 40, the second plunger 740 may be disposed in the front housing 720 and include a cylindrical body 741 and a latch 742 provided at a front end of the body 741. The first plunger 730 may be disposed to pass through the body 741, and accordingly, the body 741 may be disposed between the first plunger 730 and the front housing 720, in other words, between the body 731 of the first plunger 730 and the body 721 of the front housing 720. As described above, the latch 742 may be selectively engaged with the latch 640 of the injector 600 according to the direction and degree of rotation of the second plunger 740 along the track 724.

Also, a stopper 744 may be disposed at a front end of the second plunger 740, and the stopper 744 may have a diameter that is larger than a diameter of the body 731 of the first plunger 730 but less than a diameter of the head 735.

Therefore, the head 735 of the first plunger 730 that retreats may be caught at the stopper 744, and accordingly, the second plunger 740 may also retreat. As described above, on an inner circumferential surface of the body 741 of the second plunger 740, the second serrations 745 may extend in a longitudinal direction of the body 741, and the second serrations 745 may include a front end 745a and the rear end 745b. The second serrations 745 may be aligned to be selectively engaged with the first serrations 732 of the first plunger 730 according to degree of rotation of the second plunger 740.

Also, the second plunger 740 may include the pin 743 provided on a rear outer circumferential portion thereof. As described above, the pin 743 is inserted into the track 724 of the front housing 720 and is guided by the track 724, and thus movement of the second plunger 740 connected thereto may also be controlled. Specifically, coupling between the pin 743 and the track 724 may control rotation of the second plunger 740 while driving is performed by the first plunger 730. Accordingly, it is possible to control not only the engagement between the latch 742 of the second plunger 740 and the latch 640 of the injector 600 but also engagement between the second serrations 745 of the second plunger 740 and the first serrations 732 of the first plunger 730.

For example, when the pin 743 is at a start point of the first section 724a while the first plunger 730 moves forward, the latch 742 of the second plunger 740 may not be engaged with the latch 640 of the injector 600, and the second serrations 745 may not be aligned with the first serrations 732. Then, when the pin 743 is guided through the first section 724a, the second plunger 740 may rotate as a whole by a predetermined angle. Therefore, due to the rotation, the latch 742 may also rotate and be engaged with the latch 640 to some extent, but the second serrations 745 may still not be aligned with the first serrations 732.

Then, when the pin 743 is guided through the third section 724c via the second section 724b, the second plunger 740 may further rotate as a whole in the same direction by a predetermined angle. Therefore, due to the rotation, the latch 742 of the second plunger 740 may also rotate and be completely engaged with the latch 640 of the injector 600, and the second serrations 745 may also be aligned with the first serrations 732. Meanwhile, while the first plunger 730 retreats, the pin 743 is guided from the third section 724c to the first section 724a, and accordingly, not only the engagement between the latch 742 of the second plunger 740 and the latch 640 of the injector 600 but also the engagement between the second serrations 745 and the first serrations 732 may be controlled in the reverse order from the above description.

9. Actuator Operation

FIGS. 43 to 48 are views for describing a process in which a drug is injected due to operation of an actuator of a medical cooling device, and FIGS. 49 to 54 are views for describing a process in which an injector is extracted from a cooling medium after drug injection.

First, each step of a drug injection process according to operation of the actuator 700 of the medical cooling device 10 will be described referring to FIGS. 43 to 48, and then each step of a process in which the injector 600 is extracted from the cooling medium 20 after drug injection will be described with reference to FIGS. 49 to 54.

Figure 43:
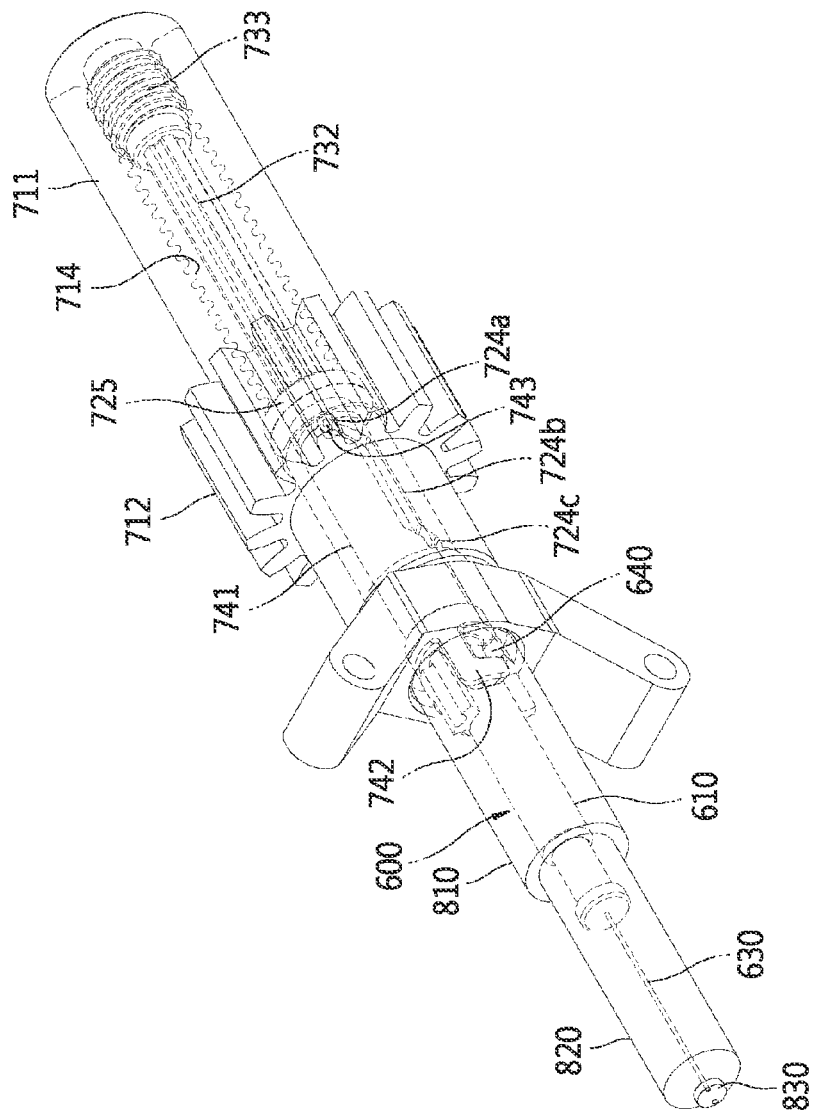
FIGS. 43 to 48 are views for describing a process in which a drug is injected due to operation of an actuator of the medical cooling device.
Figure 44:
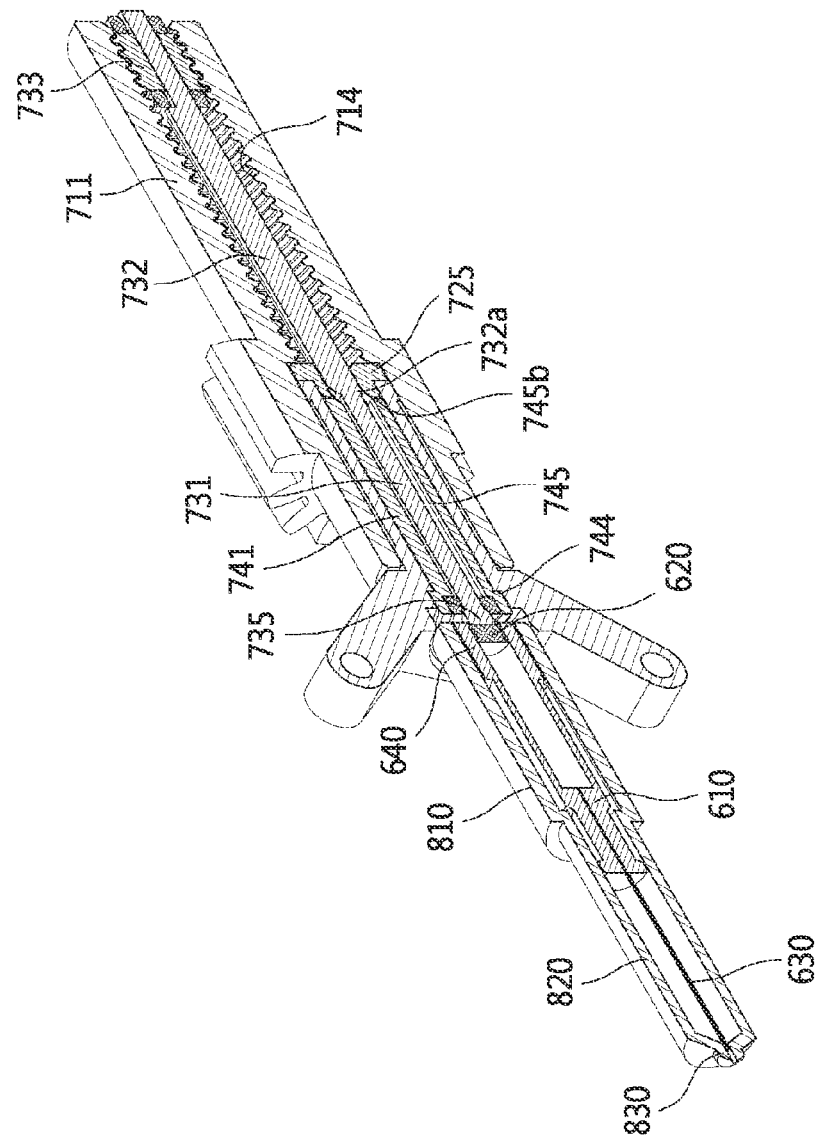

Referring to FIGS. 43 and 44, a configuration of the medical cooling device 10 prior to the injector 600 being loaded in the cooling medium 20 is shown. Specifically, the injector 600 may be disposed in the first body 810 of the insulator 800. In relation to the first plunger 730 of the actuator 700, the propeller 733 may be retreated to the rear end of the threads 714, and the head 735 may be disposed adjacent to the plug 620 of the injector 600. Also, in relation to the second plunger 740, since the second plunger 740 is not yet pushed by the first plunger 730, the pin 743 is located at the start point of the first section 724a of the track 724. Therefore, the front end 732a of the first serrations 732 of the first plunger 730 is caught at the rear end 745b of the second serrations 745 of the second plunger 740 instead of being inserted thereinto, and accordingly, when the first plunger 730 moves forward, the second plunger 740 may be pushed by the first plunger 730 in a state in which the second plunger 740 is caught by the first plunger 730.

Figure 45:
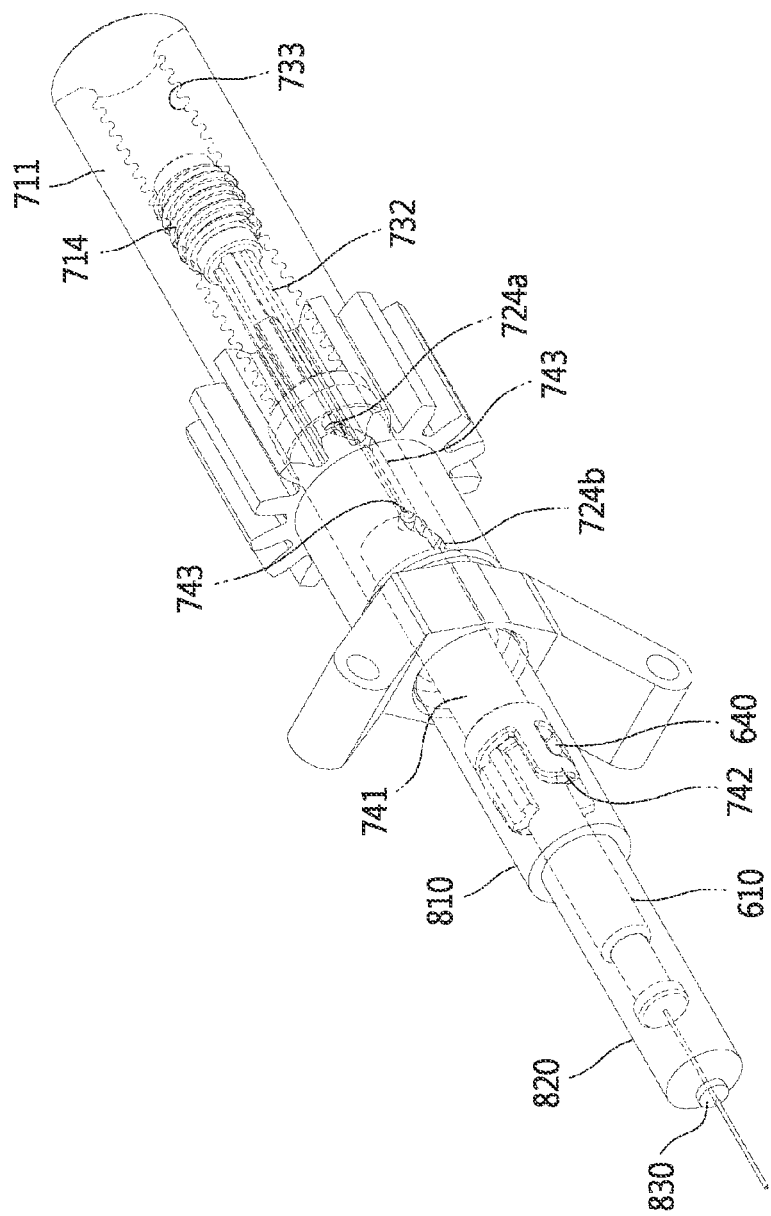
Figure 46:
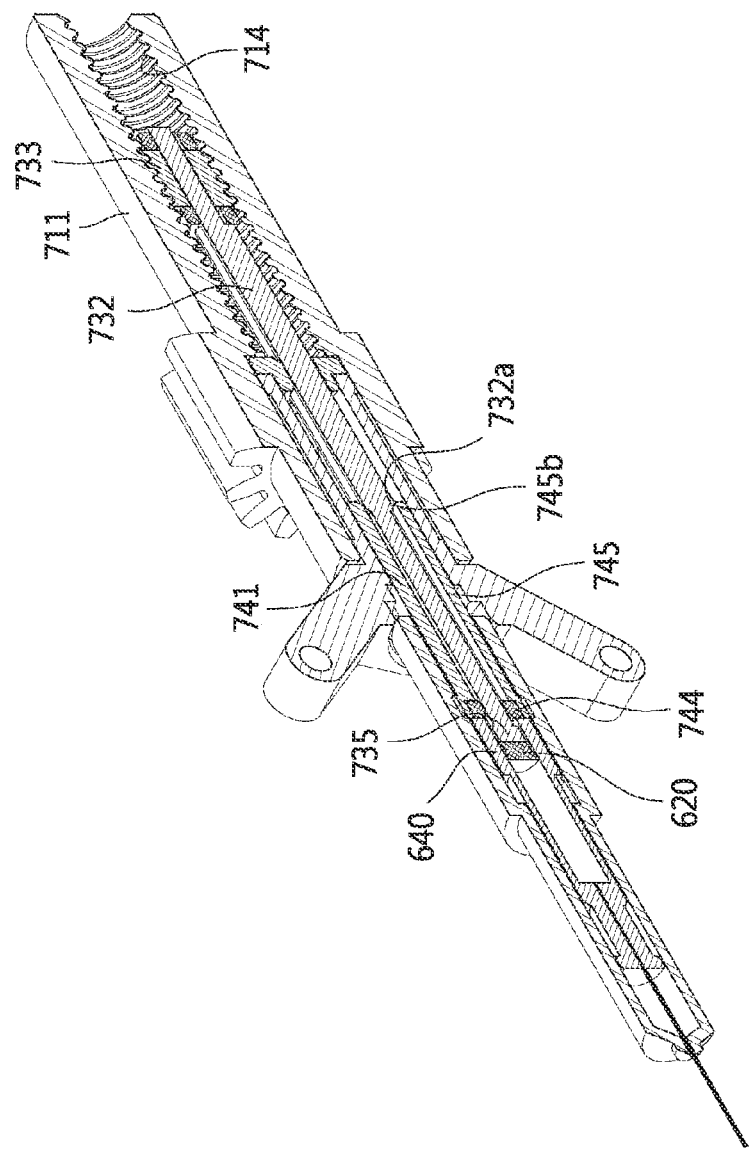

Then, referring to FIGS. 45 and 46, when the rear housing 710 rotates in any one direction, the propeller 733 may move forward by a predetermined distance along the threads 714, and the first plunger 730 may also move forward by the predetermined distance. Also, while the first plunger 730 moves forward by the predetermined distance, the second plunger 740 may also move forward by the same distance as the second plunger 740 is pushed by the front end 732a of the first serrations 732 that is caught at the rear end 745b of the second serrations 745 of the second plunger 740. Meanwhile, during the forward movement by the predetermined distance, the pin 743 may be guided up to the first section 742a and the second section 724b. Due to the guiding, the second plunger 740 may rotate by a predetermined angle, and accordingly, the latch 742 of the second plunger 740 may also rotate by the predetermined angle and be caught at the latch 640 of the injector 600. On the other hand, since, despite the guiding, the second serrations 745 are still not aligned with the first serrations 732, as described above, the second plunger 740 may continue to move forward due to the first plunger 730. Due to the forward movement of the second plunger 740, the injector 600 is pushed to move forward and, as illustrated, may enter the second body 820 of the insulator 800, that is, the cooling medium 20 surrounding the second body 820.

Figure 47:
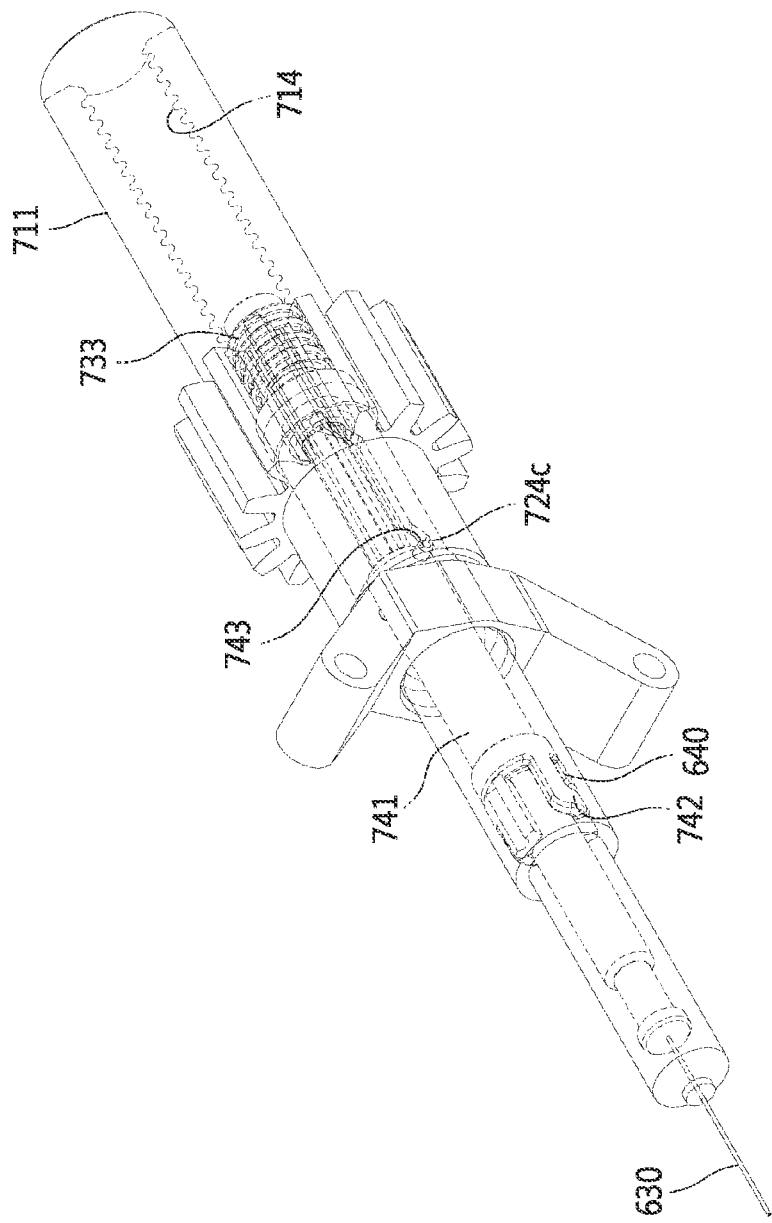
Figure 48:
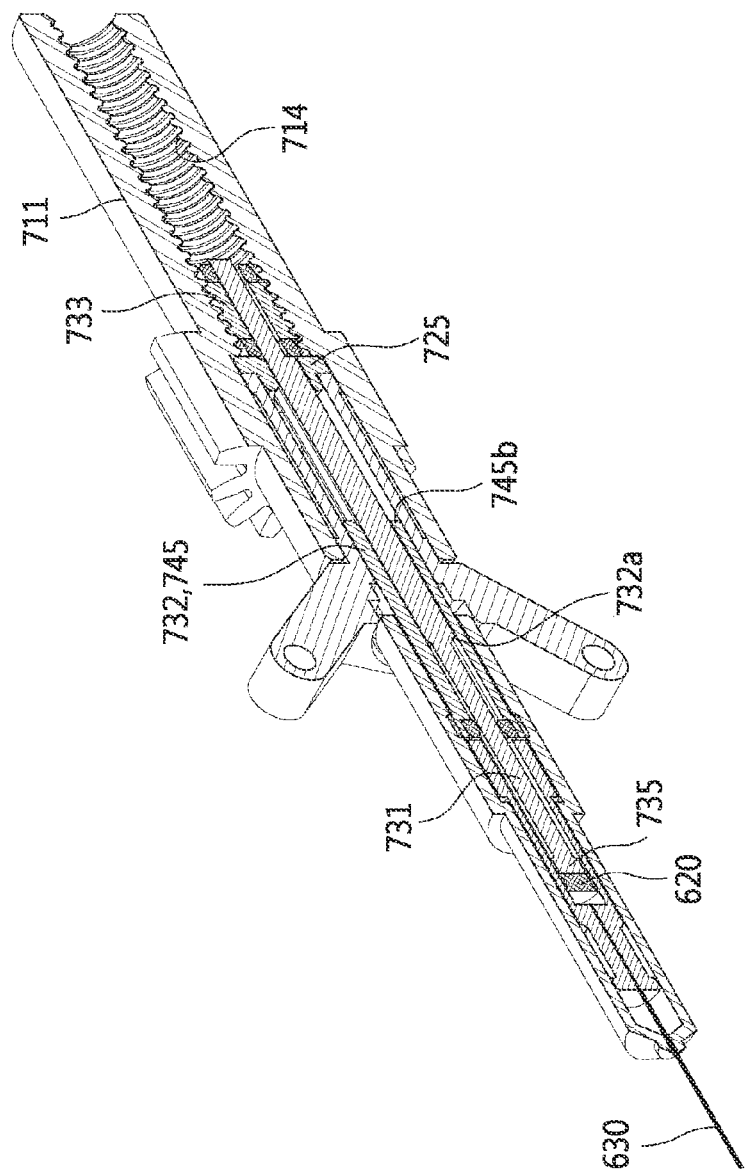

Then, referring to FIGS. 47 and 48, due to rotation of the rear housing 710 in any one direction, the first plunger 730 may continue to move forward, and accordingly, the second plunger 740 may also continue to move forward. Due to the forward movement, as illustrated, when the second plunger 740 moves forward so that the pin 743 is guided to an end of the third section 724c, the injector 600 may first be completely loaded in the second body 820 of the insulator 800, that is, in the cooling medium 20.

Also, due to the loading, the injecting part 630 of the injector 600 may protrude to the outside of the cooling medium 20 and reach a target region. Also, due to guiding of the pin 743 by the third section 724c, the second plunger 740 may further rotate in the same direction, and the latch 742 of the second plunger 740 may be completely engaged with the latch 640 of the injector 600.

Simultaneously, due to the rotation of the second plunger 740, the second serrations 745 may be aligned with the first serrations 732. The first serrations 732 may be engaged with the second serrations 745, and due to forward movement of the propeller 733, the first plunger 730 may continue to move forward through the second plunger 740 that is relatively stationary. Therefore, as illustrated, the head 735 of the first plunger 730 may push the plug 620 inside the injector 600, and the drug may be injected into the target region through the injecting part 630 that reached the target region.

When loading of the injector 600 and injection of the drug are completed as described above, there is a need to extract the injector 600 from the cooling medium 20. Hereinafter, a process of extracting the injector 600 on the basis of operation of the actuator 700 will be described.

Figure 49:
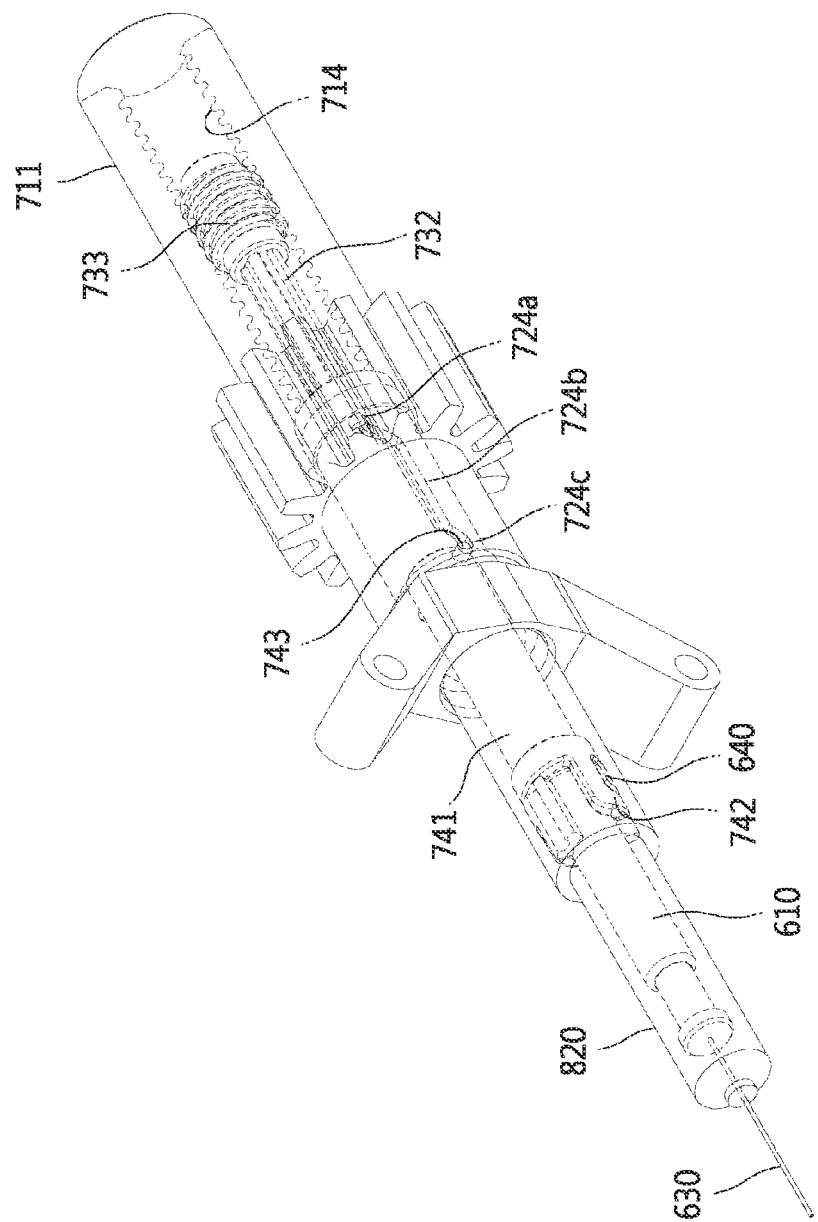
FIGS. 49 to 54 are views for describing a process in which an injector is extracted from a cooling medium after drug injection.
Figure 50:
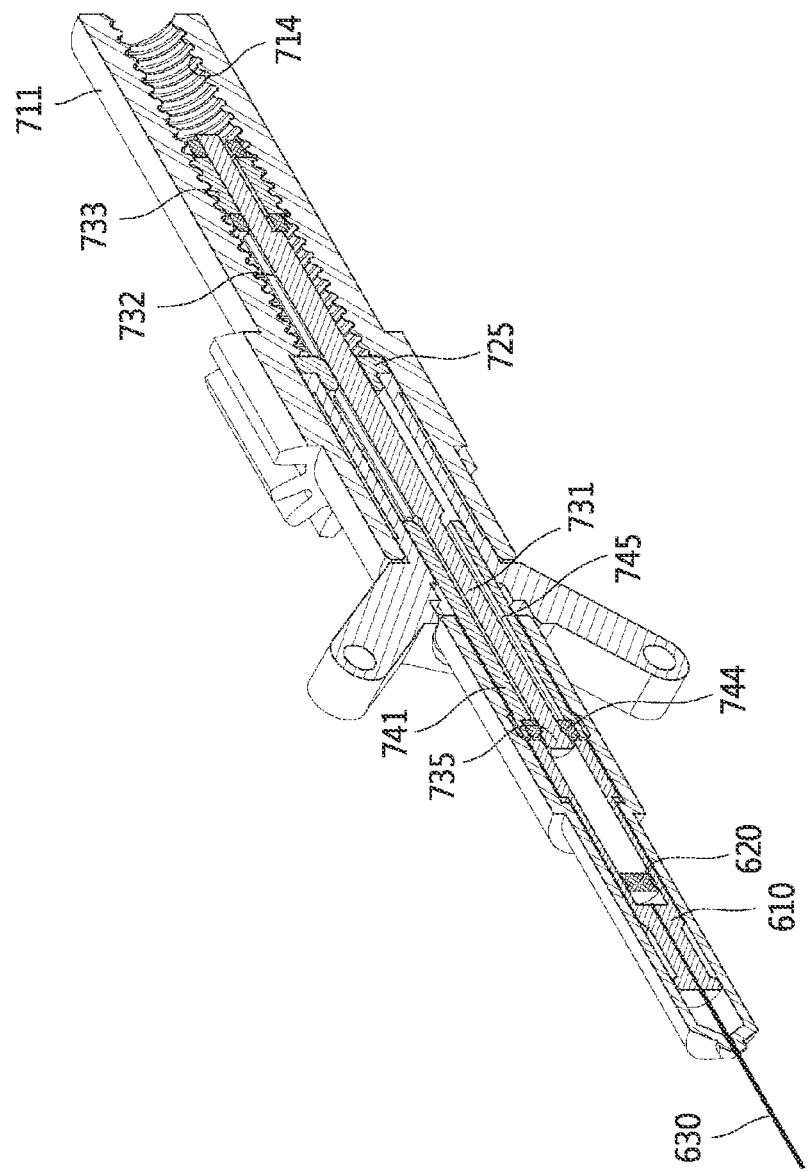

First, referring to FIGS. 49 and 50, after injection of the drug by the injector 600 is completed, when the rear housing 710 rotates in the opposite direction, the propeller 733 may retreat by a predetermined distance along the threads 714, and the first plunger 730 may also retreat by the predetermined distance. As illustrated, since the first plunger 730 is not caught at any portion of the second plunger 740, only the first plunger 730 may retreat. Due to the retreat by the predetermined distance, as illustrated in FIG. 50, the head 735 of the first plunger 730 may be caught at the stopper 744 of the second plunger 740.

Figure 51:
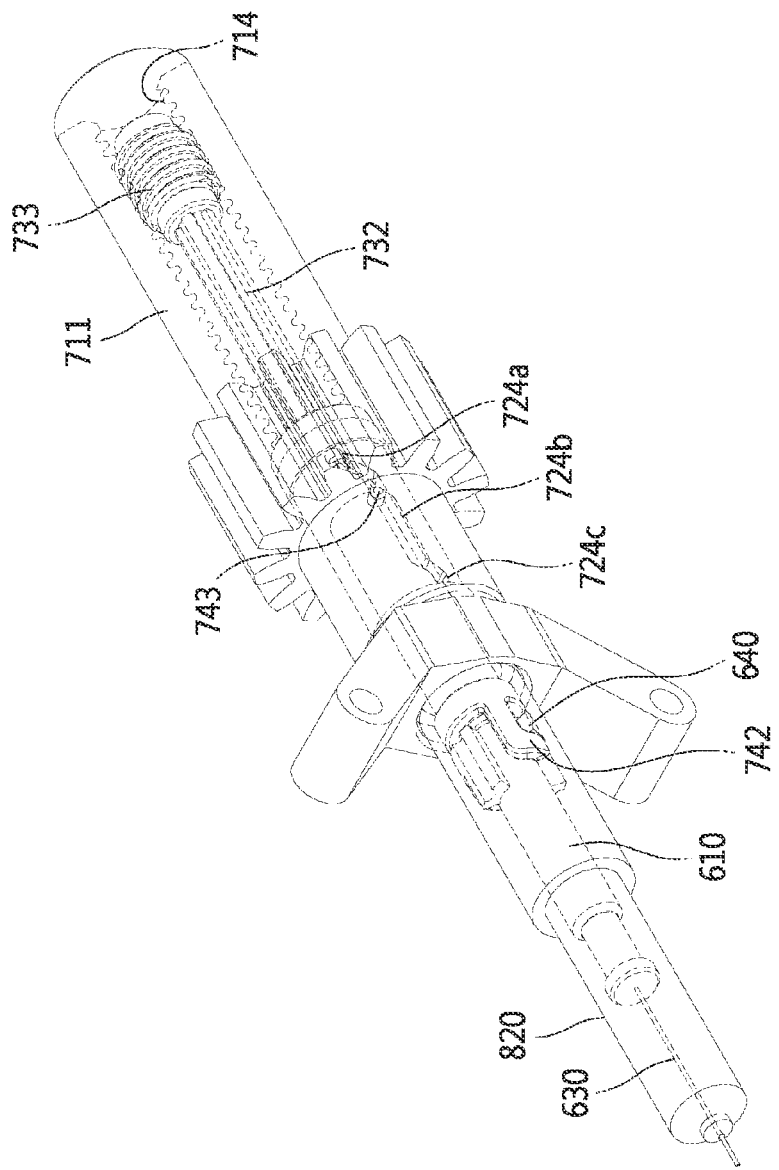
Figure 52:
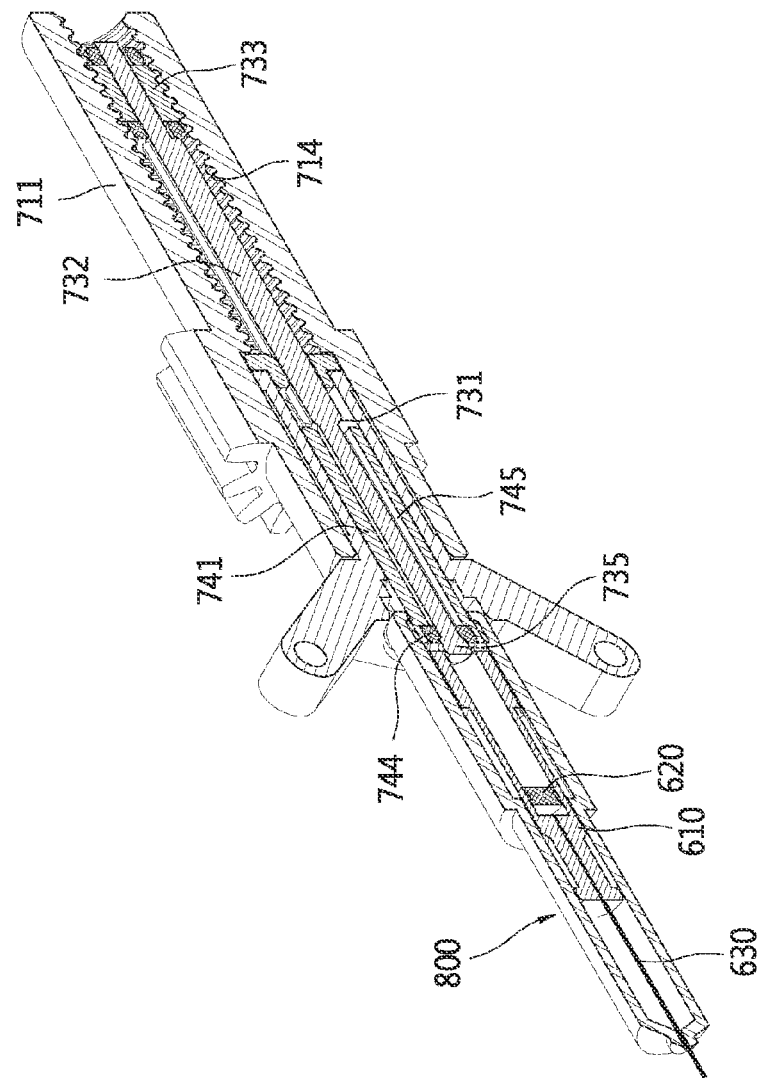

Then, referring to FIGS. 51 and 52, due to rotation of the rear housing 710 in the opposite direction, the first plunger 730 may continue to retreat. Also, in a state in which the head 735 of the first plunger 730 is caught at the stopper 744 of the second plunger 740, the second plunger 740 may also retreat. During the retreat, the pin 743 may be guided up to the third section 724c and the second section 724b. Due to the guiding, the second plunger 740 may rotate by a predetermined angle in a reverse direction, and accordingly, the latch 742 of the second plunger 740 may also rotate by the predetermined angle in the reverse direction but still remain caught at the latch 640 of the injector 600. Therefore, while the second plunger 740 retreats, the injector 600 caught thereby may also retreat and, as illustrated, begin to be extracted or unloaded from the second body 820 of the insulator 800, that is, from the cooling medium 20.

Figure 53:
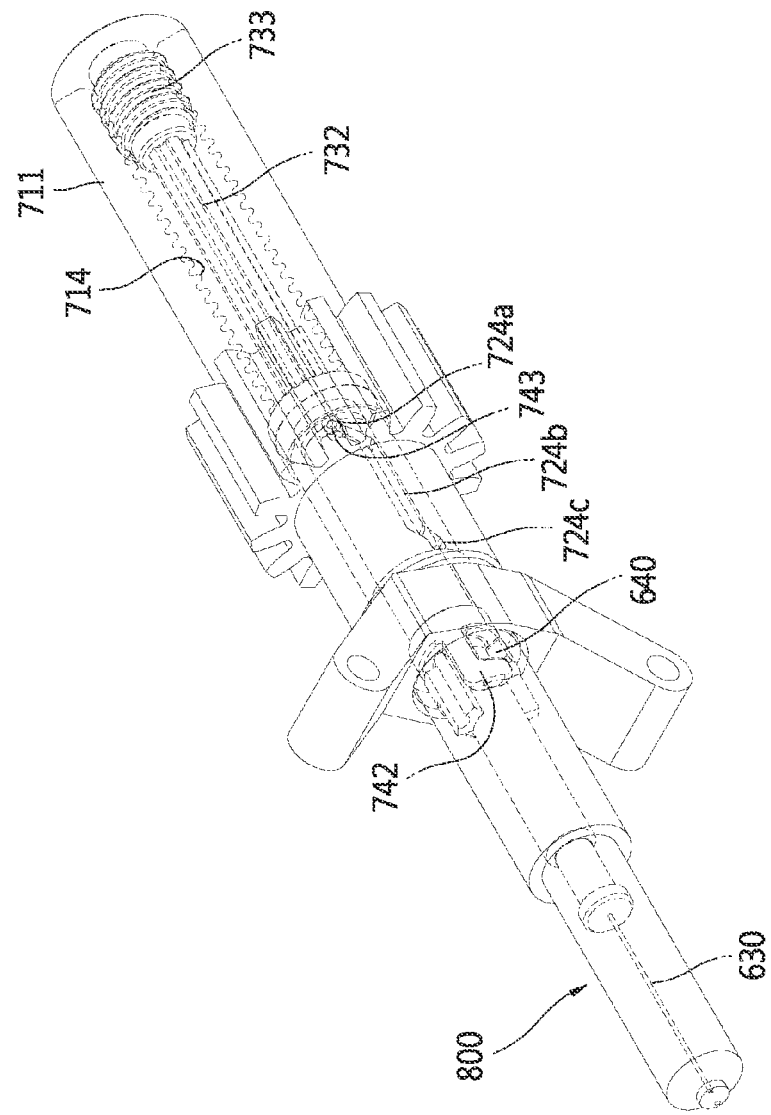
Figure 54:
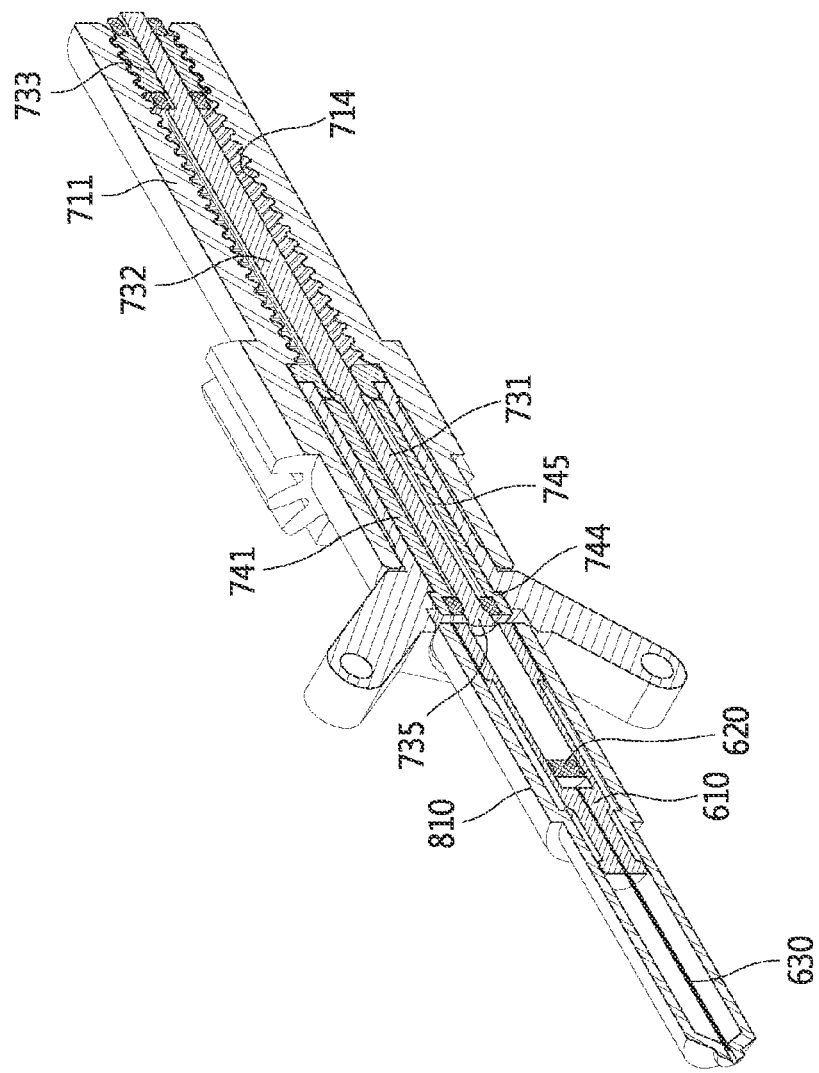

Then, referring to FIGS. 53 and 54, the propeller 733 may retreat to the rear end of the threads 714, and the first plunger 730 may return to its original position. Also, the second plunger 740 may return to its original position and be disposed in the front housing 720. Also, due to the return, the injector 600 may be completely extracted from the second body 820, that is, the cooling medium 20, and disposed in the first body 810 outside the cooling medium 20.

Also, while the returning operation is performed, the pin 743 may be further guided up to the first section 724a. Due to the guiding, the second plunger 740 may further rotate by a predetermined angle in the opposite direction. Therefore, the latch 742 may also rotate by the predetermined angle in the opposite direction and be completely released from the latch 640 of the injector 600, and the injector 600 may be separated from the cooling medium 20.

The injector 600 may be configured to be disposable or reusable. The disposable injector 600 may be extracted from the cooling medium 20 and then discarded. The reusable injector 600 may be extracted and then, for reuse, be refilled with drug.

As described above, the injector 600 according to an embodiment of the present invention may be selectively loaded in the cooling medium 20 by operation of the actuator 700. That is, the injector 600 may be loaded in the cooling medium 20 only when a drug is being injected, and the injector 600 may be extracted from the cooling medium 20 immediately after the drug is injected. In this way, since an intended drug may be prevented from freezing and be accurately injected, the stability and reliability of the medical cooling device 10 may be significantly improved.

10. Structure to Prevent Freezing of Medicinal Fluid

According to the present invention, since a storage unit in which a medicinal fluid is stored is disposed outside a solid cooling medium, freezing of the medicinal fluid may be prevented without a separate heating member configured to prevent the medicinal fluid from freezing. However, in order to prevent the medicinal fluid from freezing while passing through the solid cooling medium, a storage unit or an injecting part through which a liquid passes may be made of plastic or stainless steel for insulation, and the time taken for passage of the medicinal fluid may be controlled to be less than or equal to a predetermined amount of time. In this way, the medicinal fluid may be prevented from freezing while passing through the solid cooling medium.

In the present specification, the term "solid cooling medium" refers to a means for coming in solid contact with a target region using a cooling medium made of a solid material and may correspond to the cooling medium described so far. Hereinafter, in order to distinguish between cooling using a liquid and cooling using a solid, in the following description, a liquid being sprayed will be referred to as a liquid cooling medium, and the cooling medium described above will be referred to as a solid cooling medium.

Figure 55:
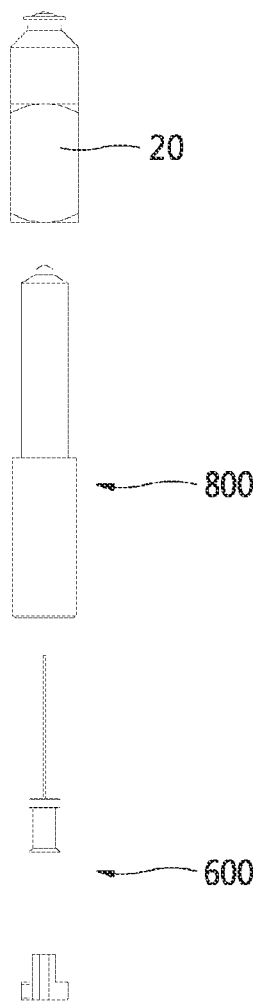
FIGS. 55 and 56 are views for describing a structure for preventing freezing of a medicinal fluid in the medical cooling device according to an embodiment of the present invention.
Figure 56:
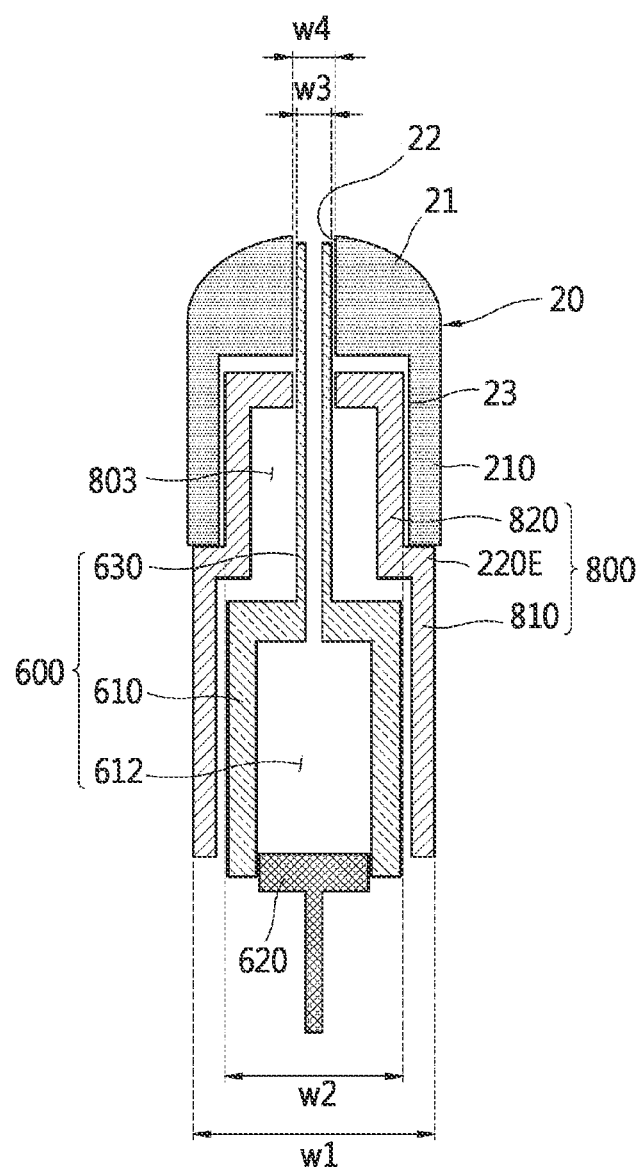

FIGS. 55 and 56 are views for describing a structure for preventing freezing of a medicinal fluid in the medical cooling device according to an embodiment of the present invention.

As described above, in a case in which the injector 600 including a medicinal fluid is mounted to the solid cooling medium 20, due to the solid cooling medium 20 that is cooled to a considerably low temperature within a short time to anesthetize a target region, the medicinal fluid in the injector 600 may freeze, and thus it may not be possible to properly release the medicinal fluid from the injector 600. Therefore, the medical cooling device 10 according to an embodiment of the present invention may include the insulator 800 which is an insulating member or allow the injector 600 to be placed outside the solid cooling medium 20 to prevent the medicinal fluid from freezing.

Referring to FIGS. 55 and 56, in one embodiment, the medical cooling device may include the insulator 800 which is an insulating member that is disposed between the solid cooling medium 20 and the injector 600 to prevent cooling energy of the solid cooling medium 20 from being transferred to the injector 600.

As described above, the solid cooling medium 20 may come in contact with a target region to cool the target region and perform a function of locally anesthetizing the target region and may have the accommodation space 23 disposed therein to accommodate the insulator 800. In order to effectively transfer cooling energy from the medical cooling device 10, the solid cooling medium 20 may be made of a material having a high thermal conductivity, e.g., gold (Au), silver (Ag), copper (Cu), aluminum (Al), or the like.

The insulator 800 is a configuration for thermally insulating the injector 600 disposed inside the solid cooling medium 20 from the solid cooling medium 20 and may be made of a material that at least has a thermal conductivity lower than that of the solid cooling medium 20. The solid cooling medium 20 may not only perform a cooling function but also serve as a cartridge that stores a drug therein and injects the drug as necessary. However, in this case, since a problem occurs in that the drug placed inside the solid cooling medium 20 freezes due to a lower temperature of the solid cooling medium 20, a separate heating member configured to apply heat to the drug should be included. Through the insulator 800 that spatially separates the injector 600, in which the drug is stored, from the solid cooling medium 20, the medical cooling device 10 according to an embodiment of the present invention may simplify the structure because there is no need to include the heating member.

The insulator 800 may be made of a material different from that of the solid cooling medium 20. Specifically, the insulator 800 may have a thermal conductivity lower than that of the solid cooling medium 20 and have a thermal conductivity of 50 W/m-K or lower, preferably, 20 W/m-K or lower. For example, the insulator 800 may be made of a ceramic material such as glass, quartz, alumina, zirconia, and aluminum nitride or a plastic material such as polytetrafluoroethylene (PTFE), polyethylene, polyvinylidene fluoride (PVDF), polycarbonate, polyetheretherketone (PEEK), and fluoropolymer. Meanwhile, in order to have durability to withstand repeated coupling with the solid cooling medium 20 by being repeatedly attached to and detached from the solid cooling medium 20, the insulator 800 may be made of a material having a predetermined stiffness. For example, the insulator 800 may be made of a metal material of which a thermal conductivity is 20 W/m-K or lower, such as stainless steel or a steel alloy. However, the present invention is not limited to the materials listed above as examples, and of course, any other material that may insulate the injector 600 from the solid cooling medium 20 may be applied as the material of the insulator 800.

The insulator 800 may include the first body 810 having a first diameter W1 and the second body 820 connected to a front end of the first body 810 and having a second diameter W2 that is smaller than the first diameter W1. The insulator 800 may be fitted to the accommodation space 23 of the solid cooling medium 20 through the second body 820 and may accommodate the injector 600 through the first body 810. As described above, since the insulator 800 includes the first body 810 and the second body 820 whose diameters are different, an intermediate end portion 220E is formed, and since the intermediate end portion 220E makes it impossible for the injector 600 to be fitted further after being fitted to the first body 810, spatial separation between the injector 600 and the solid cooling medium 20 may be possible.

In particular, through such a configuration, only the injecting part 630 of the injector 600 is disposed in the second body 820 of the insulator 800, and thus the drug passes through a region where the injector 600 overlaps with the solid cooling medium 20 only when the drug is being injected. Here, due to air in an internal space 803 of the second body 820, it is possible to implement a double insulation effect with the solid cooling medium 20 and the injector 600.

The injecting part 630 according to the present invention serves to inject a liquid to an external target region. To this end, the injecting part 630 may include a discharge part configured to discharge a liquid and may further include an injection part configured to inject the liquid into the target region, a spray part configured to spray the liquid widely to the target region, and the like. The insulator 800 may be provided in a form that may be detached from the solid cooling medium 20. Since the solid cooling medium 20 comes in direct contact with a target region of a subject receiving treatment, the solid cooling medium 20 may be configured to be disposable to prevent contamination of the treatment site. Here, the insulator 800 that does not come in direct contact with the target region of the subject receiving treatment may be used multiple times, and to this end, the insulator 800 may be provided to be detachable from the solid cooling medium 20.

The injector 600 may have a thermal conductivity lower than that of the solid cooling medium 20. For example, the injector 600 may be made of a material having a thermal conductivity of 20 W/m-K or less. For example, the injector 600 may be made of materials such as plastic or stainless steel. The injector 600 may be made of a material or structure having a predetermined stiffness to accommodate a drug therein and withstand a pressure due to operation of the actuator 700. In another embodiment, the injector 600, or at least the body 610 of the injector 600, may be made of the same material as the insulator 800.

The injector 600 may include the body 610, the reservoir 612 formed inside the body 610, and the injecting part 630 configured to discharge the drug accommodated in the reservoir to the outside. Here, the injecting part 630 may not only refer to the shape of a needle that passes through the skin of the target region but also refer to a discharge part in the shape of a tube having a third diameter W3. Therefore, in the case in which the injecting part 630 is formed in the shape of a tube, since there is no need to insert the injecting part 630 into the skin of the target region, there is no need for the injecting part 630 to be exposed to the outside of the solid cooling medium 20, specifically, the tip 21 of the solid cooling medium 20. Meanwhile, the injecting part 630 of the injector 600 passes through the first path 22 formed in the solid cooling medium 20 and then discharges or injects the drug to the outside, and in this process, the drug may be exposed to the low temperature of the solid cooling medium 20 through the first path 22. Therefore, after the injector 600 moves into the insulator 800, the medical cooling device 10 may allow injection of the drug to be completed within a preset amount of time to prevent freezing of the medicinal fluid due to the exposure while the medicinal fluid is being discharged.

Also, in the injector 600, the third diameter W3 of the injecting part 630 may be formed to be smaller than a fourth diameter W4 of the first path 22 of the solid cooling medium 20 to an extent that the injecting part 630 does not come in direct contact with the first path 22. In this way, it is possible to prevent the cooling energy of the solid cooling medium 20 from being transferred to the injecting part 630.

The injecting part 630 of the injector 600 may be made of a material having a low thermal conductivity. According to an embodiment of the present invention, all or some of the elements of the injector may be provided in the form of a cartridge so as to be replaceable. The injector 600 may use a barrel containing a medicinal fluid of a conventional syringe.

11. Liquid Cooling and Spraying Structure

According to the present invention, a medicinal fluid may be sprayed onto a target region to serve as a liquid cooling medium so that the cooling effect may be improved while the medicinal fluid performs its function.

In a case in which a liquid is ejected using a syringe in the form of a cartridge in a cooling medium, cooling using the cooling medium and cooling using the liquid may be combined and the cooling effect may be increased. Also, pain may occur at a treatment site in a disinfection process, and as the liquid is diffused to a region, with which the cooling medium is not able to come in contact, and cools the target region to generate a cryoanesthetic effect, there is an effect of reducing pain while a disinfecting function is performed. Hereinafter, for convenience of description, the medicinal fluid will be referred to as "liquid cooling medium."

According to the present invention, a liquid drug (e.g., an anesthetic solvent) may be sprayed onto a treatment site using a syringe without a needle or using a cartridge in the shape of a barrel, and the discharged liquid may be diffused and serve to cool or anesthetize a large target region.

Figure 57:
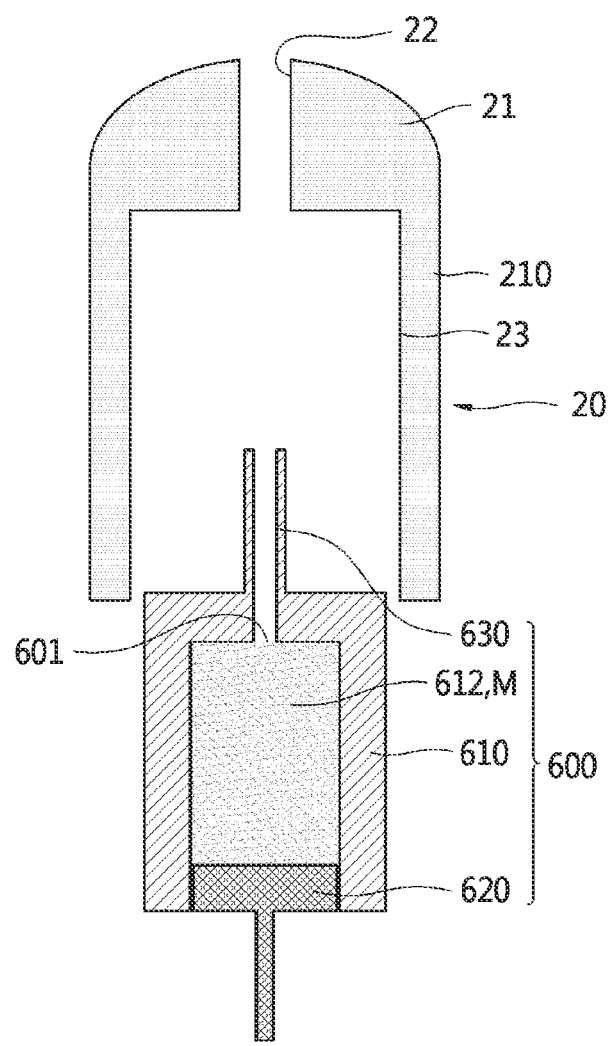
FIGS. 57 to 59 are views for describing cooling and spraying methods using a liquid.
Figure 58:
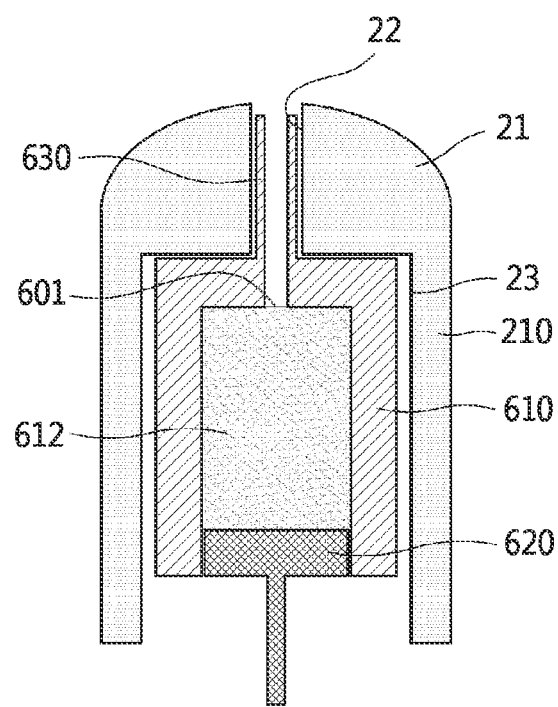
Figure 59:
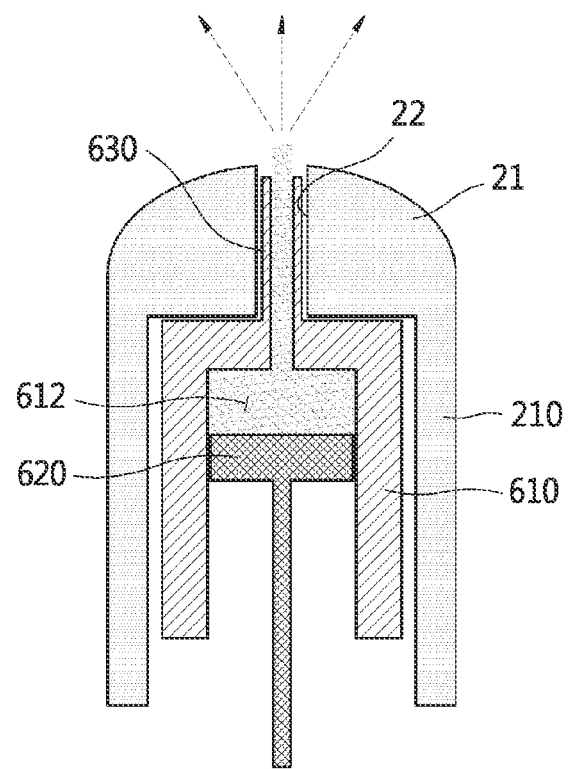

FIGS. 57 to 59 are views for describing cooling and spraying methods using a liquid.

Here, the medical cooling device 10 sprays a liquid onto a target area to cool the target area and may include the insulator 800 to spatially separate the injector 600 and the solid cooling medium 20, but since spraying of a liquid and cooling are possible without including the insulator 800, description of the insulator 800 will be omitted.

The medical cooling device 10 according to an embodiment of the present invention may include the injector 600 configured to accommodate a liquid, and the injector 600 and the solid cooling medium 20 may be disposed to be spatially separated. In one embodiment, the injector 600 may accommodate a therapeutic agent for treating a target region, e.g., an eyeball, or a liquid containing an ophthalmic drug or an ophthalmic composition. In such a case, the injector 600 may include the injecting part 630 formed in the shape of a needle that is inserted into a target region to inject the therapeutic agent to the target region.

In the present disclosure, the term "ophthalmic drug" or "ophthalmic composition" may refer to an anesthetic injected prior to the treatment of ocular disease or a medicine used to treat, ameliorate, or prevent the ocular disease.

In the present disclosure, the term "ocular disease" may refer to a disease that affects or relates to a part or an area of the eye or the entire eye. In a broad sense, the eye may include an eyeball, tissues and body fluids that make up the eyeball, muscles around the eye (such as rectus and oblique), and the optic nerve in or near the eyeball.

In another embodiment, referring to FIGS. 57 to 59, the injector 600 may include the injecting part 630 formed as a discharge part in the shape of a tube and may spray a liquid accommodated therein to a target region. First, as illustrated in FIG. 57, in order to prevent freezing of the liquid accommodated in the injector 600, the injector 600 is disposed outside the solid cooling medium 20. Here, in order to prevent discharge of a liquid M accommodated in the reservoir 612, the injector 600 may further include a sealing film 601 disposed between the reservoir 612 and the injecting part 630 that communicates therewith. When a predetermined pressure is applied to the sealing film 601, the sealing film 601 is broken and allows the liquid to be discharged to the outside.

Here, the liquid M sprayed by the injector 600 may include an anesthetic solvent that anesthetizes a target region or a disinfectant that disinfects the target region. Various bacteria that may cause diseases may be present in the target region. For example, in an eyeball which is a target region, bacteria such as *Staphylococcus aureus*, Coagulase-negative staphylococci, *Streptococcous, Propionibacterium acnes, Bacillus cereus, Enterococcus faecalis, Klebsiella pneumoniae, Enterococcus, Pseudomonas aeruginosa*, Enterobacteriaceae, *Candida albicans, Aspergillus*, and *Fusarium* may be present. The medical cooling device 10 may spray a disinfectant for sterilizing the above bacteria to perform disinfection before injection of a medicinal fluid containing the actual therapeutic agent.

For example, in a case in which the liquid M contains a disinfectant, the disinfectant may be a mixture mixed with at least one of isopropyl alcohol, povidone-iodine, and benzalkonium chloride. More specifically, the isopropyl alcohol may be 70% isopropyl alcohol, and the povidone-iodine may be a 5% povidone-iodine solution. Also, the benzalkonium chloride may be 0.4% benzalkonium chloride.

Here, the medical cooling device 10 according to an embodiment of the present invention may move the injector 600 to the accommodation space 23 accommodated in the solid cooling medium 20 to lower a temperature of the liquid M accommodated in the injector 600. As illustrated in FIG. 58, since the injector 600 is directly accommodated in the solid cooling medium 20 without the insulator 800 therebetween, the injector 600 may be directly affected by the low temperature of the solid cooling medium 20. In this way, the liquid M accommodated in the injector 600 may reach a low temperature that may cool the target region. However, in order to prevent the liquid M from freezing while being cooled to a predetermined cooling temperature, the medical cooling device 10 may control the actuator 700 connected to the injector 600 so that the liquid M may be sprayed to the outside within a preset amount of time.

Although not illustrated, the plug 620 of the injector 600 may be connected to the actuator 700, and the medical cooling device 10 sprays the liquid M to the outside as the plug 620 moves due to operation of the actuator 700. The liquid M accommodated in the reservoir 612 moves to the injecting part 630, which has a relatively narrow diameter, due to the plug 620 and then is discharged to the outside. Due to a pressure difference in the discharging process, the liquid M may be sprayed in the form of mist or droplets. The sprayed liquid M, which is cooled to a low temperature, is discharged and diffused, and thus it is possible to disinfect a target region having a wide area. In other words, a first cooling area cooled by the liquid being discharged and diffused to the outside may be larger than a second cooling area cooled by the solid cooling medium 20. Here, in the injecting part 630 which is the discharge part, the size, length, shape, or the like of the discharge part may be preset to control the amount and direction of the sprayed liquid M.

In particular, since the medical cooling device 10 may spray the liquid M, which is cooled by receiving cooling energy from the solid cooling medium 20, onto the target region, it is possible to simultaneously perform disinfection and cooling using the liquid M. In this case, since the medical cooling device 10 not only performs a cooling action using the solid cooling medium 20 but also performs a cooling action the liquid M, the cooling effect may be improved. Also, since, through cooling by spraying a liquid, the medical cooling device 10 generates a cryoanesthetic effect in a wider region as compared to when cooling is only performed using the solid cooling medium 20, it is possible to implement an effect of reducing pain while the disinfecting function is performed.

12. Multi-Step Temperature Control Cooling Protocol

Hereinafter, using the control unit 170, a cooling protocol utilizing multi-step temperature control will be described.

The control unit 170 may control operation of the cooling generator 113 on the basis of a temperature detected by the temperature sensor unit 145. For example, the control unit 170 may control time during which cryoanesthesia is performed or the like on the basis of an ambient air temperature, a temperature of the cooling medium 20, or an air temperature provided from the temperature sensor unit 145. The control unit 170 may control operation of the cooling generator 113 on the basis of a temperature measurement signal provided from the temperature sensor unit 145 to control the temperature of the cooling medium 20. Specifically, while the cooling medium 20 is in a temperature range of −100° C. to 15° C., the medical cooling system 1 according to embodiments of the present invention may selectively set and control a temperature range according to the purpose. Through the temperature control, the medical cooling system 1 may perform cooling action while controlling a surface of a treatment site to be in a temperature range of −50° C. to 15° C.

Also, the control unit 170 may control the cooling generator 113 so that the cooling medium 20 maintains a predetermined temperature while cryoanesthesia is performed. In another embodiment, two or more temperature values may be preset, and the control unit 170 may control the cooling generator 113 so that the cooling medium 20 has each temperature value sequentially or periodically while cooling is performed.

In a case in which the temperature or time exceeds the preset temperature or time, the control unit 170 may prevent excessive cooling of the treatment site through control such as turning off the power of the cooling generator 113. This is merely one embodiment, and of course, the temperature and time may be preset in various ranges.

Here, the control unit 170 may include all kinds of devices capable of processing data, such as a processor. Here, for example, the term "processor" may refer to a data processing device embedded in hardware that has a physically structured circuit to perform a function expressed by a code or a command included in a program. Examples of the data processing device embedded in hardware include processing devices such as a microprocessor, a central processing unit (CPU), a processor core, a multiprocessor, an application-specific integrated circuit (ASIC), and a field programmable gate array (FPGA), but the scope of the present invention is not limited thereto.

Also, the control unit 170 may control the time during which cryoanesthesia is performed or the like on the basis of a pressure signal provided from the pressure sensor unit 141. The control unit 170 may receive a pressure measurement signal from the pressure sensor unit 141 and, when the received pressure measurement signal has a value greater than a preset reference value, determine that the front end portion 225 of the cooling medium 20 has come in contact with a treatment site of a patient. Here, the control unit 170 may check time during which contact with the treatment site of the patient occurs and check a temperature measurement signal and, when cooling has been performed for a predetermined amount of time at a temperature that is within a preset range, determine that anesthetizing the treatment site of the patient is completed.

Figure 60:
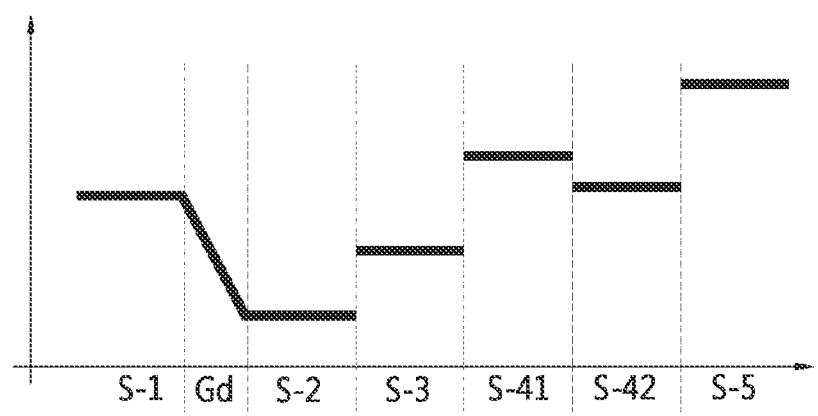
FIGS. 60 to 64 are views for describing technology related to multi-step temperature control technology.
Figure 61:
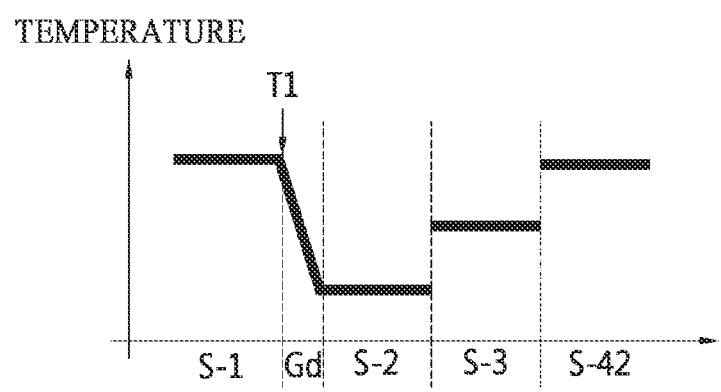
Figure 62:
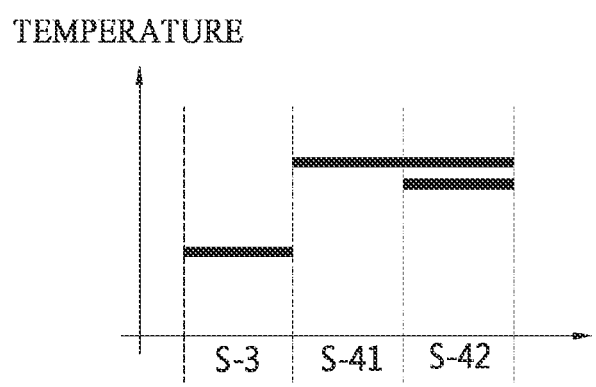
Figure 63:
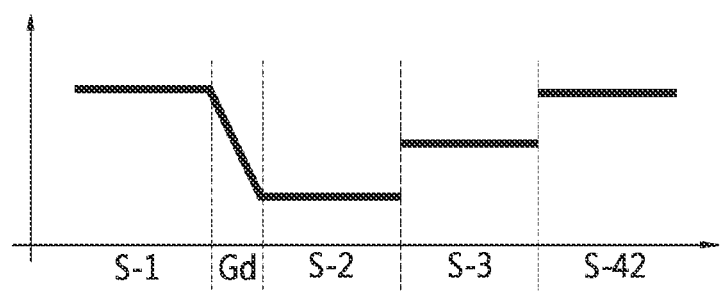
Figure 64:
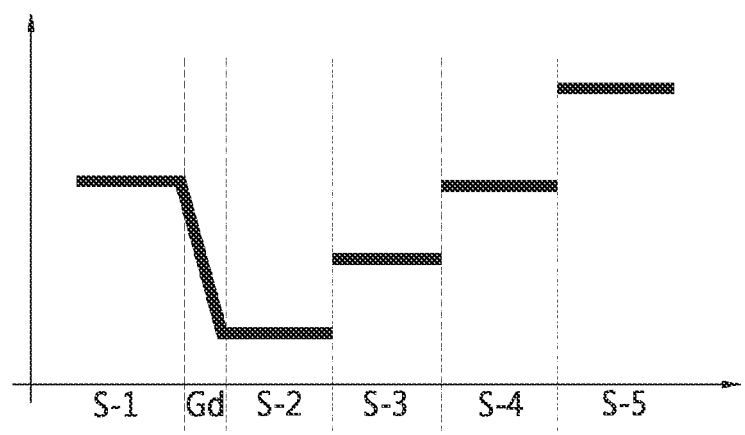

FIG. 60 is a conceptual diagram for describing the overall temperature protocol using the medical cooling system, and FIG. 61 is a view for describing an attaching step (S-1) in the overall temperature protocol of FIG. 60. FIGS. 62 and 63 are views for describing a detaching step (S-41-42) in the overall temperature protocol of FIG. 60, and FIG. 64 is a view for describing a drying step (S-5) in the overall temperature protocol of FIG. 60.

Referring to FIG. 60, the overall temperature protocol using the medical cooling system according to another embodiment of the present invention may include the attaching step (S-1), a cooling and disinfecting step (S-2), a cryoanesthesia step (S-3), a detaching step (S-41, S-42), and the drying step (S-5). A height difference between the steps illustrated in the drawing indicate a relative difference between temperatures at which the steps are performed. Here, the overall temperature protocol using the medical cooling system is not necessarily performed including all the illustrated steps, and of course, steps necessary for individual treatment may be selectively performed. Here, even when some of the steps are omitted, a cooling method using the medical cooling system may perform the remaining steps while a relative temperature difference is maintained.

First, the attaching step (S-1) will be described with reference to FIG. 61.

In a case in which an operator brings a cooling medium, which is cooled using the medical cooling system, in direct contact with a target region of a patient, a contact portion may stick to the cooling medium due to a sharp temperature difference between the target region and the cooling medium. The attaching step (S-1) according to the present invention is for addressing the above-mentioned problem even when the operator uses the medical cooling system in an unprepared state as described above. In the attaching step (S-1), the cooling medium may be controlled to maintain a temperature higher than a temperature in the cooling and disinfecting step (S-2). Here, a temperature range in the attaching step (S-1) may be −10° C. or higher. Also, the temperature range in the attaching step (S-1) may be −5° C. or higher.

Meanwhile, the medical cooling system according to another embodiment of the present invention may further include a timer (not illustrated). In order to prevent a problem when the operator brings a cooled cooling medium in contact with a target region of a patient in an unprepared state as described above, the medical cooling system may control the cooling medium to stay in the attaching step (S-1) even when the operator presses a power button for treatment and then, using the timer (not illustrated) in which a preset amount of time is stored, the medical cooling system may control the cooling medium to proceed to the cooling and disinfecting step (S-2) after a predetermined amount of time T1 passes. Here, the cooling medium may skip the cooling and disinfecting step (S-2) and directly proceed to the cryoanesthesia step (S-3). In other words, the medical cooling system may control a cooling temperature of the cooling medium before the cooling medium is brought into contact with the target region, which is the treatment site, to be different from a cooling temperature of the cooling medium after the timer is operated. Alternatively, the medical cooling system may allow the temperature in the attaching step (S-1) to be different from the temperature in the cooling and disinfecting step (S-2) or the temperature in the cryoanesthesia step (S-3). In another embodiment, of course the medical cooling system may be turned off by a user's manipulation instead of being turned off due to elapse of a predetermined amount of time.

Here, the overall temperature protocol using the medical cooling system may have a gradual temperature section Gd having a gentle temperature change slope from the attaching step (S-1) to the cooling and disinfecting step (S-2). In other words, the overall temperature protocol induces a temperature change in each section from the attaching step (S-1) to the cooling and disinfecting step (S-2) to be gradual so that the temperature slowly reaches the final target cooling temperature, and the extent to which a patient feels a change in temperature during a cooling process is minimized. Thus, an inconvenience of the patient may be minimized.

Then, the cooling and disinfecting step (S-2) may be a step in which the target region is disinfected to a temperature lower than that in the attaching step (S-1) using the medical cooling system. The cooling and disinfecting step (S-2) may be performed in a temperature range that may kill or reduce the activity of bacteria that may be present on the target region, that is, on a skin surface of the treatment site. In the cooling method according to an embodiment, a third temperature range that is −2° C. or lower, e.g., a third temperature range of −90° C. to −2° C., may be applied to cool the target region. In this way, the bacteria may be killed or the activity thereof may be reduced to perform disinfection before the target region is anesthetized or the medicinal fluid is injected into the target region. However, the technical idea of the present invention is not limited thereto, and the third temperature range may be set in consideration of a temperature range in which the bacteria present on the target region may be sterilized. Here, the cooling and disinfecting step (S-2) may have a temperature range that is lower than the lowest temperature in the cryoanesthesia step (S-3). Since the temperature in the disinfecting step is intended to sterilize bacteria or reduce the activity of bacteria, the temperature should have a temperature range that is lower than a temperature range in which anesthesia is actually performed.

Then, in the cryoanesthesia step (S-3), cooling may be performed on the target region to a preset temperature range to anesthetize the target region. The temperature range in the cryoanesthesia step (S-3) may be a temperature range higher than −2° C. and lower than or equal to 0° C., which is higher than the temperature range in the cooling and disinfecting step (S-2).

Then, the detaching step (S-42) will be described with reference to FIGS. 62 and 63.

The detaching step (S-42) refers to a step in which, after the cryoanesthesia step (S-3) is performed, the medical cooling device is separated from the target region. Here, a phenomenon in which the surface of the target region sticks to the cooling medium may occur due to cooling, and in a case in which the medical cooling device is separated immediately, damage may occur to the surface of the target region. In order to prevent such damage, the overall temperature protocol may control the temperature of the cooling medium before the cooling medium is separated from the target region to be different from the temperature in the cryoanesthesia step (S-3). In the detaching step (S-42), post-cooling may be performed in a temperature range that is a preset temperature or higher. The temperature during post-cooling may be different from the temperature in the cooling and disinfecting step (S-2) or the temperature in the cryoanesthesia step (S-3). Specifically, the temperature during post-cooling may be higher than the temperature in the cooling and disinfecting step (S-2) or the temperature in the cryoanesthesia step (S-3).

Meanwhile, the medical cooling system may further include a notification unit (not illustrated). In the detaching step (S-42), using the notification unit (not illustrated), the medical cooling system may notify the operator to immediately detach the cooling medium from the target region after the temperature rises to a temperature higher than the temperature in the cooling and disinfecting step (S-2) or the temperature in the cryoanesthesia step (S-3) in order to perform post-cooling. The notification unit (not illustrated) may provide a notification signal to the outside using various signals such as sound, light, and vibration. The notification unit (not illustrated) may provide the notification signal when a preset amount of time passes after the cooling medium reaches a preset temperature or higher.

Meanwhile, the overall temperature protocol may further include, between the cryoanesthesia step (S-3) and the detaching step (S-42), a drug anesthesia and disinfection step (S-41) in which a drug is used to anesthetize or disinfect the target region. In such a case, the detaching step (S-42) may be performed immediately after the drug is injected. In one embodiment, a temperature range in the drug anesthesia and disinfection step (S-41) may be the same as the temperature range in the detaching step (S-42). In another embodiment, the temperature range in the detaching step (S-42) may be different from the temperature range in the drug anesthesia and disinfection step (S-41). For example, the temperature range in the detaching step (S-42) may be lower than the temperature range in the drug anesthesia and disinfection step (S-41).

Then, the drying step (S-5) will be described with reference to FIG. 64.

The drying step (S-5) may be a step in which, after the cooling medium is completely separated from the target region of the patient after use, the temperature of the cooling medium is maintained in a predetermined temperature range for a preset amount of time to remove moisture or the like generated during cooling. For example, in the drying step (S-5), the cooling medium may be controlled to have a temperature range of 20° C. or higher to dry the moisture generated during cooling in the cooling and disinfecting step (S-2) or the cryoanesthesia step (S-3) so that contamination of the device is prevented and durability of the device is improved. In another embodiment, in the drying step (S-5), the cooling medium may be controlled to have a temperature range of 30° C. or higher. The medical cooling system may control operation of the cooling generator to allow the cooling medium to have the above-mentioned temperature range. Specifically, the medical cooling system may control a direction of current of a thermoelectric element to be opposite to that in the steps in which cooling is performed. In this way, the cooling medium may be rapidly heated to a temperature at which drying is performed.

As described above, the cooling method using the medical cooling system 1 allows the temperature to be maintained in different temperature ranges in each step according to multiple steps. The medical cooling device 10 may control output of the cooling generator 113, which is configured to generate cooling energy, to maintain the temperatures according to the multiple steps. Here, the medical cooling device 10 may apply the maximum current or maximum voltage allowed by the cooling generator 113 to perform high-speed cooling to a specific temperature or lower.

Although a number of examples have been described, it should be understood that other modifications and implementations can be devised by those skilled in the art that will fall within the spirit and scope of the principles of this disclosure. More particularly, various variations and modifications in the structure or the configuration are possible within the scope of the disclosure, the drawings and the appended claims. In addition to variations and modifications in the configuration, alternative uses will also be apparent to those skilled in the art.

DESCRIPTION OF REFERENCE NUMERALS

1: medical cooling system
10: medical cooling device

What is claimed is:

1. A handheld medical cooling device, comprising:
a cooling medium in thermal communication with a target area to cool the target area;
a first cooling generator configured in a shape of a plane having a first major surface and a first minor surface, wherein the first major surface and the first minor surface are substantially parallel, and wherein the first major surface is in thermal communication with the cooling medium;
a second cooling generator configured in a shape of a plane having a second major surface and a second minor surface, wherein the second major surface and the second minor surface are substantially parallel, wherein the second major surface is in thermal communication with the cooling medium, and wherein the cooling medium is disposed between the first major surface and the second major surface;
a first coupler contacting the first minor surface of the first cooling generator such that the first cooling generator is disposed between the first coupler and the cooling medium;
a second coupler contacting the second minor surface of the second cooling generator such that the second cooling generator is disposed between the second coupler and the cooling medium,
wherein in response to the first major surface supplying a cooling energy to the cooling medium during cooling of the target area, the first minor surface is configured to supply a heating energy to the first coupler, and
wherein in response to the second major surface supplying a cooling energy to the cooling medium during cooling of the target area, the second minor surface is configured to supply a heating energy to the second coupler;
a heat dissipation unit comprising a plurality of dissipation fins and disposed at a rear portion of the handheld medical cooling device opposite to a portion at which the cooling medium is disposed;
a first heat pipe having a pipe shape extending in a longitudinal direction of the cooling medium, wherein a first end of the first heat pipe contacts the first coupler and a second opposite end of the first heat pipe contacts the heat dissipation unit such that the heating energy supplied by the first cooling generator is transferred from the first cooling generator to the heat dissipation unit via the first coupler; and
a second heat pipe having a pipe shape extending in the longitudinal direction of the cooling medium, wherein a first end of the second heat pipe contacts the second coupler and a second opposite end of the second heat pipe contacts the heat dissipation unit such that the heating energy supplied by the second cooling generator is transferred from the second cooling generator to the heat dissipation unit via the second coupler,
wherein the heat dissipation unit is configured to discharge the heating energy from the first heat pipe and the second heat pipe to an outside.

2. The handheld medical cooling device of claim 1, and wherein the cooling medium, the first cooling generator, the second cooling generator, the first heat pipe, the second heat pipe, and the heat dissipation unit are arranged in a first body portion extending in a first direction which is substantially parallel to the longitudinal direction of the cooling medium.

3. The handheld medical cooling device of claim 2, further comprising: a controller disposed in a second body portion extending in a second direction not parallel to the first direction.

4. The handheld medical cooling device of claim 3, wherein the controller is configured to activate and deactivate the first cooling generator and the second cooling generator such that the cooling medium maintains a predetermined temperature range while the cooling medium supplies the cooling energy to the target area.

5. The handheld medical cooling device of claim 1, wherein the first cooling generator and the second cooling generator are arranged symmetrically with respect to a longitudinal axis of the cooling medium.

6. The handheld medical cooling device of claim 5, wherein a cooling center region is positioned on an extension line extending from a midpoint of the first major surface and the second major surface along the longitudinal direction of the cooling medium, wherein the midpoint of the first major surface and the second major surface is a midpoint of a connecting line connecting virtually a center of mass of the first major surface and a center of mass of the second major surface, wherein the cooling center region has a cooling center which is a center of a thermal conductance of the cooling center region, wherein a distance from a front end of the cooling medium to the cooling center is 30 mm or less, and wherein the front end of the cooling medium is one end contacting the target area or a cooling tip.

7. The handheld medical cooling device of claim 6, wherein a position of the cooling center region is determined by a cooling center parameter of the cooling medium.

8. The handheld medical cooling device of claim 7, wherein the cooling center parameter of the cooling medium includes at least one of a thermal conductivity of the cooling medium, a volume of the cooling medium, a distance between the cooling medium and the first cooling generator, or a distance between the cooling medium and the second cooling generator.

9. The handheld medical cooling device of claim 7, wherein the cooling center parameter further includes an amount of the cooling energy of the first cooling generator and an amount of the cooling energy of the second cooling generator.

10. The handheld medical cooling device of claim 1, wherein the first coupler comprises a first contact surface contacting the first minor surface of the first cooling generator such that the first cooling generator is interposed between the first coupler and the cooling medium and a first fixing surface fixing the first heat pipe to the first coupler, wherein the second coupler comprises a second contact surface contacting the second minor surface of the second cooling generator such that the second cooling generator is interposed between the second coupler and the cooling medium and a second fixing surface fixing the second heat pipe to the second coupler, and wherein the first coupler and the second coupler are arranged symmetrically with respect to a longitudinal axis of the cooling medium.

11. The handheld medical cooling device of claim 1, and wherein the heat dissipation unit further comprises a plurality of fans configured to generate an air flow in a perpendicular direction relative to the longitudinal direction of the heat dissipation unit.

12. The handheld medical cooling device of claim 1, wherein the heat dissipation unit comprises at least one first heat dissipation section and at least one second heat dissipation section, the first heat dissipation section corresponds to the first heat pipe and the second heat dissipation section corresponds to the second heat pipe, and wherein the first heat dissipation section and the second heat dissipation section are arranged symmetrically with respect to a longitudinal axis of the heat dissipation unit.

13. The handheld medical cooling device of claim 12, the handheld medical cooling device further comprising:
a cooling concentrator disposed adjacent to a front end of the cooling medium and protruding to the outside relative to the front end of the cooling medium, wherein the front end of the cooling medium is one end contacting the target area or a cooling tip, and wherein the cooling concentrator and a cooling center are positioned on a straight line extending virtually along the longitudinal direction of the cooling medium.

14. The handheld medical cooling device of claim 1, wherein the first cooling generator is configured to supply the cooling energy via a first contacting area, wherein the second cooling generator is configured to supply the cooling energy via a second contacting area, wherein the cooling medium is configured to supply the cooling energy via a third contacting area, wherein the first contacting area is larger than the third contacting area, and wherein the second contacting area is larger than the third contacting area.

15. The handheld medical cooling device of claim 1, wherein the cooling medium directly contacts the target area.

16. The handheld medical cooling device of claim 1, wherein the cooling medium indirectly contacts the target area through a cooling tip.

* * * * *